United States Patent [19]
Peterson, Jr. et al.

[11] Patent Number: 6,133,304
[45] Date of Patent: Oct. 17, 2000

[54] ACE INHIBITOR-MMP INHIBITOR COMBINATIONS

[75] Inventors: Joseph Thomas Peterson, Jr., Brighton; Milton Lethan Pressler, Saline, both of Mich.

[73] Assignee: Warner-Lambert Company, Morris Plains, N.J.

[21] Appl. No.: 09/485,253

[22] PCT Filed: Nov. 10, 1998

[86] PCT No.: PCT/US98/23993

§ 371 Date: Feb. 7, 2000

§ 102(e) Date: Feb. 7, 2000

[87] PCT Pub. No.: WO99/32150

PCT Pub. Date: Jul. 1, 1999

Related U.S. Application Data

[60] Provisional application No. 60/068,594, Dec. 23, 1997.

[51] Int. Cl.$^7$ ................................. A61K 31/40; A61K 31/195
[52] U.S. Cl. ................................................. 514/414; 514/562
[58] Field of Search ...................................... 514/562, 414

[56] References Cited

U.S. PATENT DOCUMENTS 5,756,545  5/1998  O'Brien et al. ........................ 514/414

FOREIGN PATENT DOCUMENTS

WO 91/17771  11/1991  WIPO.
WO 96/24373  8/1996  WIPO.
WO 97/44315  11/1997  WIPO.

OTHER PUBLICATIONS

Li et al., J. Mol. Cell. Cardiology, vol. 30, No. 7, p. 254, Jul. 1998.

Baxter et al., Bioorganic & Medicinal Chemistry Letters, vol. 7, No. 7, pp. 897–902, Apr. 1997.

*Primary Examiner*—Raymond Henley, III
*Attorney, Agent, or Firm*—Charles W. Ashbrook

[57] ABSTRACT

The present invention relates to compositions comprising a compound which inhibits the actions of angiotensin-converting enzyme and a compound which inhibits the actions of matrix metalloproteinase enzymes and the use of such compositions for treating ventricular dilation, heart failure and cardiovascular fibrotic pathologies.

10 Claims, 8 Drawing Sheets

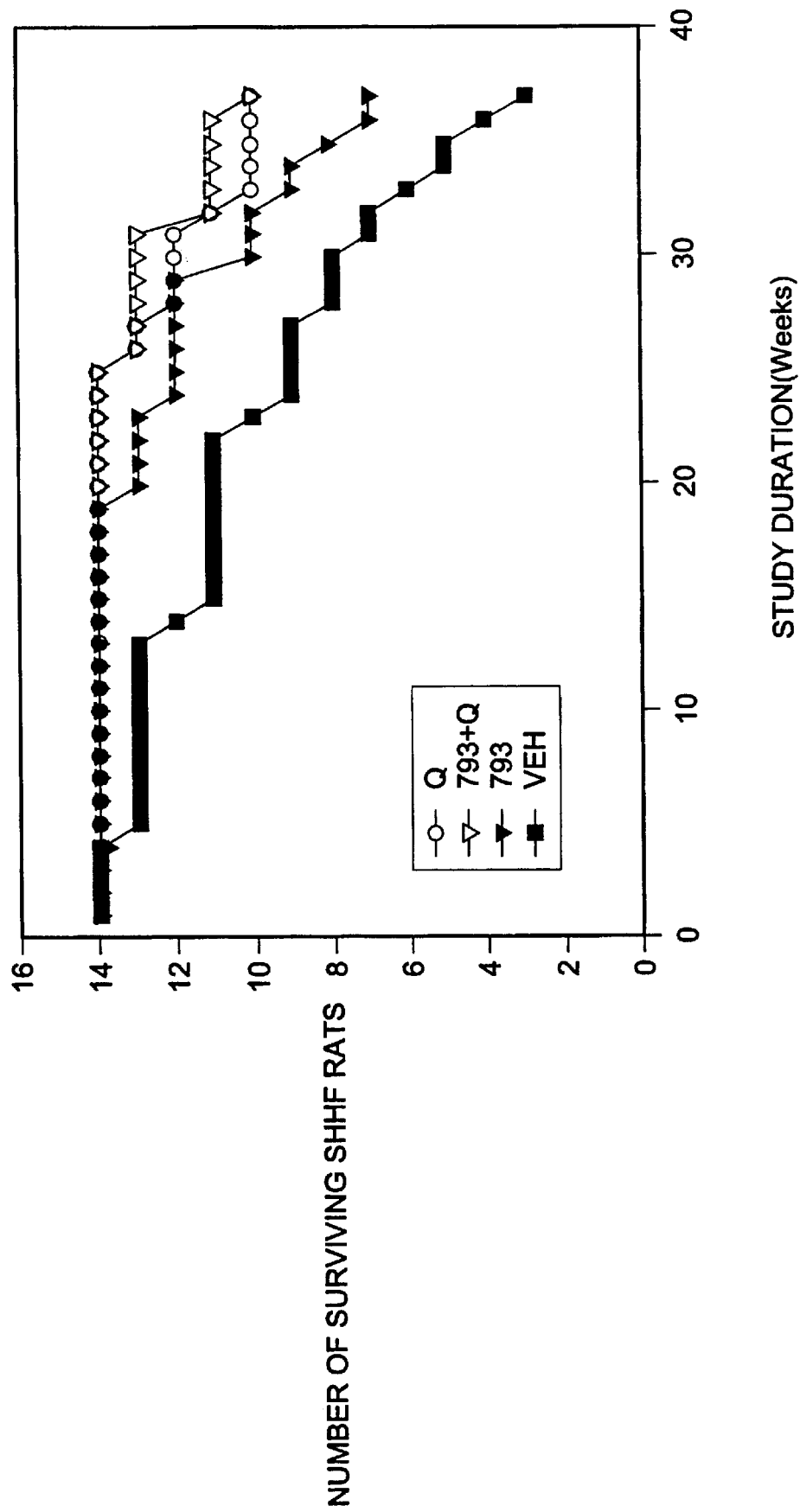
FIG-1 793 SHHF-2 STUDY MORTALITY

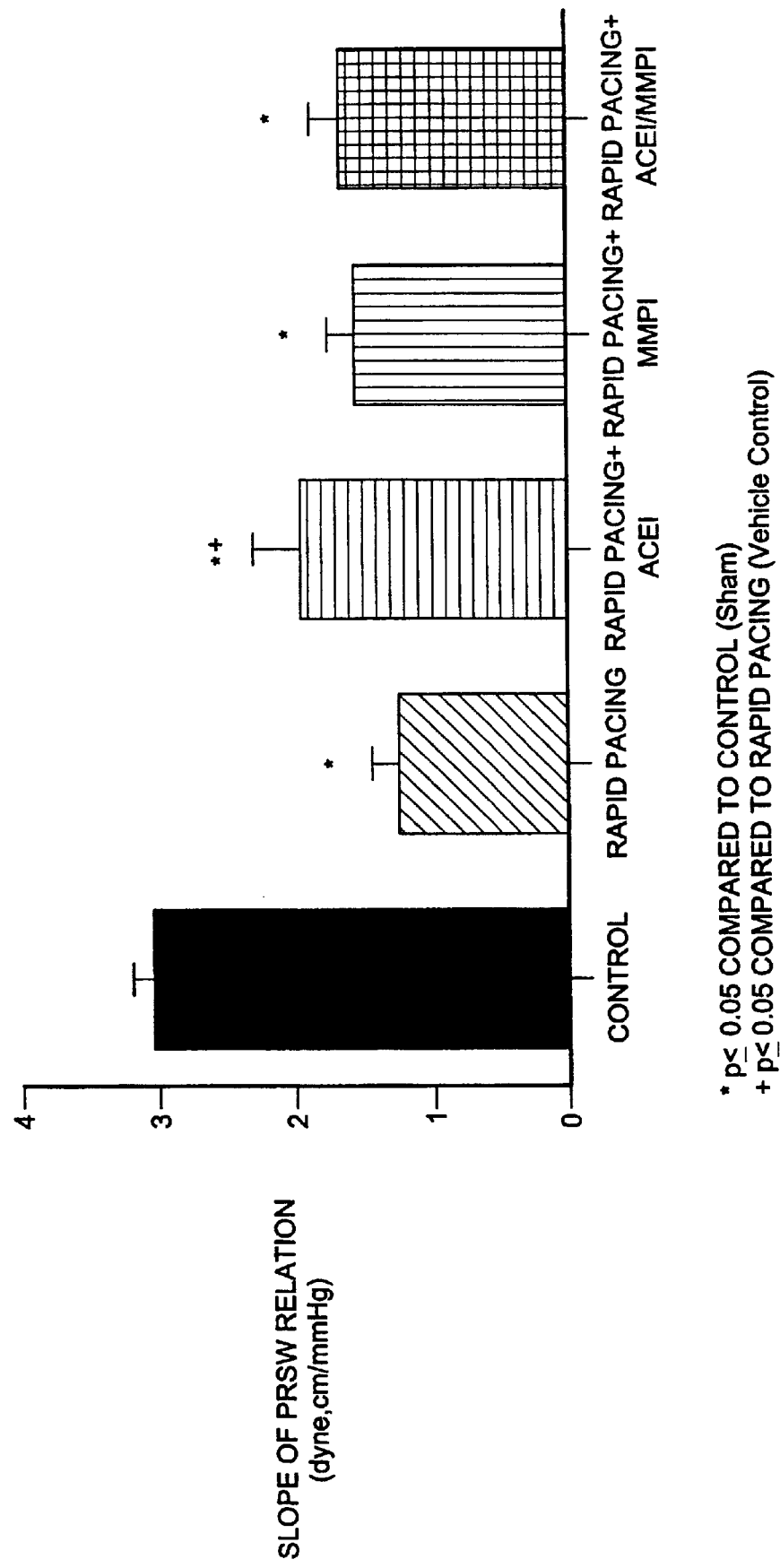

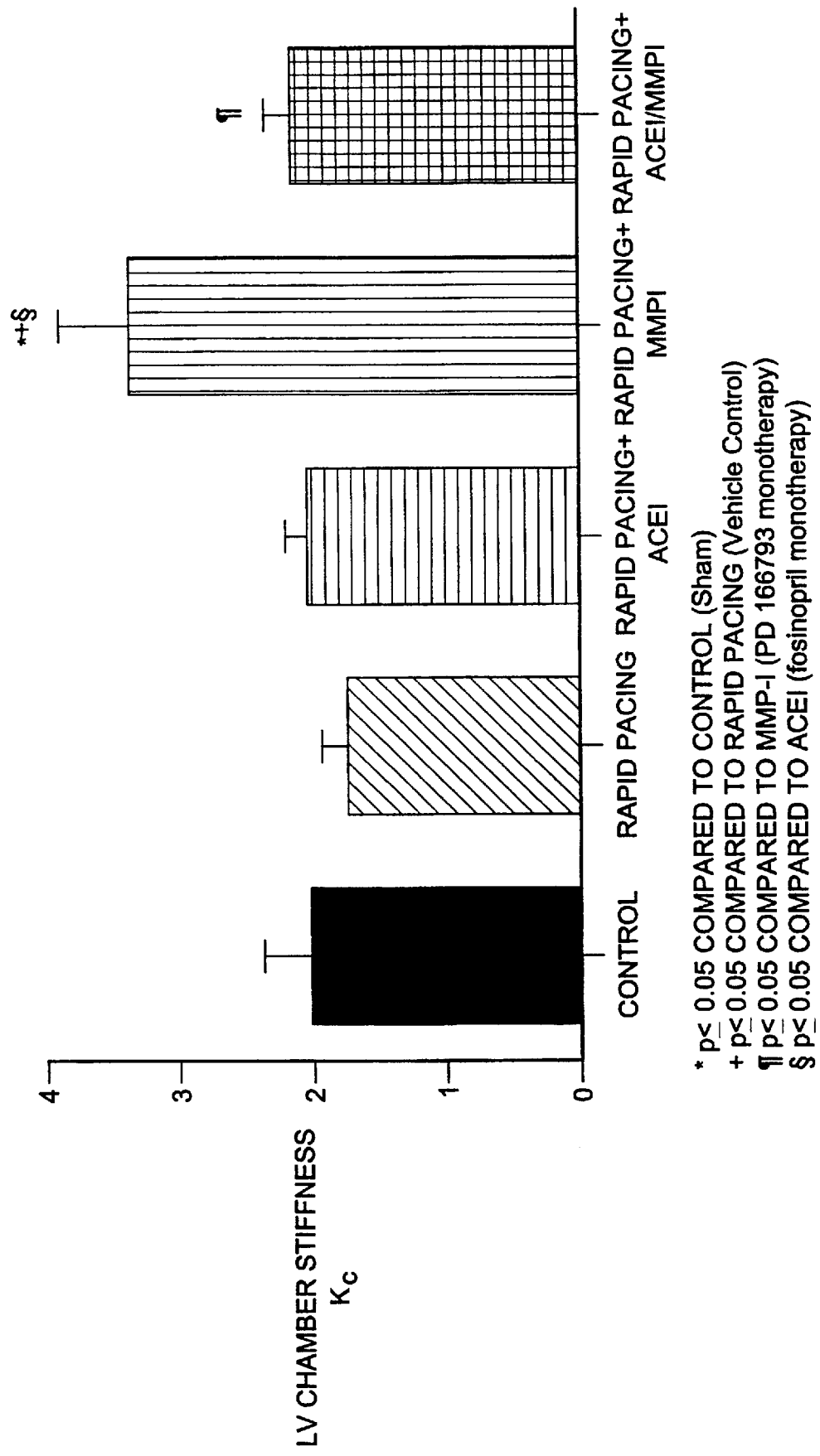

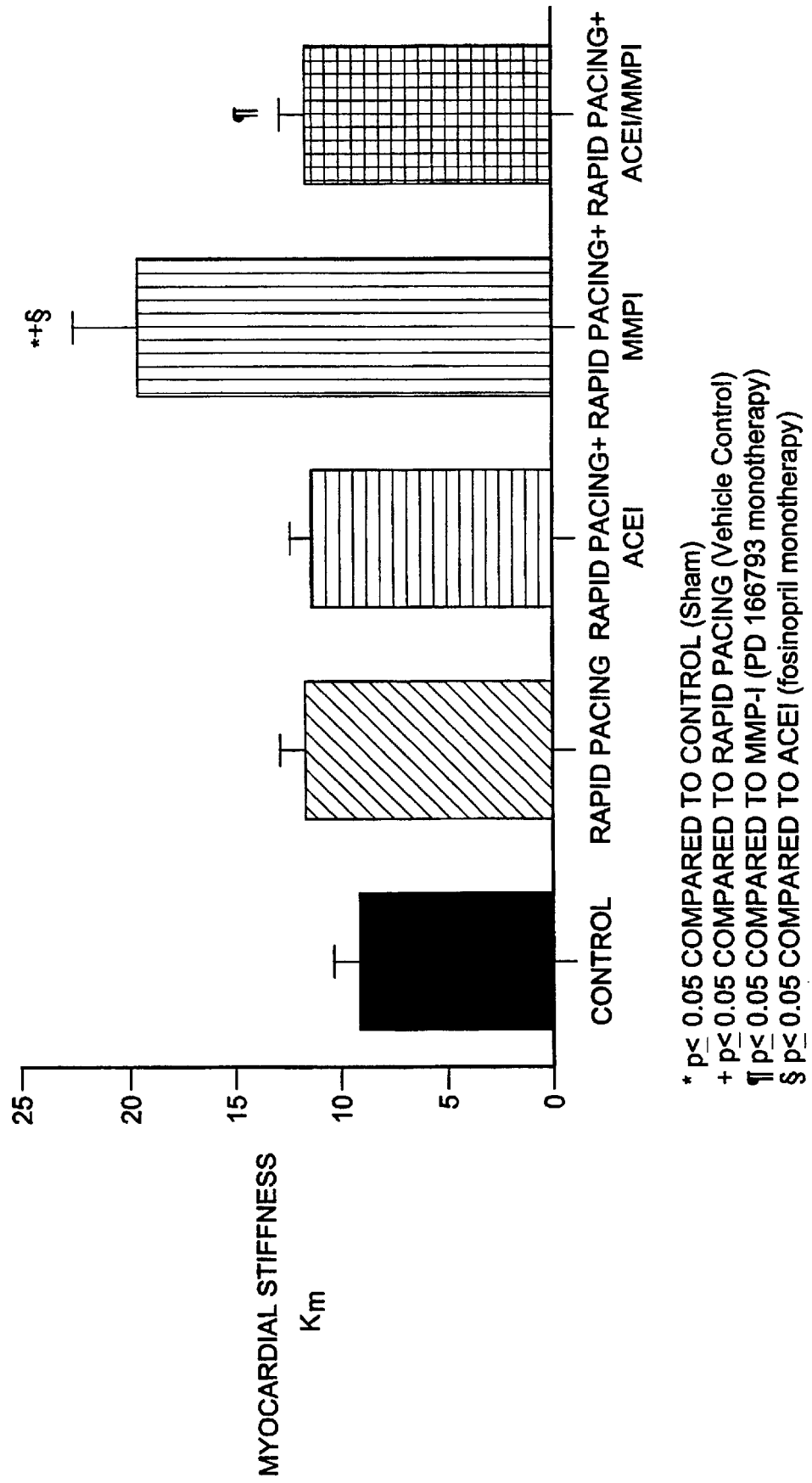

ACE INHIBITOR-MMP INHIBITOR COMBINATIONS

This application of a 371 of PCT/US98/23993 filed Nov. 10, 1998 which claims benefit of Ser. No. 60/068,594 filed Dec. 23, 1997.

FIELD OF THE INVENTION

This invention relates to compositions comprising a compound which inhibits the actions of angiotensin-converting enzyme and a compound which inhibits the actions of matrix metalloproteinase enzymes, and the use of such compositions for treating ventricular dilation, heart failure, and cardiovascular fibrotic pathologies.

BACKGROUND OF THE INVENTION

Fibrosis, the formation of excessive amounts of fibrotic or scar tissue, is a common pathologic problem in medicine. Scar tissue occludes arteries, immobilizes joints and damages internal organs, wreaking havoc on the body's ability to maintain vital functions. Every year, about 1.3 million people are hospitalized due to the damaging effects of organ fibrosis, yet doctors have few specific therapeutics to mollifies, let alone control the progressive onslaught of this condition. As a result, they often see patients disabled or killed by failing organs, circulatory insufficiency, or immobile joints infiltrated with ever increasing fibrosis and scar.

Fibrosis can follow surgery in the form of adhesions, keloid tumors, or hypertrophic (very severe) scarring. Fibrosis causes contractures and joint dislocation following severe burns, wounds, or orthopaedic injuries; it can occur in any organ is the sequelae to many disease states, such as hepatitis (liver cirrhosis), hypertension (heart failure), tuberculosis (pulmonary fibrosis), scleroderma (fibrotic skin and internal organs), diabetes (nephropathy), and atherosclerosis (fibrotic blood vessels).

Ironically, the very process designed to repair the body (ie, deposition of scar) can lead to dangerous complications. Like epoxy, scar tissue serves only a structural role. It fills in the gaps, but cannot contribute to the function of the organ in which it appears. For example, as fibrotic scar tissue replaces heart muscle damaged by hypertension, the heart becomes less elastic and thus less able to do its job. Similarly, pulmonary fibrosis causes the lungs to stiffen and decrease in size, a condition that can become life-threatening when oxygen uptake is impeded by fibrosis. Fibrotic growth can also proliferate and invade the healthy tissue that surrounds it even after the original injury heals. Too much scar tissue thus causes physiological roadblocks that disable, cripple, or kill.

In most cases, fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

One treatment approach, therefore, has been to target the early inflammatory response. Treatment with topical or systemic corticosteroids has achieved limited success, if used early in fibrosis. However, steroid therapy has little or no effect once scar tissue has already been deposited. Furthermore, prolonged administration of hydrocortisone, in pulmonary fibrotic disease for example, may actually worsen the condition, and at the same time cause cataracts and osteoporosis.

The second approach involves slowing the proliferation of those cells responsible for the increased collagen synthesis. Generally, this involves fibroblast cells, except in the vasculature where smooth muscle cells are responsible for collagen deposition. Compounds that have been used to inhibit fibroblast proliferation include benzoic hydrazide, as taught by U.S. Pat. No. 5,376,660. Benzoic hydrazide has been shown to suppress collagen synthesis and fibroblast proliferation, at least in tissue culture cells. U.S. Pat. No. 5,358,959 teaches the use of imidazole derivatives to inhibit the growth of fibroblasts by blocking the calcium-activated potassium channel. This particular agent also inhibits the proliferation of endothelial cells and vascular smooth muscle cells.

Likewise, a number of agents which affect smooth muscle cell proliferation have been tested. These compositions have included heparin, coumarin, aspirin, fish oils, calcium antagonists, steroids, prostacyclin, rapamycin, dipyridamole, ultraviolet irradiation, gamma ($\gamma$)-interferon, serotonin inhibitors, methotrexate and mycophenolic acid, either alone or in various combinations.

The final treatment strategy involves directly influencing the metabolism of collagen and the other components of fibrotic tissue. Thus, drugs that interfere with the biosynthesis, accumulation and catabolism of collagen have been used in the treatment of fibrosis. Many drugs are used to inhibit collagen synthesis, including derivatives of pyridone, alkadiene, benzoquinone, pyridine, oxalylamino acid and proline analogs. However, all of these drugs suffer from the drawback of also inhibiting the normal, and required synthesis of collagen as they antagonize the detrimental synthesis that occurs during fibrosis.

One of the most important pathologies for which fibrosis is a contributing factor is cardiovascular disease. Cardiovascular disease is the leading cause of death in the Western world. In the US it accounted for 930,000 deaths in 1990. There are an estimated 1.5 million heart attacks per year in the US that result in more than 500,000 deaths annually.

One consequence of heart disease is activation of the body's renin-angiotensin-aldosterone system (RAAS). The RAAS system maintains normal fluid volume in the body. The sympathetic nervous system provokes the release of the renin from the kidneys. The release of renin is stimulated by decreased extracellular fluid volume, low renal perfusion, and decreased sodium content in the macula densa. Renin is a proteolytic enzyme that acts on angiotensinogen to produce the decapeptide angiotensin I. Angiotensin I is then converted to the octapeptide angiotensin II (AII) by the action of angiotensin-converting enzyme (ACE). AII is a potent pressor agent producing a rapid elevation in blood pressure.

AII also is a growth factor and plays a role in proliferation of smooth muscle cells.

We have now discovered that compounds which inhibit ACE can be used in conjunction with compounds which inhibit one or more matrix metalloproteinase (MMP) enzymes to achieve surprisingly good results in treating fibrosis and related cardiovascular diseases like ventricular dilation and heart failure.

SUMMARY OF THE INVENTION

This invention provides a composition comprised of an ACE inhibitor and an MMP-inhibitor. In a preferred embodiment, the ACE inhibitor is selected from captopril, enalapril, enalaprilat, lisinopril, ramipril, zofenopril, ceroanapril, alacepril, benazepril, delapril, pentopril, quinapril, quinaprilat, moexipril, rentiapril, quinapril, spirapril, cilazapril, perindopril, and fosinopril.

The MMP inhibitor to be employed is any chemical compound that is effective in inhibiting the biological activity of a matrix metalloproteinase such as collagenase, stromelysin, gelatinase or elastase. Numerous compounds are known to be matrix metalloproteinase inhibitors, and any of such compounds can be utilized in the composition of this invention.

In a preferred embodiment, the matrix metalloproteinase inhibitor to be utilized is a substituted bicyclic compound of the formula

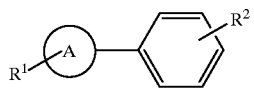

wherein:

A is phenyl

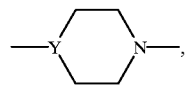

where Y is CH or N;

$R^1$ is a substituent such as alkyl, aryl, halo, amino, substituted and disubstituted amino, and alkoxy;

$R^2$ is carboxyalkyl ketone or oxime, or a carboxyalkyl sulfonamide such as

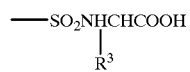

where $R^3$ is alkyl, substituted alkyl, amino, substituted and disubstituted amino, and aryl. Preferred alkyl and alkoxy groups are $C_1$–$C_{10}$ alkyl and $C_1$–$C_{10}$ alkoxy, which can be straight chain or branched, and optionally substituted by halo, amino, nitro, carboxy, hydroxy, aryl, and heteroaryl.

A particularly preferred embodiment is a composition comprising a biphenylsulfonamide (compounds of the above formula when A is phenyl) such as

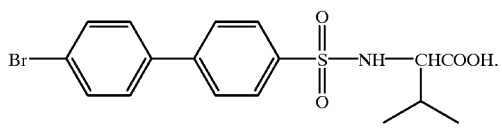

In another embodiment, the matrix metalloproteinase inhibitor is a substituted fused tricyclic compound of the formula

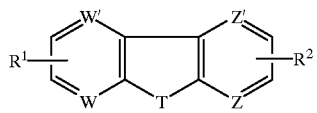

where $R^1$ and $R^2$ are as defined above, T is O, $CH_2$, SQ $(O)_{0,1\ or\ 2,}$ C=O, $NR^3$, or

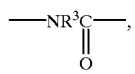

and W, $W^1$, Z, and $Z^1$ are each the same or different and each is $CR^3$, where $R^3$ is alkyl, halo, alkoxy, acyl, and aryl. A preferred composition utilizes dibenzofurans and fluorenes of the above formula, for instance compounds such as

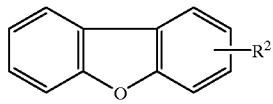

and

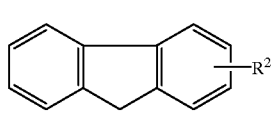

where $R^2$ is, for instance,

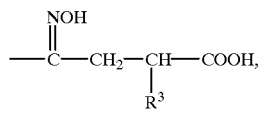

or

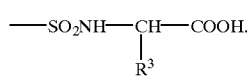

All of the matrix metalloproteinase inhibitors to be utilized in the composition of this invention are either known or are readily available by common synthetic processes.

The invention also provides a method for treating cardiovascular fibrosis, ventricular dilation, and heart failure by administering to a mammal in need of treatment an effective amount of the combination of an ACE inhibitor and an MMP inhibitor.

BRIEF DESCRIPTION OF FIGURES

FIG. 1 shows the rate of mortality in spontaneously hypertensive heart failure (SHHF) rats receiving no drug, quinapril (Q) alone, Compound 166793 (793) alone, and the combination of Q together with 793.

FIG. 3 shows that systolic function, measured as preload recruitable stroke work (PRSW) is reduced in all groups of rapid-paced pigs (relative to shown control), and that fosinopril monotherapy improved systolic function to the greatest extent.

FIGS. 5a–b show the effects of drug treatment on LV chamber stiffness and myocardial stiffness relative to untreated rapid-paced pigs. Treatment with MMP inhibitor 166793 alone increased both LV chamber stiffness and myocardial stiffness, whereas coadministration with an ACE-inhibitor (fosinopril) caused a normalization of both stiffness parameters.

DETAILED DESCRIPTION OF THE INVENTION

Figure 2A:
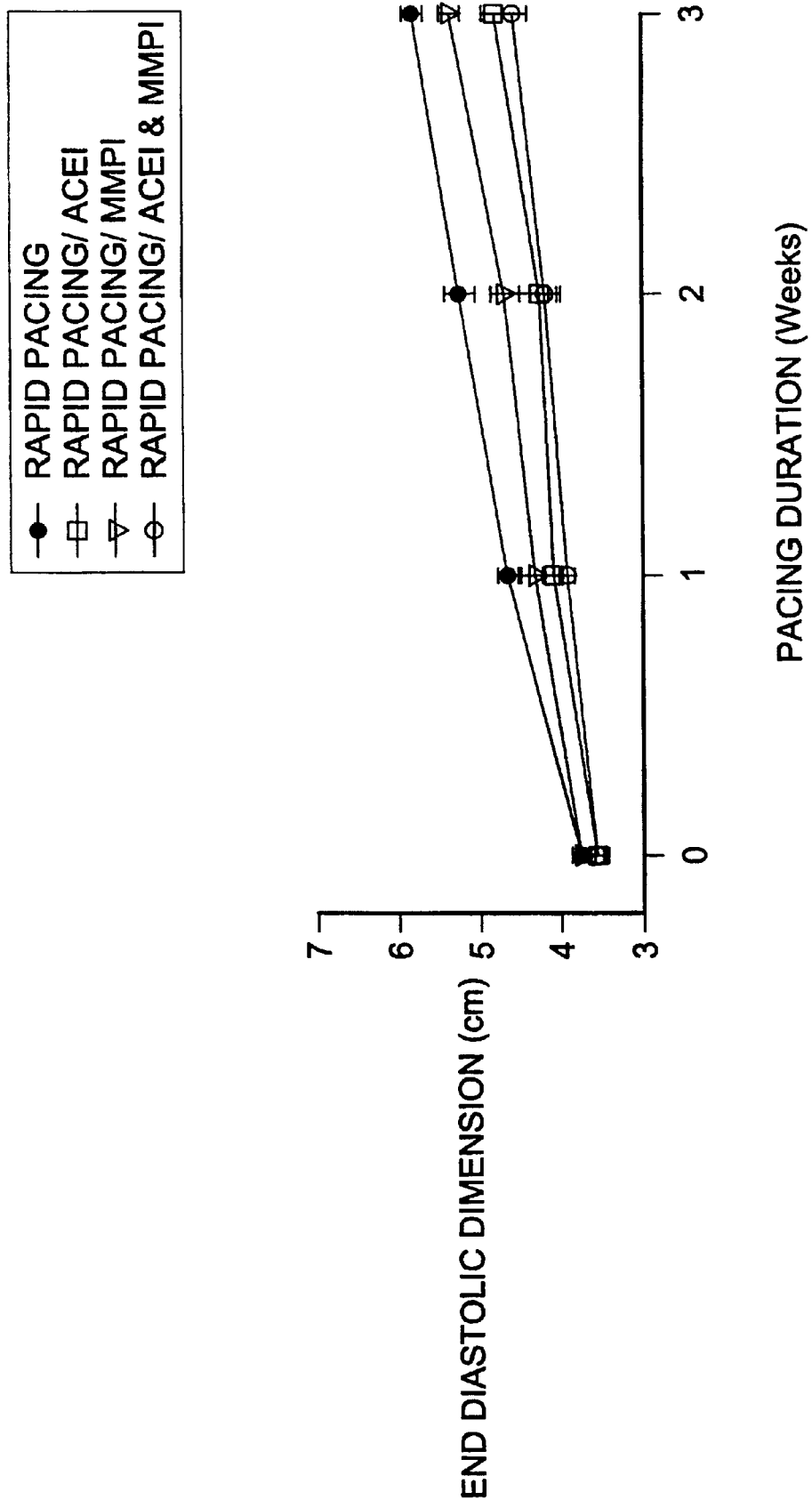
FIGS. 2a–c show the echocardiographic measurements of left ventricular (LV) dilation and function in pigs subjected to rapid pacing in order to induce heart failure conditions. Both fosinopril and 166793 individually reduce wall stress and end diastolic dimension, but the combination therapy caused a much greater effect.

A "matrix metalloproteinase inhibitor" as used herein is any chemical compound that inhibits by at least five percent the hydrolytic activity of at least one matrix metalloproteinase enzyme that is naturally occurring in a mammal. Such compounds are also referred to as "MMP inhibitors". Numerous matrix metalloproteinase inhibitors are known, and all are useful in the method of this invention. For example, 4-biarylbutyric and 5-biarylpentanoic acid derivatives are described in WO 96/15096, which is incorporated herein by reference. The compounds are defined generally as $(T)_x$-A-B-D-E-G. Over 400 specific compounds are named, and each is incorporated herein and can be employed in this invention. Especially preferred compounds to be utilized include the following:

[1,1'-Biphenyl]-4-butanoic acid, 4'-chloro-α-(2-methylpropyl)-γ-oxo-;
[1,1'-Biphenyl]-4-butanoic acid, 4'-chloro-α-(2-methylpropyl)-γ-oxo-, (S)-;
[1,1'-Biphenyl]-4-butanoic acid, 4'-chloro-α-(2-methylpropyl)-γ-oxo-, (R)-
[1,1'-Biphenyl]-4-butanoic acid, 4'-chloro-β-(2-methylpropyl)-γ-oxo-, (S);
[1,1'-Biphenyl]-4-butanoic acid, 4'-chloro-β-(2-methylpropyl)-γ-oxo-, (R)-;
[1,1'-Biphenyl]-4-butanoic acid, 4'-chloro-γ-oxo-;
[1,1'-Biphenyl]-4-butanoic acid, 4'-bromo-γ-oxo-;
[1,1'-Biphenyl]-4-butanoic acid, 4'-fluoro-γ-oxo-;
[1,1'-Biphenyl]-4-butanoic acid, 2'-fluoro-γ-oxo-;
[1,1'-Biphenyl]-4-butanoic acid, 2'-chloro-γ-oxo-;
[1,1'-Biphenyl]-4-butanoic acid, 2',4'-difluoro-γ-oxo-;
[1,1'-Biphenyl]-4-butanoic acid, 3'-chloro-γ-oxo-;
[1,1'-Biphenyl]-4-butanoic acid, α-(2-methyl-propyl)-γ-oxo-;
[1,1'-Biphenyl]-4-butanoic acid, 4'-bromo-α-(2-methypropyl)-γ-oxo-;
[1,1'-Biphenyl]-4-butanoic acid, 4'-fluoro-α-(2-methylpropyl)-γ-oxo-;
[1,1'-Biphenyl]-4-butanoic acid, 4'-ethyl-α-(2-methylpropyl)-γ-oxo-;
[1,1'-Biphenyl]-4-butanoic acid, 2'-fluoro-α-(2-methylpropyl)-γ-oxo-;
[1,1'-Biphenyl]-4-butanoic acid, 2'-chloro-α-(2-methylpropyl)-γ-oxo-;
[1,1'-Biphenyl]-4-butanoic acid, 4'-methoxy-α-(2-methylpropyl)-γ-oxo-;
[1,1'-Biphenyl]-4-butanoic acid, 2',4'-difluoro-α-(2-methylpropyl)-γ-oxo-;
[1,1'-Biphenyl]-4-butanoic acid, 4'-methyl-α-(2-methylpropyl)-γ-oxo-;
[1,1'-Biphenyl]-4-butanoic acid, α-(2-methyl-propyl)-γ-oxo-4'-pentyl-;
[1,1'-Biphenyl]-4-butanoic acid, 4'-chloro-α-methylene-γ-oxo-;
[1,1'-Biphenyl]-4-butanoic acid, 2'-chloro-α-methylene-γ-oxo-;
[1,1'-Biphenyl]-4-butanoic acid, 4'-chloro-α-methyl-γ-oxo-;
[1,1'-Biphenyl]-4-butanoic acid, 4'-chloro-γ-oxo-α-pentyl-;
Benzenebutanoic acid, 4-chloro-α-(2-methylpropyl)-γ-oxo-;
Benzenebutanoic acid, 4-methyl-α-methylene-γ-oxo-;
2-Butenoic acid, 4-(4'-chloro[1,1'-biphenyl]-4-yl)-4-oxo-, (E)-;
2-Butenoic acid, 4-[4-(4-chlorophenyoxy)-phenyl]-4-oxo, (E)-;
[1,1'-Biphenyl]-4-butanoic acid, 4'-hydroxy-α-(2-methylpropyl)-γ-oxo-;
[1,1'-Biphenyl-4-butanoic acid, 4'-chloro-β-methyenle-γ-oxo-;
[1,1'-Biphenyl]-4-butanoic acid, 4'-chloro-γ-hydroxy-α-(2-methyl propyl )-;
[1,1'-Biphenyl]-4-butanoic acid, 4'-chloro-γ-hydroxy-α-(2-methylpropyl)-;
2(3H)-Furanone, 5-(4'-chloro[1,1'-biphenyl]-4-yl)dihydro-3-(2-methylpropyl)-;
2(3H)-Furanone, 5-(4'-chloro[1,1'-biphenyl]-4-yl)dihydro-3-(2-methylpropyl)-;
[1,1'-Biphenyl]-4-butanoic acid, 3',4'-dichloro-γ-oxo-α-(3-phenylpropyl)-;
[1,1'-Biphenyl]-4-butanoic acid, 3',5'-dichloro-γ-oxo-α-(3-phenylpropyl)-;
[1,1'-Biphenyl]-4-butanoic acid, 4'-(acetyloxy)-γ-oxo-α-(3-phenylpropyl)-;
Benzenepentanoic acid, α-[2-[4-(5-chloro-2-thienyl)phenyl]-2-oxoethyl]-;
2-Furancarboxylic acid, 5-[4-(3-carboxy-1-oxo-6-phenylhexyl)phenyl]-;
Benzenepentanoic acid, α-[2-oxo-2-[4-(3-pyridinyl)phenyl]ethyl]-;
Benzenepentanoic acid, α-[2-oxo-2-[4-[6-(pentyloxy)-3-pyridinyl]phenyl]ethyl]-;
[1,1'-Biphenyl]-4-butanoic acid, γ-oxo-4'-(pentylthio)-α-(3-phenylpropyl)-;
[11'-Biphenyl]-4-butanoic acid, 4'-methoxy-γ-oxo-α-(3-phenylpropyl)-;
[1,1'-Biphenyl]-4-butanoic acid, 3'-chloro-4'-fluoro-γ-oxo-α-(3-phenylpropyl)-;
[1,1'-Biphenyl]-4-butanoic acid, 4'-ethoxy-γ-oxo-α-(3-phenylpropyl)-;
Benzenepentanoic acid, α-[2-oxo-2-[4-(3-thienyl)phenyl]ethyl]-;
[1,1'-Biphenyl]-4-butanoic acid, 2',4'-dichloro-γ-oxo-α-(3-phenylpropyl)-;
[1,1'-Biphenyl]-4-butanoic acid, 4'-formyl-γ-oxo-α-(3-phenylpropyl)-;
[1,1'-Biphenyl]-4-butanoic acid, γ-oxo-α-(3-phenylpropyl)-3',5'-bis(trifluoromethyl)-;
Benzenepentanoic acid, α-[2-oxo-2-[4-(2-thienyl)phenyl]ethyl)-;
[1,1'-Biphenyl]-4-butanoic acid, γ-oxo-α-(3-phenylpropyl)-3'-(trifluoromethyl)-;
[1,1'-Biphenyl]-4-butanoic acid, 2'-formyl-γ-oxo-α-(3-phenylpropyl)-;
[1,1'-Biphenyl]-4-butanoic acid, 4-hydroxy-γ-oxo-α-(3-phenylpropyl)-;
[1,1'-Biphenyl]-4-butanoic acid, γ-oxo-α-(3-phenylpropyl)-4'-propoxy-;
[1,1'-Biphenyl]-4-butanoic acid, γ-oxo-4'-(pentyloxy)-α-(3-phenylpropyl)-;
[1,1'-Biphenyl]-4-butanoic acid, γ-oxo-4'-(pentyloxy)-α-(3-phenylpropyl)-, (S)-;
[1,1'-Biphenyl]-4-butanoic acid, γ-oxo-4'-(pentyloxy)-α-(3-phenylpropyl)-, (R)-;
[1,1'-Biphenyl]-4-butanoic acid, 4'-(hexyloxy)-γ-oxo-α-(3-phenylpropyl)-;
[1,1'-Biphenyl]-4-butanoic acid, 4'-butoxy-γ-oxo-α-(3-phenylpropyl)-;
[1,1'-Biphenyl]-4-butanoic acid, γ-oxo-4'-(3-phenylpropoxy)-α-(3-phenylpropyl)-;

[1,1'-Biphenyl]-4-butanoic acid, 4'-(1-methylethoxy)-γ-oxo-α-(3-phenylpropyl)-;
[1,1'-Biphenyl]-4-butanoic acid, 4'-(heptyloxy)-γ-oxo-α-(3-phenylpropyl)-;
[1,1'-Biphenyl]-4-butanoic acid, 4'-(cyclohexylmethoxy)-γ-oxo-α-(3-phenylpropyl)-;
[1,1'-Biphenyl]-4-butanoic acid, 4'-(2-methyl-propoxy)-γ-oxo-α-(3-phenylpropyl)-;
[1,1'-Biphenyl]-4-butanoic acid, γ-oxo-α-(3-phenylpropyl)-4'-(2-propenyloxy)-;
[1,1'-Biphenyl]-4-butanoic acid, 4'-chloro-α-heptyl-γ-oxo-;
[1,1'-Biphenyl]-4-butanoic acid, 4'-chloro-α-decyl-γ-oxo-;
[1,1'-Biphenyl]-4-butanoic acid, 4'-nitro-γ-oxo-α-(2-phenylethyl)-;
[1,1'-Biphenyl]-4-butanoic acid, 4'-cyano-γ-oxo-α-(2-phenylethyl)-;
[1,1'-Biphenyl]-4-butanoic acid, 4'-chloro-α-[2-(2-iodophenyl)ethyl]-γ-oxo-;
[1,1'-Biphenyl]-4-butanoic acid, 4'-chloro-α-[2-(3-iodophenyl)ethyl]-γ-oxo-;
[1,1'-Biphenyl]-4-butanoic acid, 4'-chloro-α-[2-(4-iodophenyl)ethyl]-γ-oxo-;
[1,1'-Biphenyl]-4-butanoic acid, 4'-chloro-α-[2-(3,5-dimethoxyphenyl)ethyl]-γ-oxo-;
[1,1'-Biphenyl]-4-butanoic acid, 4'-chloro-γ-oxo-α-phenyl-;
[1,1'-Biphenyl]-4-butanoic acid, 4'-chloro-γ-oxo-α-(phenylmethyl)-;
[1,1'-Biphenyl]-4-butanoic acid, 4'-chloro-γ-oxo-α-(2-phenylmethyl)-;
[1,1'-Biphenyl]-4-butanoic acid, 4'-chloro-γ-oxo-α-[(trimethylsilyl)methyl]-;
[1,1'-Biphenyl]-4-butanoic acid, 4'-bromo-γ-oxo-α-(3-phenylpropyl)-;
[1,1'-Biphenyl]-4-butanoic acid, -γ-oxo-α-(3-phenylpropyl)-;
[1,1'-Biphenyl]-4-butanoic acid, 4'-amino-γ-oxo-α-(2-phenylethyl)-;
[1,1'-Biphenyl]-4-butanoic acid, γ-oxo-α-(2-phenylethyl)-4'-[[(phenylmethoxy)carbonyl]amino]-;
[1,1'-Biphenyl]-4-butanoic acid, 4'-[[(1,1-dimethylethoxy)carbonyl]amino]-γ-oxo-α-(2-phenylethyl)-;
[1,1'-Biphenyl]-4-butanoic acid, 4'-(acetylamino) γ-oxo-α-(2-phenylethyl)-;
[1,1'-Biphenyl]-4-butanoic acid, γ-oxo-4'-[(1-oxopentyl)amino]-α-(2-phenylethyl)-;
[1,1'-Biphenyl]-4-butanoic acid, 4'-[(3,3-dimethyl-1-oxobutyl)amino]-γ-oxo-α-(2-phenylethyl)-;
[1,1'-Biphenyl]-4-butanoic acid, 4'-chloro-α-[2-[2-(methoxycarbonyl)phenyl]ethyl]-γ-oxo-;
[1,1'-Biphenyl]-4-butanoic acid, α-[2-(2-carboxyphenyl)ethyl]-4'-chloro-γ-oxo-;
[1,1'-Biphenyl]-4-butanoic acid, 4'-chloro-α-[2-[2-[(diethylamino)carbonyl]phenyl]ethyl]-γ-oxo-;
[1,1'-Biphenyl]-4-butanoic acid, 4'-chloro-α-[2-[3-[(diethylamino)carbonyl]phenyl]ethyl]-γ-oxo-, (S)-;
[1,1'-Biphenyl]-4-butanoic acid, 4'-chloro-α-[2-[3-[(diethylamino)carbonyl]phenyl]ethyl]-γ-oxo-, (R)-;
Cyclopentanecarboxylic acid, 2-[(4'-chloro[1,1'-biphenyl]-4-yl)carbonyl]-5-[(phenylmethyl)methyl]-, (1α,2β,5β)-;
Cyclopentanecarboxylic acid, 2-[(4'-chloro[1,1'-biphenyl]-4-yl)carbonyl]-5-(phenoxymethyl)-, (1α,2β,5β)-;
Cyclopentanecarboxylic acid, 2-[(benzoyloxy)-methyl]-5-[(4'-chloro[1,1'-biphenyl]-4-yl)carbonyl]-, (1α,2β,5β)-;
1,2-Benzenedicarboxylic acid, 1-[[2-carboxy-3-[(4'-chloro[1,1'-biphenyl]-4-yl)carbonyl]cyclopentyl]-methyl]-2-methyl ester,(1α,2β,3α)-;
Cyclopentanecarboxylic acid, 2-[(4'-chloro[1,1'-biphenyl]-4-yl)carbonyl]-5-[(2-thienylthio)methyl]-, (1α,2β,5β)-;
Cyclopentanecarboxylic acid, 2-[(benzoylamino)methyl]-5-[(4'-chloro[1,1'-biphenyl]-4-yl)carbonyl]-, (1α,2β,5β)-;
Cyclopentanecarboxylic acid, 2-[(4'-chloro[1,1'-biphenyl]-4-yl)carbonyl]-5-[[(2-methoxyethoxy)methoxy]methyl]-, (1α,2β,5β)-;
Cyclopentanecarboxylic acid, 2-[(4'-chloro[1,1'-biphenyl)-4-yl)carbonyl]-5-[[(phenylmethyl)thio]methyl]-, (1α,2γ,5β)-;
Cyclopentanecarboxylic acid, 2-[(4'-chloro[1,1'-biphenyl]-4-yl)carbonyl]-5-[(phenylthio)methyl]-, (1α,2β,5β)-;
Cyclopentanecarboxylic acid, 2-[(4'-chloro[1,1'-biphenyl]-4-yl)carbonyl]-5-[(propylthio)methyl]-, (1α,2β,5β)-;
Cyclopentanecarboxylic acid, 2-[(2-benzothiazolylthio)methyl]-5-[(4'-chloro[1,1'-biphenyl]-4-yl)carbonyl]-, (1α,2β,5β)-;
Benzoic acid, 2-[[[2-carboxy-3-[(4'-chloro[1,1'-biphenyl]-4-yl)carbonyl]cyclopentyl]methyl]thio]-, 1-methyl ester, (1α,2β,3α)-;
Cyclopentanecarboxylic acid, 2-[(4'-chloro[1,1'-biphenyl]-4-yl)carbonyl]-5-[[[(phenylmethoxy)carbonyl]-amino]methyl]-, (1α,2β,5β)-;
Benzoic acid, 2-methyl-, [2-carboxy-3-[(4'-chloro[1,1'-biphenyl]-4-yl)carbonyl]cyclopentyl]methyl ester, (1α, 2β,3α)-;
Benzoic acid, 3-methyl-, [2-carboxy-3-[(4'-chloro[1,1'-biphenyl]-4-yl)carbonyl]cyclopentyl]methyl ester, (1α, 2β,3α)-;
Benzoic acid, 4-methyl-, [2-carboxy-3-[(4'-chloro[1,1'-biphenyl]-4-yl)carbonyl]cyclopentyl]methyl ester, (1α, 2β,3α)-;
Benzoic acid, 2-methoxy-, [2-carboxy-3-[(4'-chloro[1,1'-biphenyl]-4-yl)carbonyl]cyclopentyl]methyl ester, (1α, 2β,3α)-;
Benzoic acid, 3-methoxy-, [2-carboxy-3-[(4'-chloro[1,1'-biphenyl]-4-yl)carbonyl]cyclopentyl]methyl ester, (1',2β, 3α)-;
Benzoic acid, 4-methoxy-, [2-carboxy-3-[(4'-chloro[1,1'-biphenyl]-4-yl)carbonyl]cyclopentyl]methyl ester, (1α, 2β,3α)-;
Cyclopentanecarboxylic acid, 2-[(2-benzoxazolylthio)methyl]-5-[(4'-chloro[1,1'-biphenyl]-4-yl)carbonyl]-, (1α,2β,5β)-;
Cyclopentanecarboxylic acid, 2-[(4'-chloro[1,1'-biphenyl]-4-yl)carbonyl]-5-[(1,3-dihydro-4-nitro-1,3-dioxo-2H-isoindol-2-yl)methyl]-, (1α,2β,5β)-;
Cyclopentanecarboxylic acid, 2-[(4'-chloro[1,1'-biphenyl]-4-yl)carbonyl]-5-[(1,3-dihydro-5-nitro-1,3-dioxo-2H-isoindol-2-yl)methyl]-, (1α,2β,5β)-;
2H-Benz[ƒ]isoindole-2-butanoic acid, α-[2-(4'-ethoxy[1,1'-biphenyl]-4-yl)-2-oxoethyl]-1,3-dihydro-1,3-dioxo-;
[1,1'-Biphenyl]-4-butanoic acid, α-(acetylamino)-4'-chloro-γ-oxo-;
2H-Isoindole-2-hexanoic acid, α-[2-(4'-chloro[1,1'-biphenyl]-4-yl)-2-oxoethyl]-1,3-dihydro-1,3-dioxo-;
[1,1'-Biphenyl]-4-butanoic acid, 4'-chloro-α-[[[3-(methoxycarbonyl)phenyl]thio]methyl]-γ-oxo-;
[1,1'-Biphenyl]-4-butanoic acid, 4'-chloro-α-[[(2,6-dimethylphenyl)thio]methyl]-γ-oxo-;
[1,1'-Biphenyl]-4-butanoic acid, 4'-chloro-α-[[[4-fluoro-2-(methoxycarbonyl)phenyl]thio]methyl]-γ-oxo-;
[1,1'-Biphenyl]-4-butanoic acid, 4'-chloro-α-[[[3-[(diethylamino)carbonyl]phenyl]thio]methyl]-γ-oxo-;
[1,1'-Biphenyl]-4-butanoic acid, 4'-chloro-α-[[[2-[(dimethylamino)carbonyl]phenyl]thio]methyl]-γ-oxo-;
[1,1'-Biphenyl]-4-butanoic acid, 4'-chloro-α-[[[3-[(dimethylamino)carbonyl]phenyl]thio]methyl-]γ-oxo-;

Bicyclo[2.2.1]hept-5-ene-2-carboxylic acid, 3-[[4'-(pentyloxy)[1,1'-biphenyl]-4-yl]carbonyl]-, (2-endo,3-exo)-;
1-Cyclopentene-1-carboxylic acid, 5-[(4'-chloro[1,1'-biphenyl]-4-yl)carbonyl]-;
Cyclopentanecarboxylic acid, 2-[(4'-chloro[1,1'-biphenyl]-4-yl)carbonyl]-5-[(phenylmethyl)thio]-, (1α,2β,5α)-;
Cyclopentanecarboxylic acid, 2-[(4'-chloro[1,1'-biphenyl-4-yl)carbonyl]-5-[(phenylmethyl)thio]-, (1α,2β,5β)-;
1-Cyclopentene-1-carboxylic acid, 5-[[4'-(pentyloxy)[1,1'-biphenyl]-4-yl]carbonyl)-;
1-Cyclopentene-1-carboxylic acid, 5-[[4'-(hexyloxy)[1,1'-biphenyl-4-yl)]carbonyl]-;
[1,1'-Biphenyl]-4-butanoic acid, 4'-hydroxy-γ-oxo-α-[(phenylthio)methyl]-;
[1,1'-Biphenyl]-4-butanoic acid, α-[_2-[(butylamino)carbonyl]phenyl]ethyl]-4'-chloro-γ-oxo-;
[1,1'-Biphenyl]-4-butanoic acid, α-[2-(3-carboxyphenyl)ethyl]-4'-chloro-γ-oxo-;
[1,1'-Biphenyl]-4-butanoic acid, 4'-chloro-α-[2-[3-(diethylamino)carbonyl]phenyl]ethyl]-γ-oxo-;
[1,1'-Biphenyl]-4-butanoic acid, α-[2-[3-[(butylamino)carbonyl]phenyl]ethyl]-4'-chloro-γ-oxo-;
[1,1'-Biphenyl]-4-butanoic acid, 4'-chloro-α-[2-[4-[(diethylamino)carbonyl]phenyl]ethyl]-γ-oxo-;
[1,1'-Biphenyl]-4-butanoic acid, α-[2-[4-[(butylamino)carbonyl]phenyl]ethyl]-4'-chloro-γ-oxo-;
[1,1'-Biphenyl]-4-butanoic acid, α-[2-(4-carboxyphenyl)ethyl]-4'-chloro-γ-oxo-;
[1,1'-Biphenyl]-4-butanoic acid, 4'-methoxy-γ-oxo-α-(2-phenylethyl)-;
[1,1'-Biphenyl]-4-butanoic acid, 4'-hydroxy-γ-oxo-α-(2-phenylethyl)-;
[1,1'-Biphenyl]-4-butanoic acid, 4'-ethoxy-γ-oxo-α-(2-phenylethyl)-;
[1,1'-Biphenyl]-4-butanoic acid, γ-oxo-α-(2-phenylethyl)-4'-propoxy-;
[1,1'-Biphenyl]-4-butanoic acid, γ-oxo-4'-(pentyloxy)-α-(2-phenylethyl)-;
[1,1'-Biphenyl]-4-butanoic acid, 4'-(hexyloxy)-γ-oxo-α-(2-phenylethyl)-;
[1,1'-Biphenyl]-4-butanoic acid, 4'-butoxy-γ-oxo-α-(2-phenylethyl)-;
[1,1'-Biphenyl]-4-butanoic acid, γ-oxo-α-(2-phenylethyl)-4'-(phenylmethoxy)-;
[1,1'-Biphenyl]-4-butanoic acid, α-[2-(3-iodophenyl)ethy]-γ-oxo-4'-(pentyloxy)-;
[1,1'-Biphenyl]-4-butanoic acid, α-[2-(3-iodophenyl)ethyl]-γ-oxo-4'-(phenylmethoxy)-;
[1,1'-Biphenyl]-4-butanoic acid, α-[2-(3-[(diethylamino)carbonyl]phenyl]ethyl]-γ-oxo-4'-(pentyloxy)-;
[1,1'-Biphenyl]-4-butanoic acid, α-[2-(3-[(diethylamino)carbonyl]phenyl]ethyl]-γ-oxo-4'-(phenylmethoxy)-;
1,2-Pyrrolidinedicarboxylic acid, 3-[(4'-chloro[1,1'-biphenyl]-4-yl)carbonyl]-, 1-(phenylmethyl) ester, (2S-trans)-;
1,2-Pyrrolidinedicarboxylic acid, 3-[(4'-chloro[1,1'-biphenyl]-4-yl)carbonyl]-, 1-(phenylmethyl) ester, (2'R-trans)-;
L-Proline, 3-[(4'-chloro[1,1'-biphenyl]-4-yl)carbonyl]-1-[[(phenylmethyl)amino]carbonyl)-, trans-;
L-Proline, 3-[(4'-chloro[1,1'-biphenyl]-4-yl)carbonyl]-1-(1-oxo-3-phenylpropyl)-, trans-;
L-Proline, 3-[(4'-chloro[1,1'-biphenyl]-4-yl)carbonyl]-1-(phenylacetyl)-, trans-;
L-Proline, 3-[(4'-chloro[1,1'-biphenyl]-4-yl)carbonyl]-1-(3,3-dimethyl-1-oxobutyl)-, trans-;
[1,1'-Biphenyl]-4-butanoic acid, 4'-chloro-α-heptyl-β-oxo-;
[1,1'-Biphenyl]-4-butanoic acid, 4'-chloro-α-decyl-β-oxo-;
[1,1'-Biphenyl]-4-butanoic acid, 4'-nitro-γ-oxo-α-(2-phenylethyl)-;
[1,1'-Biphenyl]-4-butanoic acid, 4'-cyano-γ-oxo-α-(2-phenylethyl)-;
[1,1'-Biphenyl]-4-butanoic acid, 4'-chloro-α-[2-(2-iodophenyl)ethyl]-γ-oxo-;
[1,1'-Biphenyl]-4-butanoic acid, 4'-chloro-α-[2-(3-iodophenyl)ethyl]-γ-oxo-;
[1,1'-Biphenyl]-4-butanoic acid, 4'-chloro-α-[2-(4-iodophenyl)ethyl]-γ-oxo-;
[1,1'-Biphenyl]-4-butanoic acid, 4'-chloro-α-[2-(3,5-dimethoxyphenyl)ethyl]-γ-oxo-;
[1,1'-Biphenyl]-4-butanoic acid, 4'-chloro-γ-oxo-α-phenyl-;
[1,1'-Biphenyl]-4-butanoic acid, 4'-chloro-γ-oxo-α-(phenylmethyl)-;
[1,1'-Biphenyl]-4-butanoic acid, 4'-chloro-γ-oxo-α-(2-phenylethyl)-;
[1,1'-Biphenyl]-4-butanoic acid, 4'-chloro-γ-oxo-α-[(trimethylsilyl)methyl]-;
[1,1'-Biphenyl]-4-butanoic acid, 4'-bromo-γ-oxo-α-(3-phenylpropyl)-;
[1,1'-Biphenyl]-4-butanoic acid, γ-oxo-α-(3-phenylpropyl)-;
[1,1'-Biphenyl]-4-butanoic acid, 4'-amino-γ-oxo-α-(2-phenylethyl)-;
[1,1'-Biphenyl]-4-butanoic acid, γ-oxo-α-(2-phenylethyl)-4'-[[(phenylmethoxy)carbonyl]amino]-;
[1,1'-Biphenyl]-4-butanoic acid, 4'-[[(1,1-dimethylethoxy)carbonyl]amino]-γ-oxo-α-(2-phenylethyl)-;
[1,1'-Biphenyl]-4-butanoic acid, 4'-(acetylamino)-γ-oxo-α-(2-phenylethyl)-;
[1,1'-Biphenyl]-4-butanoic acid, γ-oxo-4'-[(1-oxopentyl)amino]-α-(2-phenylethyl)-;
[1,1'-Biphenyl]-4-butanoic acid, 4'-[(3,3-dimethyl-1-oxobutyl)amino]-γ-oxo-α-(2-phenylethyl)-;
[1,1'-Biphenyl]-4-butanoic acid, 4'-chloro-α-[2-[2-methoxycarbonyl)phenyl]ethyl]-γ-oxo-;
[1,1'-Biphenyl]-4-butanoic acid, α-[2-(2-carboxyphenyl)ethyl]-4'-chloro-γ-oxo-;
[1,1'-Biphenyl]-4-butanoic acid, 4'-chloro-α-[2-[2-[(diethylamino)carbonyl]phenyl]ethyl]-γ-oxo-;
[1,1'-Biphenyl]-4-butanoic acid, 4'-chloro-α-[2-[3-[(diethylamino)carbonyl]phenyl]ethyl]-γ-oxo-, (S)-; and
[1,1'-Biphenyl]-4-butanoic acid, 4'-chloro-α-[2-[3-[(diethylamino)carbonyl]phenyl]ethyl]-γ-oxo-, (R)-.

Fenbufen and compounds related to fenbufen can be utilized. Such compounds are described in U.S. Pat. No. 3,784,701 and by Child, et al., *J. Pharm. Sci.*, 1977;66:466–476, and Arzneim-Forsch, 1980;30(4A): 695–702, all of which are incorporated herein by reference. Preferred compounds from the fenbufen series to be utilized in this invention have the formula

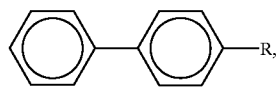

where R is

-continued
COCH=CHCOOH, SO₂NH₂, COCH₂CHCOOH,
|
CH₃

COCH₂CH—COOH, COCH₂CH₂SO₃Na,
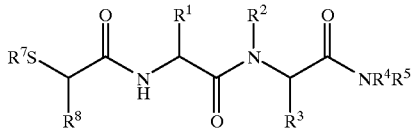

CH(OH)CH₂CH₂COOH, COCH₂CHCOOH, COCH₂CH₂CONHOH,
|
OH

C(=NOH)CH₂CH₂COOH, and COCH₂SCH₂COOH.

Numerous peptides are known matrix metalloproteinase inhibitors. Typical of such peptides are those described in U.S. Pat. Nos. 5,300,501; 5,530,128; 5,455,258; 5,552,419; WO 95/13289; and WO 96/11209, all of which are incorporated herein by reference. Such compounds are illustrated by the formula $$R^7S\underset{R^8}{\overset{O}{\overset{\|}{C}}}-\underset{H}{N}-\underset{R^1}{\overset{}{C}}-\underset{}{\overset{O}{\overset{\|}{C}}}-\underset{R^3}{\overset{R^2}{N}}-\underset{}{\overset{O}{\overset{\|}{C}}}-NR^4R^5$$

where each of the variable groups can include hydrogen alkyl, aryl, heteroaryl, alkenyl, alkynyl, carboxy, and the like. Preferred compounds from within this class which can be utilized in the method of this invention include the following:

N-[2,3-bis-Acetylmercaptopropanoyl]-L-leucyl-L-phenylalanine N-methylamide;
N-[2-acetylmercapto-3-methoxycarbonylpropanoyl]-L-leucyl-L-phenylalanine N-methylamide;
N-[2-acetylmercapto-4-methoxycarbonylbutanoyl]-L-leucyl-L-phenylalanine N-methylamide;
N-[2-acetylmercapto-5-methoxycarbonylpentanoyl]-L-leucyl-L-phenylalanine N-methylamide;
N-[2-acetylmercapto-6-methoxycarbonylhexanoyl]-L-leucyl-L-phenylalanine N-methylamide;
N-[2-acetylmercapto-4-phthalimidobutanoyl]-L-leucyl-L-phenylalanine N-methylamide;
N-[2-acetylmercapto-5-phthalimidopentanoyl]-L-leucyl-L-phenylalanine N-methylamide;
N-[2-acetylmercapto-6-phthalimidohexanoyl]-L-leucyl-L-phenylalanine N-methylamide;
N-[2,3-bis-mercaptopropanoyl]-L-leucyl-L-phenylalanine N-methylamide;
N-[2-mercapto-3-methoxycarbonylpropanoyl]-L-leucyl-L-phenylalanine N-methylamide;
N-[2-mercapto-4-methoxycarbonylbutanyol]-L-leucyl-L-phenylalanine N-methylamide;
N-[2-mercapto-4-methoxycarbonylpentanoyl]-L-leucyl-L-phenylalanine N-methylamide;
N-[2-mercapto-6-methoxycarbonylhexanoyl]-L-leucyl-L-phenylalanine N-methylamide;
N-[2-mercapto-4-phthalimidobutanoyl]-L-leucyl-phenylalanine N-methylamide;
N-[2-mercapto-5-phthalimidopentanoyl]-L-leucyl-L-phenylalanine N-methylamide;
N-[2-mercapto-6-phthalimidohexanyoyl]-L-leucyl-L-phenyl amide;
N-[2-acetylmercapto-5-methoxycarbonylpentanoyl]-L-leucyl-L-phenylalanine N-methylamide;
N-[2-acetylmercapto-6-methoxycarbonylhexanyol]-L-leucyl-L-phenylalanine N-methylamide;
N-[2-acetylmercapto-6-methoxycarbonylhexanyol]-L-valinyl-L-phenylalanine N-methylamide;
N-[2-acetylmercapto-6-methoxycarbonylhexanyol]-L-leucyl-L-tryptophan N-methylamide;
N-[2-acetylmercapto-5-phthalimidopentanoyl]-L-leucyl-L-phenylalanine N-methylamide;
N-[2-acetylmercapto-5-phthalimidopentanoyl]-L-valinyl-L-phenylalanine N-methylamide;
N-[2-acetylmercapto-5-phthalimidopentanoyl]-L-leucyl-L-tryptophan N-methylamide;
N-[2-acetylmercapto-5-phthalimidopentanoyl]-L-leucyl-L-[β-(4-thiazolyl)]alaine N-methylamide;
N-[2-acetylmercapto-5-phthalimidopentanoyl]-L-leucyl-L-(β-(2-pyridyl)alanine N-methylamide;
N-[2-acetylmercapto-5-phthalimidopentanoyl]-L-leucyl-5-methyl-L-glutamicacid N-methylamide;
N-[2-acetylmercapto-6-phthalimidohexanoyl]-L-leucyl-L-phenylalanine N-methylamide;
N-[2-acetylmercapto-2-(3-phthalimido) phenylacetyl]-L-leucyl-L-phenylalanine N-methylamide;
N-[2-mercapto-5-methoxycarbonylpentanoyl]-L-phenylalanine N-methylamide;
N-[2-mercapto-6-methoxycarbonylhexanyol]-L-leucyl-L-phenylalanine N-methylamide;
N-[2-mercapto-6-methoxycarbonylhexanyol]-L-leucyl-L-trptophan N-methylamide;
N-[2-mercapto-5-phthalimidopentanoyl]-L-leucyl-L-phenylalanine N-methylamide;
N-[2-mercapto-5-phthalimidopentanoyl]-L-leucyl-L-tryptophan N-methylamide;
N-[2-mercapto-5-phthalimidopentanoyl]-L-leucyl-L-[β-(4-thiazolyl)alanine N-methylamide;
N-[2-mercapto-5-phthalimidopentanoyl]-L-leucyl-L-[β-(2-pyridyl)]alanine N-methylamide;
N-[2-mercapto-5-phthalimidopentanoyl]-L-leucyl-5-methyl-L-glutamic acid N-methylamide;
N-[2-mercapto-6-phthalimidohexanoyl]-L-leucyl-L-phenylalanine N-methylamide;
N-[N-mercaptoacetyl)-L-leucyl]-L-phenylalanine N-methylamide;
N-[acetomercaptoacyl)-L-leucyl-L-phenylalanine methylamide;
(RS)-2-(acetylthio)pentanoyl-L-leucyl-L-phenylalanine N-methylamide;
(RS)-2-(acetylthio)propanoyl-L-leucyl-L-phenylalanine N-methylamide;
(RS)-2-(acetylthio)-3-methylbutanoyl-L-leucyl-L-phenylalanine N-methylamide;
(RS)-2-(acetylthio)-2-phenylacetyl-L-leucyl-L-phenylalanine N-methylamide;
(RS)-2-(acetylthio)-3-phenylpropanoyl-L-leucyl-L-phenylalanine N-methylamide;
(RS)-2-(acetylthio)-4-phenylbutanoyl-L-leucyl-L-phenylalanine N-methylamide;
N-(acetylmercaptoacyl)-L-threonyl-L-phenylalanine methylamide;
N-(acetylmercaptoacyl)-L-leucyl-L-tryptophan methylamide;
(RS)-2-mercaptopentanoyl-L-leucyl-L-phenylalanine N-methylamide;
(RS)-2-mercaptopropanoyl-L-leucyl-L-phenylalanine N-methylamide;
(RS)-2-mercapto-3-methylbutanoyl-L-leucyl-L-phenylalanine N-methylamide;

(RS)-2-mercapto-2-phenylacetyl-L-leucyl-L-phenylalanine N-methylamide;
(RS)-2-mercapto-3-phenylpropanoyl-L-leucyl-L-phenylalanine N-methylamide;
(RS)-2-mercapto-4-phenylbutanoyl-L-leucyl-L-phenylalanine N-methylamide;
N-[N-(mercaptoacetyl)-L-threonyl]-L-phenylalanine methylamide; and
N-[N-(mercaptoacetyl)-L-leucyl]-L-tryptophan methylamide.

Additional matrix metalloproteinase (MMP) inhibitors, which can be utilized to prevent and treat heart failure and ventricular dilatation, include the following:

[4-(N-Hydroxyamino)-2(R)-cyclohexylmethylsuccinyl]-L-β-cyclohexylalanine-N-(2-phenylethyl)amide;
[4-N-(Hydroxyamino)-2R-isobutylsuccinyl]-L-β-cyclohexylalanine-N-(2-phenylethyl)amide;
[4-(N-hydroxyamino)-2R-phenylpropylsuccinyl]-L-β-cyclohexylalanine-N-(2-phenylethyl)amide;
[4-(N-Hydroxyamino)-2R-phenylpropylsuccinyl]-L-β-cyclohexylalanine-N-[2-(N,N-dimethylamino]ethyl) amide;
[4-(N-Hydroxyamino)-2R-phenylpropylsuccinyl]-L-β-cyclohexylalanine-N-[2-(p-sulphonamidophenyl)ethyl] amide;
[4-(N-Hydroxyamino)-2R-phenylpropylsuccinyl]-L-β-cyclohexylalanine-N-(2-(p-sulphonylphenyl)ethyl) amide;
[4-(N-Hydroxyamino)-2R-phenylpropylsuccinyl]-L-β-cyclohexylalanine-N-[2-(2-pyridyl)ethyl]amide;
[4-(N-Hydroxyamino)-2R-pentylsuccinyl]-L-β-cyclohexylalanine-N-(2-phenylethyl)amide;
[4-(N-Hydroxyamino)-2R-isoamylsuccinyl]-L-β-cyclohexylalanine-N-(2-phenylethyl)amide;
[4-(N-Hydroxyamino)-2R-phenylbutylsuccinyl]-L-β-cyclohexylalanine-N-(2-phenylethyl)amide;
[4-(N-Hydroxyamino)-2R-phenylpropylsuccinyl]-L-β-cyclohexylaianine-N-[3-(4-morpholinyl)propyl]amide;
[4-(N-Hydroxyamino)-2R-phenylpropylsuccinyl]-L-β-cyclohexylalanine-N-[β-alanine]amide;
[4-(N-Hydroxyamino)-2R-isobutylsuccinyl]-L-β-cyclohexylalanine amide;
[4-(N-Hydroxyamino)-2R-(3-phenylpropyl)succinyl]-L-β-cyclohexylalanine amide;
[4-(N-Hydroxyamino)-2R-(3-phenylbutyl)succinyl]-L-β-cyclohexylalanine amide;
[4-N-(Hydroxyamino)-2R-phenylethylsuccinyl]-L-leucine-N-(2-phenylethyl)amide;
[4-(N-Hydroxyamino)-2R-phenylpropylsuccinyl]-L-leucine-N-(2-phenylethyl)amide;
[4-(N-Hydroxyamino)-2(R)-isobutylsuccinyl]-L-tryptophan amide;
[4-(N-Hydroxyamino)-2(R)-isobutylsuccinyl]-L-valine amide;
[3-Phosphono-2R,S-phenylpropyl-1-oxopropyl]-L-β-cyclohexylalanine-N-(2-phenylethyl)amide, dimethylester;
[3-Phosphono-2R-phenylpropyl-1-oxopropyl]-L-β-cyclohexylalanine-N-(2-phenylethyl)amide;
[3-Phosphono-2S-phenylpropyl-1-oxopropyl]-L-β-cyclohexylalanine-β-alanine;
[3-Phosphono-2R-phenylpropyl-1-oxopropyl]-L-β-cyclohexylalanine;
[3-Phosphono-2S-phenylpropyl-1-oxopropyl]-L-β-cyclohexylalanine-β-alanine, methyl ester;
[3-Phosphono-2R,S-phenylpropyl-1-oxopropyl]-L-β-cyclohexylalanine-N-[4(3-aminopropyl)morpholine] amide, bromine salt;
[3-Phosphono-2R,S-(4-methylphenyl)propyl-1-oxopropyl]-L-β-cyclohexylalanine-N-(2-phenylethyl)amide, diethylester;
[3-Phosphono-2R,S-(4-methylphenyl)propyl-1-oxopropyl]-L-β-cyclohexylalanine-N-(2-phenylethyl)-amide;
4-t-Butoxy-2(R)-[3-(2-phenoxyethyl)succinyl]-L-β-cyclohexylalanine-N-(2-phenylethyl)amide;
4-Hydroxy-2(R)-[3-(2-phenoxyethyl)succinyl]-L-p-cyclohexylalanine-N-(2-phenylethyl)amide;
4-(N-Hydroxyamino-2(R)-[3-(2-phenoxyethyl)succinyl]-L-β-cyclohexylalanine-N-(2-phenylethyl)amide;
{4-Hydroxy-2(R)-[3-(4-pyridinium)propyl]succinyl}-L-β-cyclohexylalanine-N-(2-phenylethyl)amide;
{4-(N-Hydroxyamino)-2(R)-[3-(4-pyridinium)propyl] succinyl}-L-β-cyclohexylalanine-N-(2-phenylethyl) amide;
{4-(N-Hydroxyamino)-2(R)-[3-(N -methyl-4-pyridinium) propyl]succinyl}-L-β-cyclohexylalanine-N-(2-phenylethyl)amide;
{4-Hydroxy-2-(R)-[3-(4-methylphenyl)propyl]succinyl}-L-β-cyclohexylalanine-N-[(2-morpholine-sulphonylamino) ethyl]amide;
{4-(N-Hydroxyamino)-2-(R)-[3-(4-methylphenyl) propyljsuccinyl}-L-β-cyclohexylalanine-N-[(2-morpholinesulphonylamino)ethyl]amide;
{4-(N-Hydroxyamino)-2-(R)-[3-(4-chlorophenyl)propyl] succinyl}-L-β-cyclohexylalanine-N-[(2-morpholinesulphonylamino)ethyl]amide;
{4-N-Hydroxyamino)-2-(R)-[3-(4-methylphenyl)propyl] succinyl}-L-β-cyclohexylalanine-N-[(2-dimethylsulphonylamino)propyl]amide;
[4-(N-Hydroxyamino)-2(R)-[3-(4-chlorophenyl)propyl] succinyl]-L-[S-(methyl)penicillamine]-N-methylamide;
[4-(N-Hydroxyamino)-2(R)-[3-(4-chlorophenyl)propyl] succinyl]-L-[S-(methyl)penicillamine]amide;
[4-(N-Hydroxyamino)-2(R)-[3-(4-chlorophenyl)propyl] succinyl]-L-penicillamine]amide;
{4-(N-Hydroxyamino)-2(R)-[3-(4-chlorophenyl)propyl] succinyl}-L-[S-(methyl)penicillaminesulphone]-N-methylamide;
{4-(N-Hydroxyamino)-2(R)-[3-(4-chlorophenyl)propyl) succinyl}-L-[S-(methyl)penicillaminesulphoxide]-N-methylamide;
{4-(N-Hydroxyamino)-2(R)-[3-(4-chlorophenyl)propyl] succinyl}-L-penicillamine-N-methylamide;
[4-(N-Hydroxyamino)-2(R)-3-(2-methylpropyl)succinyl]-L-[S-methyl)penicillamine]-N-methylamide;
$N^{4}$-Hydroxy-$N^{1}$-(1-(S)-carbamoyl-2,2-dimethylpropyl)-2-(R)-4-(chlorophenylpropyl)succinamide;
$N^{4}$-Hydroxy-$N^{1}$-(1-(S)-carbamoyl-2,2-dimethylpropyl)-2-(R)-(4-methylphenylpropyl)succinamide;
$N^{4}$-Hydroxy-$N^{1}$-(1-(S)-carbamoyl-2,2-dimethylpropyl)-2-(R)-(4-methoxyphenylpropyl)succinamide;
$N^{4}$-Hydroxy-$N^{1}$-(1-(S)-carbamoyl-2,2-dimethylpropyl)-2-(R)-(4-trifluoromethylphenylpropyl)succinamide;
$N^{4}$-Hydroxy-$N^{1}$-(1-(S)-carbamoyl-2,2-dimethylpropyl)-2-(R)-(4-chloromethylphenylpropyl)succinamide;
N-[N-(Mercaptoacetyl)-L-leucyl]-L-phenylalanine methylamide;
N-(Acetomercaptoacyl)-L-leucyl]-L-phenylalanine methylamide;
(RS)-2-(Acetylthio)pentanoyl-L-leucyl-L-phenylalanine N-methylamide;
(RS)-2-(Acetylthio)propanoyl-L-leucyl-L-phenylalanine N-methylamide;
(RS)-2-(Acetylthio)-3-methylbutanoyl-L-leucyl-L-phenylalanine N-methylamide;

(RS)-2-(Acetylthio)-2-phenylacetyl-L-leucyl-L-phenylalanine N-methylamide;
(RS)-2-(Acetylthio)-3-phenylpropanoyl-L-leucyl-L-phenylalanine N-methylamide;
(RS)-2-(Acetylthio)-4-phenylbutanoyl-L-leucyl-L-phenylalanine N-methylamide;
N-(Acetylmercaptoacyl)-L-threonyl-L-phenylalanine methylamide;
N-(Acetylmercaptoacyl)-L-leucyl-L-tryptophan methylamide;
(RS)-2-Mercaptopentanoyl-L-leucyl-L-phenylalanine N-methylamide;
(RS)-2-Mercaptopropanoyl-L-leucyl-L-phenylalanine N-methylamide;
(RS)-2-Mercapto-3-methylbutanoyl-L-leucyl-L-phenylalanine N-methylamide;
(RS)-2-Mercapto-2-phenylacetyl-L-leucyl-L-phenylalanine N-methylamide;
(RS)-2-Mercapto-3-phenylpropanoyl-L-leucyl-L-phenylalanine N-methylamide;
(RS)-2-Mercapto-4-phenylbutanoyl-L-leucyl-L-phenylalanine N-methylamide;
N-[N-(Mercaptoacetyl)-L-threonyl]-L-phenylalanine methylamide;
N-[N-(Mercaptoacetyl)-L-leucyl]-L-tryptophan methylamide;
N-[2,3-bis-Acetylmercaptopropanoyl]-L-leucyl-L-phenylalanine N-methylamide;
N-[2-Acetylmercapto-3-methoxycarbonylpropanoyl]-L-leucyl-L-phenylalanine N-methylamide;
N-[2-Acetylmercapto-4-methoxycarbonylbutanoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanoyl]-L-leucyl-L-phenylalanine N-methylamide;
N-[2-Acetylmercapto-4-phthalimidobutanoyl]-L-leucyl-L-phenylalanine N-methylamide;
N-[2-Acetylmercapto-5-phthalimidopentanoyl]-L-leucyl-L-phenylalanine N-methylamide;
N-[2-Acetylmercapto-6-phthalimidohexanoyl]-L-leucyl-L-phenylalanine N-methylamide;
N-[2,3-bis-Mercaptopropanoyl]-L-leucyl-L-phenylalanine N-methylamide;
N-[2-Mercapto-3-methoxycarbonylpropanoyl]-L-leucyl-L-phenylalanine N-methylamide;
N-[2-Mercapto-4-methoxycarbonylbutanoyl]-L-leucyl-L-phenylalanine N-methylamide;
N-[2-Mercapto-5-methoxycarbonylpentanoyl]-L-leucyl-L-phenylalanine N-methylamide;
N-[2-Mercapto-6-methoxycarbonylhexanoyl]-L-leucyl-L-phenylalanine N-methylamide;
N-[2-Mercapto-4-phthalimidobutanoyl]-L-leucyl-L-phenylalanine N-methylamide;
N-[2-Mercapto-5-phthalimidopentanoyl]-L-leucyl-L-phenylalanine N-methylamide;
N-[2-Mercapto-6-phthalimidohexanoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanoyl]-L-leucyl-L-phenylalanine N-methylamide;
N-[2-Acetylmercapto-6-methoxycarbonylhexanoyl]-L-valinyl-L-phenylalanine N-methylamide;
N-[2-Acetylmercapto-6-methoxycarbonylhexanoyl]-L-leucyl-L-tryptophan N-methylamide;
N-[2-Acetylmercapto-5-phthalimidopentanoyl]-L-leucyl-L-phenylalanine N-methylamide;
N-[2-Acetylmercapto-5-phthalimidopentanoyl]-L-valinyl-L-phenylalanine N-methylamide;
N-[2-Acetylmercapto-5-phthalimidopentanoyl]-L-leucyl-L-tryptophan N-methylamide;
N-[2-Acetylmercapto-5-phthalimidopentanoyl]-L-leucyl-L-[β-(4-thiazolyl)]alanine N-methylamide;
N-[2-Acetylmercapto-5-phthalimidopentanoyl]-L-leucyl-L-[β-(2-pyridyl)]alanine N-methylamide;
N-[2-Acetylmercapto-5-phthalimidopentanoyl]-L-leucyl-5-methyl-L-glutamic acid N-methylamide;
N-[2-Acetylmercapto-6-phthalimidohexanoyl]-L-leucyl-L-phenylalanine N-methylamide;
N-[2-Acetylmercapto-2-(3-phthalimido)phenylacetyl]-L-leucyl-L-phenylalanine N-methylamide;
N-[2-Mercapto-5-methoxycarbonylpentanoyl]-L-leucyl-L-phenylalanine N-methylamide;
N-[2-Mercapto-6-methoxycarbonylhexanoyl]-L-leucyl-L-phenylalanine N-methylamide;
[2-Mercapto-6-methoxycarbonylhexanoyl]-L-leucyl-L-tryptophan N-methylamide;
N-[2-Mercapto-5-phthalimidopentanoyl]-L-leucyl-L-phenylalanine N-methylamide;
N-[2-Mercapto-5-phthalimidopentanoyl]-L-leucyl-L-tryptophan N-methylamide;
N-[2-Mercapto-5-phthalimidopentanoyl]-L-leucyl-L-[β-(4-thiazolyl)alanine N-methylamide;
N-[2-Mercapto-5-phthalimidopentanoyl]-L-leucyl-L-[β-(2-pyridyl)]alanine N-methylamide;
N-[2-Mercapto-5-phthalimidopentanoyl]-L-leucyl-5-methyl-L-glutamic acid N-methylamide;
N-[2-Mercapto-6-phthalimidohexanoyl]-L-leucyl-L-phenylalanine N-methylamide;
N-Hydroxy-2(R)-[[4-methoxybenzenesulfonyl]-(3-picolyl)amino]-3-methylbutanamide;
N-Hydroxy-2(R)-[[4-methoxybenzenesulfonyl]-3-picolyl)amino]-2-cyclohexylacetamide;
N-Hydroxy-2(R)-[[4-methoxybenzenesulfonyl]-(benzyl)amino]-4-methylpentanamide;
N-Hydroxy-2(R)-[[4-methoxybenzenesulfonyl]-(benzyl)amino]-6-[(N,N-dimethylglycyl)amino]hexanamide hydrochloride;
N-Hydroxy-2(R)-[[4-methoxybenzenesulfonyl]-(3-picolyl)amino]-3-methylbutanamide;
N-Hydroxy-2(R)-[[4-methoxybenzenesulfonyl]-(4-picolyl)amino]-2-cyclohexylacetamide;
N-Hydroxy-2(R)-[(4-methoxybenzenesulfonyl]-(4-picolyl)amino]-2-(2-tetrahydrofuranyl)acetamide;
N-Hydroxy-2(R)-[[4-methoxybenzenesulfonyl]-(3-picolyl)amino]-3-methylbutanamide;
[4-(N-Hydroxyamino)-2R-isobutyl-3S-methylsuccinyl]-N$^{2-}$(S)-piperazic acid N-methyl amide;
[4-(N-Hydroxyamino)-2R-isobutyl-3S-benzylsuccinyl]-N$^{2-}$(S)-piperazic acid N-methyl amide;
[4-(N-Hydroxyamino)-2R-isobutyl-3S-methoxyphenylsuccinyl]-N$^{2-}$(S)-piperazic acid N-methyl amide;
[4-(N-Hydroxyamino)-2R-isobutyl-3S-methoxybenzylsuccinyl]-N$^{2-}$(S)-piperazic acid N-methyl amide;
[4-(N-Hydroxyamino)-2R-isobutyl-3S-methyl-thiophenylsuccinyl]-N$^{2-}$(S)-piperazic acid N-methyl amide;
[4-(N-Hydroxyamino)-2R-isobutyl-3S-methyl-thiobenzylsuccinyl]-N$^{2-}$(S)-piperazic acid N-methyl amide;
[4-(N-Hydroxyamino)-2R-isobutyl-3S-(methylthio-2-thienyl)succinyl]-N$^{2-}$(S)-piperazic acid N-methyl amide;

[4-(N-Hydroxyamino)-2R-isobutyl-3S-methylacetate]-$N^{2-}$(S)-piperazic acid N-methyl amide;
[4-(N-Hydroxyamino)-2R-isobutyl-3S-methyl-isopropanoate]-$N^{2-}$(S)-piperazic acid N-methyl amide;
[4-(N-Hydroxyamino)-2R-isobutyl-3S-methyl-tert-butanoate]-$N^{2-}$(S)-piperazic acid N-methyl amide;
[4-(N-Hydroxyamino)-2R-isobutyl-3S-methyl-thioacetate]-$N^{2-}$(S)-piperazic acid N-methyl amide;
[4-(N-Hydroxyamino)-2R-isobutyl-3S-methyl-thioisopropanoate]-$N^{2-}$(S)-piperazic acid N-methyl amide;
[4-(N-Hydroxyamino)-2R-isobutyl-3S-methyl-(2-pyridyl)]-$N^{2-}$(S)-piperazic acid N-methyl amide;
[4-(N-Hydroxyamino)-2R-isobutyl-3S-methyl-(3-pyridyl)]-$N^{2-}$(S)-piperazic acid N-methyl amide;
[4-(N-Hydroxyamino)-2R-isobutyl-3S-methyl-(4-pyridyl)]-$N^{2-}$(S)-piperazic acid N-methyl amide;
[4-(N-Hydroxyamino)-2R-isobutyl-3S-methyl thio-tert-butanoate)-$N^{2-}$(S)-piperazic acid N-methyl amide;
[4-(N-Hydroxyamino)-2R-hexyl-3S-methylsuccinyl]-$N^{2-}$(S)-piperazic acid N-methyl amide;
[4-(N-Hydroxyamino)-2R-hexyl-3S-benzylsuccinyl]-$N^{2-}$(S)-piperazic acid N-methyl amide;
[4-(N-Hydroxyamino)-2R-hexyl-3S-methoxyphenylsuccinyl]-$N^{2-}$(S)-piperazic acid N-methyl amide;
[4-(N-Hydroxyamino)-2R-hexyl-3S-methoxybenzylsuccinyl]-$N^{2-}$(S)-piperazic acid N-methyl amide;
[4-(N-Hydroxyamino)-2R-hexyl-3S-methylthiophenylsuccinyl]-$N^{2-}$(S)-piperazic acid N-methyl amide;
[4-(N-Hydroxyamino)-2R-hexyl-3S-methylthiobenzylsuccinyl]-$N^{2-}$(S)-piperazic acid N-methyl amide;
[4-(N-Hydroxyamino)-2R-hexyl-3S-(methylthio-2-thienyl)succinyl]-$N^{2-}$(S)-piperazic acid N-methyl amide;
[4-(N-Hydroxyamino)-2R-hexyl-3S-benzylsuccinyl]-$N^{2-}$(S)-piperazic acid N-methyl amide;
[4-(N-Hydroxyamino)-2R-hexyl-3S-methyl acetate]-$N^{2-}$(S)-piperazic acid N-methyl amide;
[4-(N-Hydroxyamino)-2R-hexyl-3S-methylisopropanoate]-$N^{2-}$(S)-piperazic acid N-methyl amide;
[4-(N-Hydroxyamino)-2R-hexyl-3S-methyl tert-butanoatel-$N^{2-}$(S)-piperazic acid N-methyl amide;
[4-(N-Hydroxyamino)-2R-hexyl-3S-methylthioacetate]-$N^{2-}$(S)-piperazic acid N-methyl amide;
[4-(N-Hydroxyamino)-2R-hexyl-3S-methylthioisopropanoate]-$N^{2-}$(S)-piperazic acid N-methyl amide;
[4-(N-Hydroxyamino)-2R-hexyl-3S-methylthio-tert-butanoate]-$N^{2-}$(S)-piperazic acid N-methyl amide;
[4-(N-Hydroxyamino)-2R-hexyl-3S-methyl-(2-pyridyl)]-$N^{2-}$(S)-piperazic acid N-methyl amide;
[4-(N-Hydroxyamino)-2R-hexyl-3S-methyl-(3-pyridyl)]-$N^{2-}$(S)-piperazic acid N-methyl amide;
[4-(N-Hydroxyamino)-2R-hexyl-3S-methyl-(4-pyridyl)]-$N^{2-}$(S)-piperazic acid N-methyl amide;
[4-(N-Hydroxyamino)-2R-ethylphenyl-3S-methylsuccinyl]-$N^{2-}$(S)-piperazic acid N-methyl amide;
[4-(N-Hydroxyamino)-2R-ethylphenyl-3S-benzylsuccinyl]-$N^{2-}$(S)-piperazic acid N-methyl amide;
[4-(N-Hydroxyamino)-2R-ethylphenyl-3S-methoxyphenylsuccinyl]-$N^{2-}$(S)-piperazic acid N-methyl amide;
[4-(N-Hydroxyamino)-2R-ethylphenyl-3S-methoxybenzylsuccinyl]-$N^{2-}$(S)-piperazic acid N-methyl amide;
[4-(N-Hydroxyamino)-2R-ethylphenyl-3S-methylthiophenylsuccinyl]-$N^{2-}$(S)-piperazic acid N-methyl amide;
[4-(N-Hydroxyamino)-2R-ethylphenyl-3S-methylthiobenzylsuccinyl]-$N^{2-}$(S)-piperazic acid N-methyl amide;
[4-(N-Hydroxyamino)-2R-ethylphenyl-3S -(methylthio-2-thienyl)succinyl]-$N^{2-}$(S)-piperazic acid N-methyl amide;
[4-(N-Hydroxyamino)-2R-ethylphenyl-3S-benzylsuccinyl]-$N^{2-}$(S)-piperazic acid N-methyl amide;
[4-(N-Hydroxyamino)-2R-ethylphenyl-3S-methyl acetate]-$N^{2-}$(S)-piperazic acid N-methyl amide;
[4-(N-Hydroxyamino)-2R-ethylphenyl-3S-methylisopropanoate]-$N^{2-}$(S)-piperazic acid N-methyl amide;
[4-(N-Hydroxyamino)-2R-ethylphenyl-3S-methyl-tert-butanoate]-$N^{2-}$(S)-piperazic acid N-methyl amide;
[4-(N-Hydroxyamino)-2R-ethylphenyl-3S-methylthioacetate]-$N^{2-}$(S)-piperazic acid N-methyl amide;
[4-(N-Hydroxyamino)-2R-ethylphenyl-3S-methylthioisopropanoate]-$N^{2-}$(S)-piperazic acid N-methyl amide;
[4-(N-Hydroxyamino)-2R-ethylphenyl-3S-methylthio-tert-butanoate]-$N^{2-}$(S)-piperazic acid N-methyl amide;
[4-(N-Hydroxyamino)-2R-octyl-3S-methylsuccinyl]-$N^{2-}$(S)-piperazic acid N-methyl amide;
[4-(N-Hydroxyamino)-2R-octyl-3S-methylthiophenylsuccinyl]-$N^{2-}$(S)-piperazic acid N-methyl amide;
[4-(N-Hydroxyamino)-2R-octyl-3S-methylthiobenzylsuccinyl]-$N^{2-}$(S)-piperazic acid N-methyl amide;
[4-(N-Hydroxyamino)-2R-octyl-3S-methylthio-2-thienyl)succinyl]-$N^{1-}$(S)-piperazic acid N-methyl amide;
[4-(N-Hydroxyamino)-2R-octyl-3S-methyl acetate]-$N^{2-}$(S)-piperazic acid N-methyl amide;
[4-(N-Hydroxyamino)-2R-octyl-3S-methylisopropanoate]-$N^{2-}$(S)-piperazic acid N-methyl amide;
[4-(N-Hydroxyamino)-2R-octyl-3S-methyl tert-butanoate]-$N^{2-}$(S)-piperazic acid N-methyl amide;
[4-(N-Hydroxyamino)-2R-octyl-3S-methylthioacetate]-$N^{2-}$(S)-piperazic acid N-methyl amide;
[4-(N-Hydroxyamino)-2R-octyl-3S-methylthioisopropanoate]-$N^{2-}$(S)-piperazic acid N-methyl amide;
[4-(N-Hydroxyamino)-2R-octyl-3S-methylthio-tert-butanoatel-$N^{2-}$(S)-piperazic acid N-methyl amide;
[4-(N-Hydroxyamino)-2R-octyl-3S-methyl-(2-pyridyl)]-$N^{2-}$(S)-piperazic acid N-methyl amide;
[4-(N-Hydroxyamino)-2R-octyl-3S-methyl-(3-pyridyl)]-$N^{2-}$(S)-piperazic acid N-methyl amide;
[4-(N-Hydroxyamino)-2R-octyl-3S-methyl-(4-pyridyl)]-$N^{2-}$(S)-piperazic acid N-methyl amide;
[4-(N-Hydroxyamino)-2R-isobutyl-3S-methylsuccinyl]-$N^{2-}$(S)-4'(S/R)-benzylpiperazic acid N-methyl amide;
[4-(N-Hydroxyamino)-2R-isobutyl-3S-methylsuccinyl]-$N^{2-}$(S)-5'(S/R)-benzylpiperazic acid N-methyl amide;
[4-(N-Hydroxyamino)-2R-isobutyl-3S-methylsuccinyl]-$N^{2-}$(S)-6'(S/R)-benzylpiperazic acid N-methyl amide;
[4-(N-Hydroxyamino)-2R-isobutyl-3S-methylsuccinyl]-$N^{2-}$(S)-[5',6']benzopiperazic acid N-methyl amide;
N-[1(R)-Carboxy-ethyl]-α-(S)-isobutylglycine-(S)-$N^{2-}$piperazic acid methyl amide;
N-[1(R)-Carboxy-ethyl]-α-(S)-hexylglycine-(S)-$N^{2-}$piperazic acid methyl amide;
N-[1(R)-Carboxy-ethyl]-α-(S)-heptylglycine-(S)-$N^{2-}$piperazic acid methyl amide;

N-[1(R)-Carboxy-ethyl]-α-(S)-octylglycine-(S)-N$^{2-}$piperazic acid methyl amide;
N-[1(R)-Carboxy-ethyl]-α-(S)-ethylphenylglycine-(S)-N$^{2-}$piperazic acid methyl amide;
N-[1(R)-Carboxy-ethyl]-α-(S)-propylphenylclycine-(S)-N$^{2-}$piperazic acid methyl amide;
N-[1(R)-Carboxy-ethylthiobenzyl]-α-(S)-isobutylglycine-(S)-N$^{2-}$piperazic acid methyl amide;
N-[1(R)-Carboxy-ethylthiobenzyl]-α-(S)-hexylglycine-(S)-N$^{2-}$piperazic acid methyl amide;
N-[1(R)-Carboxy-ethylthiobenzyl]-α-(S)-ethylphenylglycine-(S)-N$^{2-}$piperazic acid methyl amide;
N-[1(R)-Carboxy-ethylthiobenzyl]-α-(S)-propylphenylglycine-(S)-N$^{2-}$piperazic acid methyl amide;
N-[1(R)-Carboxy-ethyloxybenzyl]-α-(S)-isobutylglycine-(S)-N$^{2-}$piperazic acid methyl amide;
N-[1(R)-Carboxy-ethyloxybenzyl]-α-(S)-hexylglycine-(S)-N$^{2-}$piperazic acid methyl amide;
N-[1(R)-Carboxy-ethyloxybenzyl]-α-(S)-ethylphenylglycine-(S)-N$^{2-}$piperazic acid methyl amide;
N-[1(R)-Carboxy-ethyloxybenzyl]-α-(S)-propylphenylglycine-(S)-N$^2$-piperazic acid methyl amide;
N-[1(R)-Carboxy-4-(p-toluenesulfonyl)butyl]-α-(S)-phenethylglycyl-(S)-N$^2$-piperazic acid methyl amide;
N-[1(R)-Carboxyethyl]-α-[2-(4-phenylphenoxy)ethyl]-glycyl-(S)-N$^2$-piperazic acid methyl amide;
2-[2(R)-[2-[1,1'-Biphenyl)yl]ethyl]-4-butyl-4(S)-carboxy-1-oxobutyl]-3(S)-methylaminocarbonyl-hexahydropyridazine;
2-[2(R)-[2-1,1'-Biphenyl)yl]ethyl]-4-methyl-4(S)-carboxy-1-oxobutyl]-3(S)-methylaminocarbonyl-hexahydropyridazine;
2-[2(R)-[2-[1,1'-Biphenyl)yl]propyl]-4-butyl-4(S)-carboxy-1-oxobutyl]-3(S)-methylaminocarbonyl-hexahydropyridazine;
2-[2(R)-[2-(4-Propylphenyl)ethyl]-4-butyl-4(S)-carboxy-1-oxobutyl]-3(S)-methylaminocarbonyl-hexahydropyridazine;
2-[2(R)-[2-(4-Butylphenyl)ethyl]-4-butyl-4(S)-carboxy-1-oxobutyl]-3(S)-methylaminocarbonyl-hexahydropyridazine;
2-[2(R)-[2-(4-t-Butylphenyl)ethyl]-4-butyl-4(S)-carboxy-1-oxobutyl]-3(S)-methylaminocarbonyl-hexahydropyridazine;
2-[2(R)-[2-[4-(4-Fluorophenyl)phenyl]ethyl]-4-butyl-4(S)-carboxy-1-oxobutyl]-3(S)-methylaminocarbonyl-hexahydropyridazine;
2-[2(R)-[2-[4-(4-Fluorophenyl)phenyl]ethyl]-4-methyl-4(S)-carboxy-1-oxobutyl]-3(S)-methylaminocarbonyl-hexahydropyridazine;
2-[2(R)-[2-n-Octyl-4-methyl-4(S)-carboxy-1-oxobutyl]-3(S)-methylaminocarbonyl-hexahydropyridazine;
2-[2(R)-[2-[(4-Thiazolyl)phenyl]ethyl]-4-butyl-4(S)-carboxy-1-oxobutyl]-3(S)-methylaminocarbonyl-hexahydropyridazine;
2-[2(R)-[2-[(4-Thiazolyl)phenyl]ethyl]-4-methyl-4(S)-carboxy-1-oxobutyl]-3(S)-methylaminocarbonyl-hexahydropyridazine;
2-[2(R)-[2-[(4-Thiazolyl)phenyl]ethyl]-4-[3-(phenylsulfonyl)propyl-4(S)-carboxy-1-oxobutyl]-3(S)-methylaminocarbonyl-hexahydropyridazine;
2-[2(R)-[2-[(4-Thiazolyl)phenyl]ethyl)-4-(3-phenylpropyl)-4(S)-carboxy-1-oxobutyl]-3(S)-methylaminocarbonyl-hexahydropyridazine;
2-[2(R)-[2-[(4-Oxazolyl)phenyl]ethyl]-4-butyl-4(S)-carboxy-1-oxobutyl]-3(S)-methylaminocarbonyl-hexahydropyridazine;
2-[2(R)-[2-[(4-Oxazolyl)phenyl]ethyl]-4-methyl-4(S)-carboxy-1-oxobutyl]-3(S)-methylaminocarbonyl-hexahydropyridazine;
2-[2(R)-[2-[(4-Oxazolyl)phenyl]ethyl]-4-[3-(phenylsulfonyl)propyl-4(S)-carboxy-1-oxobutyl]-3(S)-methylaminocarbonyl-hexahydropyridazine;
2-[2(R)-[2-[(4-Oxazolyl)phenyl]ethyl]-4-(3-phenylpropyl)-4(S)-carboxy-1-oxobutyl]-3(S)-methylaminocarbonyl-hexahydropyridazine;
2-[2(R)-[2-[4-(Dimethylamino)methylphenyl]ethyl]-4-butyl-4(S)-carboxy-1-oxobutyl]-3(S)-methylaminocarbonyl-hexahydropyridazine;
2-[2(R)-[2-[4-(Dimethylamino)methylphenyl]ethyl]-4-methyl-4(S)-carboxy-1-oxobutyl]-3(S)-methylaminocarbonyl-hexahydropyridazine;
2-[2(R)-[2-[4-(Dimethylamino)methylphenyl]ethyl]-4-[3-(phenylsulfonyl)propyl-4(S)-carboxy-1-oxobutyl]-3(S)-methylaminocarbonyl-hexahydropyridazine;
2-[2(R)-[2-[4-(Dimethylamino)methylphenyl]ethyl]-4-(3-phenylpropyl)-4(S)-carboxy-1-oxobutyl]-3(S)-methylaminocarbonyl-hexahydropyridazine;
2-[2(R)-[2-[(4-Imidazolyl)phenyl]ethyl]-4-butyl-4(S)-carboxy-1-oxobutyl]-3(S)-methylaminocarbonyl-hexahydropyridazine;
2-[2(R)-[2-[(4-Imidazolyl)phenyl]ethyl]-4-methyl-4(S)-carboxy-1-oxobutyl]-3(S)-methylaminocarbonyl-hexahydropyridazine;
2-[2(R)-[2-[(4-Imidazolyl)phenyl]ethyl]4-[3-(phenylsulfonyl)propyl-4(S)-carboxy-1-oxobutyl]-3(S)-methylaminocarbonyl-hexahydropyridazine;
2-[2(R)-[2-[(4-Imidazolyl)phenyl]ethyl]-4-[3-(phenylpropyl)-4(S)-carboxy-1-oxobutyl]-3(S)-methylaminocarbonyl-hexahydropyridazine;
HS(CH$_2$)$_2$—(S—D—Leu)—Phe—NHMe;
HS(S)CHMeCH$_2$—(S—D—Leu)—Phe—NHMe;
HS(S)CH(PhtNBu)CH$_2$—(S—D—Leu)—Phe—NHMe;
HS(S)CH(PhtNEt)CH$_2$—(S—D—Leu)—Phe—NHMe;
HS(1,2-Cyclopentyl)(S—D—Leu)—Phe—NHMe
Me-S(NH)$_2$—(CH$_2$_DL—Leu)—Trp—NHBn;
n-Bu—S(NH)$_2$—(CH$_2$_DL—Leu)—Trp—NHBn;
n-Bu—S(NH)$_2$—(CH$_2$_DL—TyrOCH$_3$)-Trp-NHBn;
Me—RS—SO(NH)—(CH$_2$_L—Leu)—Phe—Ala—NH$_2$;
n-Bu—RS—SO(NH)—(CH$_2$_L—Leu)—Phe—Ala—NH$_2$;

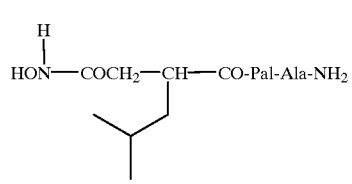

wherein Pal is 3-pyridylalanine;

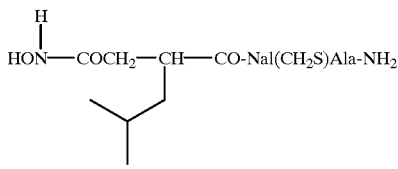

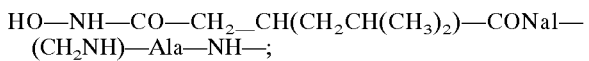

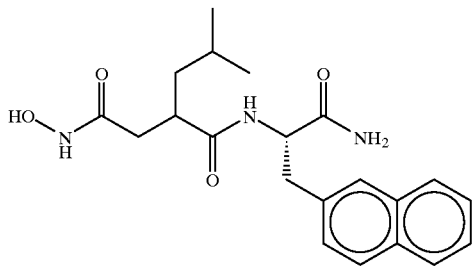

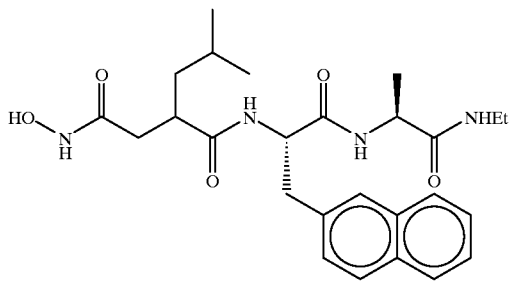

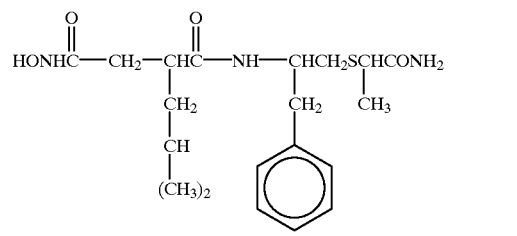

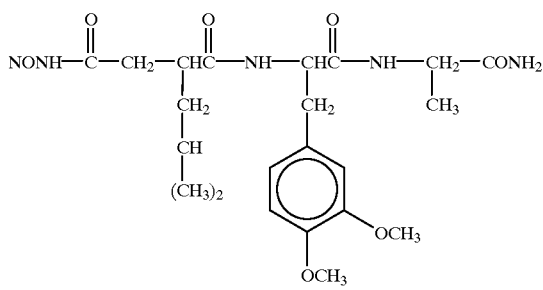

4-(1,3-Dihydro-1,3-dioxo-2H-benz[f]isoindol-2-yl)-2-(R)-[[3-methyl-1-(S)-[[(2-morpholin-4-ylethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[methylamino]carbonyl]butyl]amino]-butanoic acid;
4-(1,3-Dihydro-1,3-dioxo-2H-benz[f]isoindol-2-yl)-2-(R)-[[3-methyl-1-(S)-[[(1H-imidazol-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[(2-(phenyl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2-methyl-2H-tetrazo-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2,4-difluoro-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-methanesulfonylamino-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-methanesulfonylamino-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3,4-difluoro-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-trifluoromethyl-benzyl)amino]carbonyl]butyl]amino]-butanoic acid;
4-[2-(S)-[1-(R)-Carboxy-3-(1,3-dioxo-1,3-dihydro-benzo[f]isoindol-2-yl)-propylamino]-4-methyl-pentanoylamino-methyl)-benzoic acid;
4-(1,3-Dihydro-1,3-dioxo-2H-benz[f]isoindol-2-yl)-2-(R)-[[3-methyl-1-(S)-[[(2-hydroxy-1,1-bis-hydroxymethyl-ethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3,5-difluoro-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[benzylmethyl-amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2-dimethylaminoethyl)-methyl-amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1-azabicyclo[2.2.2]-oct-3(R)-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1-azabicyclo[2.2.2]oct-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-4-(S)-5-(R)-6-tetrahydrox-tetrahydra-pyran-2-(R)-ylmethyl)amino-carbonyl]butyl]amino]-butanoic acid;

4-(1,3-Dihydro-1,3-dioxo-2H-benz[f]isoindol-2-yl)-2-(R)-[[3-methyl-1-(S)-[[(N,N'-dimethyl-hydrazino)carbonyl]butyl]amino]-butanoic acid;

4-(1,3-Dihydro-1,3-dioxo-2H-benz[f]isoindol-2-yl)-2-(R)-[[3-methyl-1-(S)-[[(methylmethoxy)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid;

4-(1,3-Dihydro-1,3-dioxo-2H-benz[f]isoindol-2-yl)-2-(R)-[[3-methyl -1-(S)-[[benzyl(2-hydroxyethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid;

4-(1,3-Dihydro-1,3-dioxo-2H-benz[f]isoindol-2-yl)-2-(R)-[[3-methyl-1-(S)-[4-methylpiperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[1-oxo-[1,4]thiazinane-4-carbonyl]butyl]amino]-butanoic acid;

4-(1,3-Dihydro-1,3-dioxo-2H-benz[f]isoindol-2-yl)-2-(R)-[[3-methyl-1-(S)-[morpholine-4-carbonyl]butyl]amino]-butanoic acid;

4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1]carbonyl]butyl]amino]-butanoic acid;

4-(1,3-Dihydro-1,3-dioxo-2H-benz[f]isoindol-2-yl)-2-(R)-[[3-methyl-1-(S)-[[(1-methyl-8-oxo-1,7-diazacyclotridec-9-yl)aminolcarbonyl]butyl]amino]-butanoic acid;

4-(1,3-Dihydro-1,3-dioxo-2H-benz[f]isoindol-2-yl)-2-(R)-[[3-methyl-1-(S)-[[methyl-1-methyl-piperidin-4-yl)amino)carbonyl]butyl]amino)-butanoic acid;

4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]-amino]-butanoic acid;

4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid;

4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]-amino]-butanoic acid;

4-(1,3-Dihydro-1,3-dioxo-2H-benz[f]isoindol-2-yl)-2-(R)-[[3-methyl-1-(S)-[2-(R)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[2-(S)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(R)-phenyl-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(S)-phenyl-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[(pyridine-3-carbonyl-hydrazino)carbonyl]butyl]amino]-butanoic acid;

4-(1,3-Dihydro-1,3-dioxo-2H-benz[f]isoindol-2-yl)-2-(R)-[[3-methyl-1-(S)-[[(benzenesulfonyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-aminobenzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[[4-(trifluoro-methanesulfonylamino)benzyl]amino]carbonyl]butyl]amino]-butanoic acid;

4-(1,3-Dihydro-1,3-dioxo-2H-benz[f]isoindol-2-yl)-2-(R)-[[3-methyl-1-(S)-[[[2-hydroxy-(R)-bicyclo[4.3.0]nona-3,6(1)-diene]amino]carbonyl]butyl]-amino]-butanoic acid;

4-(1,3-Dihydro-1,3-dioxo-2H-benz[f]isoindol-2-yl)-2-(R)-[[3-methyl-1-(S)-[[[2-hydroxy-(S)-bicyclo[4.3.0]nona-3,6(1)-diene]amino]carbonyl]butyl]-amino]-butanoic acid;

4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[(N-ethoxycarbonylmethyl-piperazine)-1-carbonyl]butyl]amino]-butanoic acid;

2-(R)-[1-(S)-(Benzylamino)carbonyl-3-methylbutylamino]-4-(5-bromo-1,3-dioxo-1,3-dihydro-isoindol-2-yl)-butanoic acid;

2-(R)-[1-(S)-(Benzylamino)carbonyl-3-methylbutylamino]-4-(5-propoxy-1,3-dioxo-1,3-dihydro-isoindol-2-yl)-butanoic acid;

2-(R)-[1-(S)-(Benzylamino)carbonyl-3-methylbutylamino]-4-(5-nitro-1,3-dioxo-1,3-dihydro-isoindol-2-yl)-butanoic acid;

2-(R)-[1-(S)-(Benzylamino)carbonyl-3-methylbutylamino]-4-(5-amino-1,3-dioxo-1,3-dihydro-isoindol-2-yl)-butanoic acid;

2-(R)-[1-(S)-(Benzylamino)carbonyl-3-methylbutylamino]-4-(5-methyl-1,3-dioxo-1,3-dihydro-isoindol-2-yl)-butanoic acid;

2-(R)-[1-(S)-(Benzylamino)carbonyl-3-methylbutylamino]-4-(5-methoxy-1,3-dioxo-1,3-dihydro-isoindol-2-yl)-butanoic acid;

2-(R)-[1-(S)-(Benzylamino)carbonyl-3-methylbutylamino]-4-(5-benzyloxy-1,3-dioxo-1,3-dihydro-isoindol-2-yl)-butanoic acid;

2-(R)-[1-(S)-(Benzylamino)carbonyl-3-methylbutylamino]-4-(5-phenyl-1,3-dioxo-1,3-dihydro-isoindol-2-yl)-butanoic acid;

2-(R)-[1-(S)-(Benzylamino)carbonyl-3-methylbutylamino]-4-1,3-dioxo-1,3-dihydro-isoindol-2-yl)-butanoic acid;

2-(R)-[1-(S)-(Benzylamino)carbonyl-3-methylbutylamino]-4-(5-methanesulfonylamino-1,3-dioxo-1,3-dihydro-isoindol-2-yl)-butanoic acid;

2-(R)-[1-(S)-(Benzylamino)carbonyl-3-methylbutylamino]-4-(5-benzenesulfonylamino-1,3-dioxo-1,3-dihydro-isoindol-2-yl)-butanoic acid;

2-(R)-[1-(S)-(Benzylamino)carbonyl-3-methylbutylamino]-4-(5-hydroxy-1,3-dioxo-1,3-dihydro-isoindol-2-yl)-butanoic acid;

2-(R)-[[3-Methyl-1-(S)-[[(pyridin-3-ylmethyl)amino]carbonyl]-butyl]amino]-4-(1,3,5,7-tetraoxo-3,5,6-tetrahydro-1H-pyrolo[3,4-f]isoindol-2-yl)butanoic acid;
EtONHCONMe—CH₂CH(iBu)—CO—L—Trp—NHEt;
EtCONOH—CH₂CH(iBu)—CO—L—Trp—NHEt;
n-PrCONOEt—CH₂CH(iBu)—CO—L—Trp—NHEt;
EtNHCONOMe—CH₂CH(iBu)—CO—L—Trp—NHEt;
MeNHCONOH—CH₂CH(iBu)—CO—L—Trp—NHEt;
EtONHCONMe—CH₂CH(iBu)—CO—L—Ala(2-naphthyl)—NHEt;
EtCONOH—CH₂CH(iBu)—CO—L—Ala(2-naphthyl)—NHEt;
n-PrCONOEt—CH₂CH(iBu)—CO—L—Ala(2-naphthyl)—NHEt;
EtNHCONOMe—CH₂CH(iBu)—CO—L—Ala(2-naphthyl)—NHEt;
MeNHCONOH—CH₂CH(iBu)—CO—L—Ala(2-naphthyl)—NHEt;
HONHCONHCH₂CH(iBu)—CO—L—TrpNHMe;
HONHCONHCH₂CH₂CH(iBu)—CO—L—TrpNHMe;
HONHCONHCH(iBu)—CO—L—TrpNHMe;
H₂NCON(OH)CH(iBu)—CO—L—TrpNHMe;
N(OH)CH₂CH(iBu)—CO—L—TrpNHMe;
H₂NCON(OH)CH₂CH₂CH(iBu)—CO—L—TrpNHMe;
CH₃CON(OH)CH(iBu)—CO—L—TrpNHMe;
CH₃CON(OH)CH₂CH(iBu)—CO—L—TrpNHMe;
CH₃CON(OH)CH₂CH₂CH(iBu)—CO—L—TrpNHMe;
NHOHCOCH₂CH(i-Bu)CO—L—Trp—NHMe;

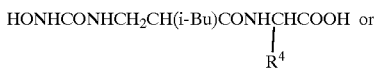

ROOCCH₂CH(i-Bu)CONHCHCOOH;
　　　　　　　　　　|
　　　　　　　　　R⁴

N-{D,L-2-(Hydroxyaminocarbonyl)methyl-4-methylpentanoyl}-L-3-(2'-naphthyl)alanyl-L-alanine, 2-(amino)ethyl amide;
N-{D,L-2-(Hydroxyaminocarbonyl)methyl-4-methylpentanoyl}-L-3-amino-2-dimethylbutanoyl-L-alanine, 2-(amino)ethyl amide;
4(S)-[3-Hydroxyaminocarbonyl-2(R)-(2-methylpropyl)propanoyl]amino-1,2,3,4,5-tetrahydro-3H-2-benzazepin-3-one;
[4-(N-Hydroxyamino)-(2R)-isobutyl-3-methylsuccinyl]-L-phenylglycine-N-methylamide;
4(S)-[2(R)-[1(R)-Hydroxycarbamoyl-2-morpholinoethyl]-4-methylvaleryl]amino-1 9,4,5-tetrahydro-3H-2-benzazepine-3-one;
(1R,4S)-4-[(2R)-Hydroxycarbamoylmethyl-4-methylvaleryl]amino-3-oxo-1,2,4,5-tetrahydro-3H-2-benzazepine-1-carboxylic acid;
3-[2-(N-Methylcarbamoyl)ethylsulfinyl]-5-methylhexanohydroxamic acid;
N-[(2-Thenoylmercapto-3-methyl)-butanoyl]-homocysteine thiolactone;
N-[1(R)-Carboxy-ethyl]-α-(S)-(2-phenyl-ethyl)glycine-(L)-leucine, N-phenylamide;
N-[1(R)-Carboxy-ethyl]-α-(S)-(2-phenyl-ethyl)glycine-(L)-isoleucine, N-phenylamide;
N-[1(R)-Carboxy-ethyl]-α-(S)-(2-phenyl-ethyl)glycine-(L)-alanine, N-phenylamide;
N-[1(R)-Carboxy-ethyl]-α-(S)-(2-phenyl-ethyl)glycine-(L)-phenylalanine, N-phenylamide;
N-[1(R)-Carboxy-ethyl]-α-(S)-(2-phenyl-ethyl)glycine-(L)-serine-O-benzyl ether, N-phenylamide;
N-[1(R)-Carboxy-ethyl]-α-(S)-(2-phenyl-ethyl)glycine-(L)-tryptophan, N-phenylamide;
N-[1(R)-Carboxy-ethyl]-α-(S)-(2-phenyl-ethyl)glycine-α-(S)-(2-phenyl-ethyl)glycine, N-phenylamide;
N-[1(R)-Carboxy-ethyl]-α-(S)-(2-phenyl-ethyl)glycine-(L)-norleucine, N-phenylamide;
N-[1(R)-Carboxy-ethyl]-α-(S)-(2-phenyl-ethyl)glycine-(L)-valine, N-phenylamide;
N-[1(R)-Carboxy-ethyl]-α-(S)-(2-phenyl-ethyl)glycine-(L)-serine, N-phenylamide hydrochloride;
N-[1(R)-Carboxy-ethyl]-α-(S)-(2-phenyl-ethyl)glycine-(L)-asparagine, N-phenylamide;
N-[1(R)-Carboxy-ethyl]-α-(S)-(2-phenyl-ethyl)glycine-(L)-threonine, N-phenylamide hydrochloride;
N-[1(R)-Carboxy-ethyl]-α-(S)-(2-phenyl-ethyl)glycine-(L)-lysine, N-phenylamide;
N-[1(R)-Carboxy-ethyl]-α-(S)-(2-phenyl-ethyl)glycine-(L)-glutamic acid, N-phenylamide;
N-[1(R)-Carboxy-ethyl]-α-(S)-(2-phenyl-ethyl)glycine-(L)-tyrosine, N-phenylamide hydrochloride;
N-[1(R)-Carboxy-5-(1,3-dioxo-isoindolin-2-yl)pentyl]-α-(S)-(2-phenyl-ethyl)glycine-(L)-leucine, N-phenylamide;
N-[1(R)-Carboxy-5-(1-oxo-isoindolin-2-yl)pentyl]-α-(S)-(2-phenyl-ethyl)-glycine-(S)-leucine, N-phenylamide hydrochloride;
N-[1(R)-Carboxy-5-(1-oxo-isoindolin-2-yl)pentyl]-α-(S)-(2-phenyl-ethyl)-glycine-(S)-arginine, N-phenylamide;
N-[1(R)-Carboxy-ethyl]-α-(S)-(2-(3-hydroxyphenyl)-ethyl)glycine-(S)-leucine, N-phenylamide hydrochloride;
N-[1(R)-Carboxy-ethyl]-α(S)-(2-(4-methylphenyl)-ethyl)glycine-(S)-leucine, N-phenylamide hydrochloride;
N-[1(R)-Carboxy-ethyl]-α-(S)-(2-(2'-thienyl)ethyl)glycine-(L)-leucine, N-phenylamide;
N-[1(R)-Carboxy-ethyl]-α-(S)-(2-(4-ethylphenyl)ethyl)glycine-(L)-leucine, N-phenylamide;
N-[1(R)-Carboxy-5-(1-oxo-isoindolin-2-yl)pentyl]-α-(S)-(2-(4-propylphenyl)ethyl)glycine-(L)-leucine, N-phenylamide;
N-[1(R)-Carboxy-ethyl]-α-(S)-(2-(4-chlorophenyl)ethyl)glycine-(L)-leucine, N-phenylamide;
N-[1(R)-Carboxy-ethyl]-α-(S)-(2-phenyl-ethyl)glycine-α-(S)-(2-cyclohexyl-ethyl)glycine, N-phenylamide;
N-[1(R)-Carboxy-ethyl]-α-(S)-(2-phenyl-ethyl)glycine-α-(S)-(cyclohexyl)glycine, N-phenylamide;
N-[1(R)-Carboxy-ethyl]-α-(S)-(2-phenyl-ethyl)glycine-α-(S)-(cyclohexylmethyl)glycine, N-phenylamide;
N-[1(R)-Carboxy-ethyl]-α-(S)-(2-phenyl-ethyl)glycine-(L)-β-naphthylalanine, N-phenylamide;
N-[1(R)-Carboxy-ethyl]-α-(S)-(2-phenyl-ethyl)glycine-(L)-α-naphthylalanine, N-phenylamide;
N-[1(R)-Carboxy-ethyl]-α-(S)-(2-phenyl-ethyl)glycine-[(L)-glutamic acid, α,L-bis-N-phenylamide;
N-[1(R)-Carboxy-ethyl]-α-(S)-(2-phenyl-ethyl)glycine-(L)-leucine, N-cyclohexylamide;
N-[(1(R)-Carboxy-ethyl)]-α-(S)-(2-phenyl-ethyl)glycine-α-(S)-(4-hydroxyphenyl-ethyl)glycine, N-phenylamide;
N-[1(R)-Carboxy-ethyl]-α-(S)-(2-phenyl-ethyl)glycine-(L)-phenylglycine, N-phenylamide;
N-[1(R)-Carboxy-ethyl]-α-(S)-(2-phenyl-ethyl)glycine-(L)-glutamic acid, N_L-benzylamide, N_α-phenylamide;
N-[1(R)-Carboxy-ethyl]-α-(S)-(2-phenyl-ethyl)glycine-(L)-ornithine, N-phenylamide;
N-[1(R)-Carboxy-ethyl]-α-(S)-(2-phenyl-ethyl)glycine-(L)-arginine, N-phenylamide;

N-[1(R)-Carboxy-ethyl]-α-(S)-(2-phenyl-ethyl)glycine-α-(S)-(3-phenylpropyl)glycine, N-phenylamide;
N-[1(R)-Carboxy-ethyl]-α-(S)-(2-phenyl-ethyl)glycine-α-(S)-n-octylglycine, N-phenylamide;
N-[1(R)-Carboxy-ethyl]-α-(S)-(2-phenyl-ethyl)glycine-(L)-leucine, N-(4-carboxyphenyl)amide;
N-[1(R)-Carboxy-ethyl]-α-(S)-(2-phenyl-ethyl)glycine-(L)-leucine, N-(4-trifluoromethylphenyl)amide;
N-[1(R)-Carboxy-ethyl]-α-(S)-(2-phenyl-ethyl)glycine-(L)-leucine, N-(3-pyridyl)amide;
N-[1(R)-Carboxy-ethyl]-α-(S)-(2-phenyl-ethyl)glycine-(L)-leucine, N-(benzothiazol-2-yl)amide;
N-[1(R)-Carboxy-ethyl]-α-(S)-(2-(4-n-propylphenyl)ethyl)glycine-(L)-leucine, N-phenylamide;
N-[1(R)-Carboxy-ethyl]-α-(S)-(2-4-propylphenyl)ethyl)glycine-(L)-arginine, N-phenylamide;
N-[1(R)-Carboxy-ethyl]-α-(S)-(2-(3,4-dimethylphenyl-ethyl)glycine-(L)-leucine, N-phenylamide;
(2-(((4-(1,3-Dihydro-1,3-dioxo-2H-isoindol-2-yl)-butyl)hydroxyphosphinyl)methyl)-4-phenylbutanoyl)-L-leucine, N-phenylamide;
(2-(((4-(1,3-Dihydro-1-oxo-2H-isoindol-2-yl)-butyl)hydroxyphosphinyl)methyl)-4-phenylbutanoyl)-L-leucine, N-phenylamide;
(2-(((4-(1,3-Dihydro-1-oxo-2H-isoindol-2-yl)butyl)(2-methyl-1-(1-oxopropoxy)propoxy)phosphinyl)methyl)-4-phenylbutanoyl)-L-leucine, N-phenylamide;
(2-((Hydroxy(methyl)phosphinyl)methyl)-4-phenylbutanoyl)-L-leucine, N-phenylamide;
[[Hydroxy[1(R)-[N-(N-acetyl-L-prolyl-L-alanyl)-amino]-ethyl]-phosphinyl]-methyl]-4-phenyl-butanoyl-L-leucyl, N-phenylamide;
[Hydroxy-[N-(N-(benzoyl)-L-prolyl)aminobutyl]phosphinyl]methyl]-4-phenyl-butanoyl-L-leucine, N-phenylamide;
[Hydroxy-[2-Methylpropyloxycarbonyl-aminobutyl]-phosphinyl]methyl]-4-phenylbutanoyl-L-leucine, N-phenylamide;
[Hydroxy-[1-Methylethylaminocarbonyl-aminobutyl]-phosphinyl]methyl]-4-phenylbutanoyl-L-leucine, N-phenylamide;
N-(2-Thiomethyl-4-phenylbutanoyl)-(L)-leucinamide;
N-(2-Thiomethyl-4-phenylbutanoyl)-(L)-leucine, N-phenylamide;
N-(2-Thiomethyl-4-phenylbutanoyl)-(L)-leucine, N-benzylamide;
N-(2-Thiomethyl-4-phenylbutanoyl)-(L)-leucine, N-(2-phenylethyl)amide;
N-(2-Thiomethyl-4-phenylbutanoyl)-(L)-phenylalaninamide;
N-(2-Thiomethyl-4-phenylbutanoyl)-(L)-phenylalanine N-phenylamide;
N-(2-Thiomethyl-4-phenylbutanoyl)-(L)-phenylalanine N-benzylamide;
N-(2-Thiomethyl-4-phenylbutanoyl)-(L)-phenylalanine-b-alanine;
2(R)-(2-(4-(1-n-Propyl)phenyl)ethyl)-1,5-pentanedioic acid 1-(L-leucine, N-phenylamide)amide;
2(R)-(2-(4-(1-n-Propyl)phenyl)ethyl)-1,5-pentanedioic acid 1-(2(S)-t-butyl)glycine, N-phenylamide)amide;
2(R)-(2-(4-(1-n-Propyl)phenyl)ethyl)-1,5-pentanedioic acid 1-(2(S)-t-butyl)glycine, N-(4-pyridylamide)amide;
2(R)-(2-(4-(1-n-Propyl)phenyl)ethyl)-1,5-pentanedioic acid 1-(L-arginine, N-methylamide)amide;
2(R)-(2-(4-(1-n-Propyl)phenyl)ethyl)-4-methyl-1,5-pentanedioic acid 1-(L-leucine, N-phenylamide)amide;
2(R)-(2-(4-(1-n-Propyl)phenyl)ethyl)-4-methyl-1,5-pentanedioic acid 1-(2(S)-t-butyl)glycine, N-phenylamide)amide;
2(R)-(2-(4-(1-n-Propyl)phenyl)ethyl)-4-methyl-1,5-pentanedioic acid 1-(2(S)-(4-thiazolylmethyl)glycine, N-phenylamide)amide;
2(R)-(2-(4-(1-n-Propyl)phenyl)ethyl)-4-methyl-1,5-pentanedioic acid 1-(2(S)-(3-pyridylmethyl)glycine, N-phenylamide)amide;
2(R)-(2-(4-(1-n-Propyl)phenyl)ethyl)-4-methyl-1,5-pentanedioic acid 1-(L-leucine, N-(4-pyridyl)amide)amide;
2(R)-(2-(4-(1-n-Propyl)phenyl)ethyl)-4-methyl-1,5-pentanedioic acid 1-(2(S)-(2-pyridylmethyl)glycine, N-phenylamide)amide;
2(R)-(2-(4-(1-n-Propyl)phenyl)ethyl)-4-methyl-1,5-pentanedioic acid 1-(L-arginine, N-phenylamide)amide;
2(R)-(2-(4-(1-n-Propyl)phenyl)ethyl)-4-methyl-1,5-pentanedioic acid 1-(L-phenylalanine, N-4-pyridylamide)amide;
2(R)-(2-(4-(1-n-Propyl)phenyl)ethyl)-4-(1-(4-(N-(2-oxoisoindolinyl))-butyl))-1,5-pentanedioic acid 1-(L-leucine, N-phenylamide)amide;
2(R)-(2-(4-(1-n-Propyl)phenyl)ethyl)-4-(1-(4-(N-(2-oxoisoindolinyl))-but-2-enyl))-1,5-pentanedioic acid 1-(L-leucine, N-phenylamide)amide;
2(R)-(2-(4-(4-Fluorophenyl)phenyl)ethyl)-4-methyl-1,5-pentanedioic acid 1-(L-leucine, N-phenylamide)amide;
2(R)-(2-(4-(Phenyl)phenyl)ethyl)-4-methyl-1,5-pentanedioic acid 1-(L-leucine, N-phenylamide)amide;
2(R)-(2-(4-(4-Methoxyphenyl)phenyl)ethyl)-4-methyl-1,5-pentanedioic acid 1-(L-leucine, phenylamide)amide;
2(R)-(2-(4-(4-Methylphenyl)phenyl)ethyl)-4-methyl-1,5-pentanedioic acid 1-(L-leucine, phenylamide)amide;
2(R)-(2-(4-(4-Hydroxy-n-butyl)-phenyl)-ethyl)-4-methylpentanedioic acid 1-(S-leucine, phenylamide)amide;
2(R),4(S)-(2-(4-(3-Hydroxy-n-propyl)phenyl)ethyl)-4-methyl-1,5-pentanedioic acid 1-(L-leucine, N-phenylamide)amide;
2(R)-(2-Phenylethyl)-4-methyl-1,5-pentanedioic acid 1-(L-leucine, N-phenylamide)amide;
2(R)-(2-(4-(1-n-Propyl)phenyl)ethyl)-1,5-pentanedioic acid 1-(L-leucine, N-ethylamide)amide;
2(R)-(2-(4-(1-n-Propyl)phenyl)ethyl)-1,5-pentanedioic acid 1-(L-leucine, N-isopropylamide)amide;
2(R)-(2-(4-(1-n-Propyl)phenyl)propyl)-1,5-pentanedioic acid 1-(2(S)-tert-butyl-glycine, N-4-pyridyl)amide)amide;
2(R)-(3-(4-(1-n-Propyl)phenyl)propyl)-1,3-pentanedioic acid 1-(L-leucine, N-phenylamide)amide;
2(R)-(2-(4-(1-n-Propyl)phenyl)ethyl)-4-hexyl-1,5-pentanedioic acid 1-(L-leucine, N-phenylamide)amide;
2(R)-(2-(4-(1-n-Propyl)phenyl)ethyl)-4-butyl-1,5-pentanedioic acid 1-(L-leucine, N-phenylamide)amide;
2(R)-(2-(4-(1-n-Propyl)phenyl)ethyl)-4-(3-methylbenzyl)-1,5-pentanedioic acid 1-(L-leucine, N-phenylamide)amide;
2(R)-(2-(4-(1-n-Propyl)phenyl)ethyl)-4-(4-(2-benzimidazolyl)butyl)-1,5-pentanedioic acid 1-(L-leucine, N-phenylamide)amide;
2(R)-(2-(4-(1-n-Propyl)phenyl)ethyl)-4-(4-(2-benzthiazolyl)butyl)-1,5-pentanedioic acid 1-(L-leucine, N-phenylamide)amide;
2(R)-(2-(4-(1-n-Propyl)phenyl)ethyl)-4-(4-(2-benzoxazolyl)butyl)-1,5-pentanedioic acid 1-(L-leucine, N-phenylamide)amide;
2(R)-(2-(4-(1-n-Propyl)phenyl)ethyl)-4-carboxy-1,9-nonanedioic acid 1-(L-leucine, N-phenylamide)amide 9-piperidineamide;

2(R)-(2-(4-(1-Propyl)phenyl)ethyl)-4-carboxy-1,9-nonanedioic acid 1-(L-leucine, N-methylamide)amide 9-phenylamide;

2(R)-(2-(4-(1-n-Propyl)phenyl)ethyl)-4-carboxy-1,9-nonanedioic acid 1-(L-leucine, N-methylamide)amide 9-tert-butylamide;

2(R)-(2-(4-(1-n-Propyl)phenyl)ethyl)-4-carboxy-1,9-nonanedioic acid 1-(L-leucine, N-methylamide)amide 9-benzylamide;

2(R)-(2-(4-(1-n-Propyl)phenyl)ethyl)-4-carboxy-1,9-nonanedioic acid 1-(L-leucine, N-methylamide)amide 9-morpholineamide;

2(R)-(2-(4-(1-n-Propyl)phenyl)ethyl)-4-carboxy-1,9-nonanedioic acid 1-(L-leucine, N-methylamide)amide 9-(1(R)-phenylethyl)amide;

2(R)-(2-(4-(1-n-Propyl)phenyl)ethyl)-4-carboxy-1,9-nonanedioic acid 1-(L-leucine, N-methylamide)amide 9-(1(S)-phenylethyl)amide;

2(R)-(2-(4-(1-n-Propyl)phenyl)ethyl)-4-carboxy-1,9-nonanedioic acid 1-(L-leucine, N-methylamide)amide 9-(N-methyl-N-phenyl)amide;

2(R)-(2-(4-(1-n-Propyl)phenyl)ethyl)-4-carboxy-1,9-nonanedioic acid 1-(L-leucine, N-methylamide)amide 9-(N'-methylpiperazine)amide trifluoroacetic acid salt;

2(R)-(2-(4-(1-n-Propyl)phenyl)ethyl)-4-carboxy-1,9-nonanedioic acid 1-(L-leucine, N-methylamide)amide 9-(3-pyridyl)amide;

2(R)-(2-(4-(1-Propyl)phenyl)ethyl)-4-carboxy-1,9-nonanedioic acid 1-(L-leucine, N-methylamide)amide;

2(R)-(2-(4-(1-Propyl)phenyl)ethyl)-1,5-pentanedioic acid 1-((R)-(S-p-methoxybenzyl)penicillamine, N-phenylamide)amide;

2(R)-(2-(4-(1-Propyl)phenyl)ethyl)-1,5-pentanedioic acid 1-((R)-(S-p-methoxybenzyl)penicillamine sulfone, N-phenylamide)amide;

2-(2-(4-(1-Propyl)phenyl)ethyl)-4-(1-(4-(2-phthalimido))butyl)-1,5-pentandioic acid 1-(L-leucine, N-methylamide)amide;

2(R)-(2-(4-(1-n-Propyl)phenyl)ethyl)-4-(4-benzoylamino-1-butyl)-1,5-pentandioic acid 1-(L-leucine, N-methylamide)amide;

2(R)-(2-(4-(-n-Propyl)phenyl)ethyl)-4-(4-pivaloylamino-1-butyl)-1,5-pentandioic acid 1-(L-leucine, N-methylamide)amide;

2(R)-(2-(4-(1-n-Propyl)phenyl)ethyl)-4-(4-phenylsulfonylamino-1-butyl)-1,5-pentandioic acid 1-(L-leucine, N-methylamide)amide;

2(R)-(2-(4-(1-n-Propyl)phenyl)ethyl)-4-(4-(N'-phenylureido)-1-butyl)-1,5-pentandioic acid 1-(L-leucine, N-methylamide)amide;

2(R)-(2-(4-(1-n-Propyl)phenyl)ethyl)-4-(4-phenyloxycarbonylamino-1-butyl)-1,5-pentandioic acid 1-(L-leucine, N-methylamide)amide;

2(R)-(2-(4-(1-n-Propyl)phenyl)ethyl)-4-(4-N'-benzyloxycarbonylamino-L-prolylamino)-1-butyl)-1,5-pentandioic acid 1-(L-leucine, N-methylamide)amide;

2(R)-(2-(4-(1-n-Propyl)phenyl)ethyl)-4-(4-cyclopentylamino-1-butyl)-1,5-pentandioic acid 1-(L-leucine, N-methylamide)amide;

2(R)-(2-(4-(1-n-Propyl)phenyl)ethyl)-4-(4-(2-carboxybenzoylamino)-1-butyl)-1,5-pentandioic acid 1-(L-leucine, N-methylamide)amide;

2(R)-(2-(4-(1-n-Propyl)phenyl)ethyl)-4-(4-cyano-1-butyl)-1,5-pentandioic acid 1-(L-leucine, N-phenylamide)amide;

N-[1(R)-Carboxyethyl]-α-(S)-(9-amino-n-nonyl)]glycine-(L)-leucine, N-phenylamide;

N-[1(R)-Carboxyethyl]-α-(S)-(n-octyl)]glycine-(L)-leucine, N-phenylamide;

N-[1(R)-Carboxyethyl]-α-(S)-(n-octyl)]glycine-(L)-arginine, N-phenylamide;

N-[1(R)-Carboxyethyl]-α-(S)-(9-amino-n-nonyl)]glycine-(L)-arginine, N-phenylamide;

N-[1(R)-Carboxyethyl]-α-(S)-(n-decyl)]glycine-(L)-leucine, N-phenylamide;

1-(2-(4-Propylphenyl)ethyl)cyclopentane-1,3-dicarboxylic acid 1-(L-leucine, N-phenylamide)amide;

1-(2-(4-Propylphenyl)ethyl)cyclohexane-1,3-dicarboxylic acid 1-(L-leucine, N-phenylamide)amide;

N-[1(R)-Carboxyethyl]-α-(S)-2-(4-fluorobiphenyl)-glycyl-(S)-2-(tert-butyl)glycine, N-phenylamide;

3S-[4-(N-Hydroxyamino)-2R-isobutylsuccinyl]amino-1-methoxy-3,4-dihydrocarbostyril;

3S-[4-(N-Hydroxyamino)-2R-isobutyl-3S-acetylthiomethylsuccinyl]amino-3,4-dihydrocarbostyril;

3S-[4-(N-Hydroxyamino)-2R-isobutyl-3S-methylsuccinyl]amino-1-methoxy-3,4-dihydrocarbostyril;

3S-[4-(N-Hydroxyamino)-2R-isobutylsuccinyl]amino-1-methoxymethyl-3,4-dihydrocarbostyril;

1-Carboxymethyl-3S-[4-N-hydroxyamino)-2R-isobutyl-3S-methylsuccinyl]amino-3,4-dihydrocarbostyril;

3S-[4-(N-Hydroxyamino)-2R-isobutylsuccinyl]amino-1-methoxyethoxymethyl-3,4-dihydrocarbostyril;

3S-[4-(N-Hydroxyamino)-2R-heptylsuccinyl]amino-1-methoxy-3,4-dihydrocarbostyril;

7-Chloro-3S-[4-(N-hydroxyamino)-2R-isobutylsuccinyl]amino-1-methoxymethyl-3,4-dihydrocarbostyril;

3S-[4-(N-Hydroxyamino)-2R-isobutylsuccinyl]amino-1-methoxyethyl-3,4-dihydrocarbostyril;

3S-[4-(N-Hydroxyamino)-2R-isobutylsuccinyl]amino-1-methoxyethyl-6,7-methylenedioxy-3,4-dihydrocarbostyril;

3R-[4-(N-Hydroxyamino)-2R-isobutylsuccinyl]amino-1-methoxyethyl-6,7-methylenedioxy-3,4-dihydrocarbostyril;

2-(R)-N-Hydroxy-2-[(4-methoxybenzenesulfonyl)(3-morpholin-4-yl-3-oxopropyl)amino]-3-methylbutyramide;

2-(R)-2-[(2-Benzylcarbamoylethyl)(4-methoxybenzenesulfonyl)amino]-N-hydroxy-3-methylbutyramide;

2-(R)-N-Hydroxy-2-((4-methoxybenzenesulfonyl) (2-[(pyridin-3-ylmethyl)carbamoyl]ethyl)amino)-3-methylbutyramide;

2-(R)-N-Hydroxy-2-([4-methoxybenzenesulfonyl]-[2-(methylpyridin-3-ylmethylcarbamoyl)ethyl]amino)-3-methylbutyramide;

4-(3-[1-(R)-1-Hydroxycarbamoyl-2-methylpropyl)-(4-methoxybenzenesulfonyl)amino]propionyl)piperazine-1-carboxylic acid, tert-butyl ester;

2-(R)-N-Hydroxy-2-[(4-methoxybenzenesulfonyl)-(3-oxo-3-piperazin-1-ylpropyl)amino]-3-methylbutyramide hydrochloride;

2-(R)-2-[(Benzylcarbamoylethyl)(4-methoxybenzenesulfonyl)amino]-N-hydroxy-3-methylbutyramide;

2-(R)-N-Hydroxy-2-[(4-methoxybenzenesulfonyl]-[(2-morpholin-4-ylethylcarbamoyl)methyl]amino]-3-methylbutyramide;

2-(R)-N-Hydroxy-2-((4-methoxybenzenesulfonyl)([(pyridin-3-ylmethyl)carbamoyl]methyl)amino)-3-methylbutyramide;

2-(R)-3,3,3,-Trifluoro-N-hydroxy-2-[(methoxybenzenesulfonyl)(3-morpholin-4-yl-3-oxopropyl)amino]propionamide;

2-(R)-N-Hydroxy-2-((4-phenoxybenzenesulfonyl)-[2-methylpyridin-4-ylmethylcarbamoyl)ether]amino)-3-methylbutyramide;

4-[4-Methoxybenzenesulfonyl)(3-morpholin-4-yl-3-oxopropyl)amino]-1-methylpiperidene-4-carboxylic acid hydroxyamide;

2-(R)-N-Hydroxy-2-((4-methoxybenzenesulfonyl)-[3-(4-methylpiperazin-1-yl)-3-oxopropyl]amino)-3-methylbutyramide;

2-(R)-2-[(2-Carboxyethyl)(4-methoxybenzenesulfonyl)amino]-N-hydroxy-3-methylbutyramide;

[(2-Carboxyethyl)(3,4-dimethoxybenzene-sulfonyl)-amino]-N-hydroxy-acetamide;

2-(R)-2-[(2-Carbamoylethyl)(4-methoxybenzene-sulfonyl)amino]-N-hydroxy-3-methylbutyramide;

2-(R), 3-(R)-3, N-Dihydroxy-2-[(4-methoxybenzene-sulfonyl)(3-oxo-3-piperidin-1-ylpropyl)amino]-butyramide;

2-(R)-N-Hydroxy-2-((4-methoxybenzenesulfonyl)-[3-(methylpyridin-3-ylmethylcarbamoyl)propyl]amino)-3-methylbutyramide;

2-(R)-N-Hydroxy-2-((4-methoxybenzenesulfonyl)-[2-(methylcarboxymethylcarbamoyl)ethyl]amino)-3-methyl-butyramide;

2-(R)-N-Hydroxy-2-((4-methoxybenzenesulfonyl) -[(1-methylpiperidin-4-ylcarbamoyl)methyl]amino)-3-methylbutyramide;

2-(R)-N-Cyclohexyl-N-hydroxy-2-((4-methoxybenzenesulfonyl)-[3-(4-methylpiperazin-1-yl)-3-oxopropyl]amino)-acetamide;

2-(R)-N-Hydroxy-2-[(methoxybenzenesulfonyl)(3-morpholin-4-yl-[3-oxopropyl)amino]-4-(morpholin-4-yl)butyramide;

[4-N-Benzyloxyamino)-2(R)-isobutylsuccinyl]-L-leucyl-L-alanine ethyl ester;

[4-N-Benzyloxyamino)-2(R)-isobutylsuccinyl]-3(RS)-aminolaurolactam;

$N^a$-[4-(N-Benzyloxyamino)-2(R)-isobutylsuccinyl]-$N^e$-(N-benzyloxycarbonylglycyl)-L-lysyl-L-alanine ethyl ester;

[4-(N-Hydroxyamino)-2(RS)-isobutylsuccinyl]-L-leucylglycine ethyl ester;

[4-(N-Hydroxyamino)-2(RS)-isobutylsuccinyl]-L-leucylglycine isopentylamide;

[4-(N-Hydroxyamino)-2(RS)-isobutylsuccinyl]-L-valylglycine ethylamide;

[4-(N-Hydroxyamino)-2(RS)-isobutylsuccinyl]-L-leucylglycine ethylamide;

$N^a$-[4-(N-Hydroxyamino)-2(RS)-isobutylsuccinyl]-$N^e$-tert.butoxycarbonyl-L-lysylglycine ethylamide;

[4-(N-Hydroxyamino)-2(RS)-isobutylsuccinyl]-O-methyl-L-tyrosinylglycine ethyl ester;

[4-(N-Hydroxyamino)-2(RS)-isobutylsuccinyl]-O-methyl-L-tyrosinylglycine ethylamide;

[4-(N-Hydroxyamino)-2(RS)-isobutylsuccinyl]-L-leucyl-L-alanine ethyl ester;

[4-(N-Hydroxyamino)-2(RS)-isobutylsuccinyl]-L-leucylglycine isopentyl ester;

[4-(N-Hydroxyamino)-2(R)-propyisuccinyl]-L-leucylglycine ethyl ester;

[4-(N-Hydroxyamino)-2(RS)-sec.butylsuccinyl]-L-leucylglycine ethyl ester;

[4-(N-Hydroxyamino)-2(RS)-isobutylsuccinyl]-L-leucyl-L-alanine;

[4-(N-Hydroxyamino)-2(RS)-isobutylsuccinyl]-L-leucylglycine methyl ester;

[4-(N-Hydroxyamino)-2(RS)-isobutylsuccinyl]-L-leucylsarconsine ethyl ester;

[4-(N-Hydroxyamino)-2(RS)-isobutylsuccinyl]-L-leucyl-L-proline ethyl ester;

[4-(N-Hydroxyamino)-2(RS)-isobutylsuccinyl]-L-leucine-L-alanine isopropyl ester;

[4-(N-Hydroxyamino)-2(RS)-isobutylsuccinyl]-L-leucine-2-oxopropylamide;

[4-(N-Hydroxyamino)-2(RS)-isobutylsuccinyl]-L-leucine-2-methoxyethylamide;

[4-(N-Hydroxyamino)-2(RS)-isobutylsuccinyl]-L-leucine-2,2-dimethoxyethylamide;

$N^a$-[4-(N-Hydroxyamino)-2(R)-isobutylsuccinyl]-$N^e$-glycyl-L-lysine methylamide;

$N^a$-[4-(N-Hydroxyamino)-2(R)-isobutylsuccinyl]-$N^e$-(4-carboxybenzoyl)-L-lysl-L-alanine ethyl ester;

$N^a$-[4-(N-Hydroxyamino)-2(R)-isobutylsuccinyl]-$N^e$-(4-carboxybenzoyl)-L-lysyl-L-aline;

[4-(N-Hydroxyamino)-2(R)-isobutylsuccinyl]-3(RS)-aminooctahydro-2H-azonin-2-one;

[4-(N-Hydroxyamino)-3(S )-methyl-2(R)-isobutyl-succinyl]-L-leucylglycine ethyl ester;

[(3-Aminophthalimido)methyl][(RS)-4-methyl-2-[[(S)3-methyl-1-(methylcarbamoyl)butyl]carbamoyl]pentyl] phosphinic acid;

[(RS)-4-Methyl-2-[[(S)-3-methyl-1-(methylcarbamoyl)butyl]carbamoyl]pentyl](1,8-naphthalenedicarboximidomethyl)phosphinic acid;

[(R or S)-4-Methyl-2-[[(R or S)-2-oxo-3-azacyclotridecyl]carbamoyl]pentyl](1.8-naphthalenedicarboximidomethyl)phosphinic acid;

N-[N-[(R or S)-2[[[[[N-[1-(Benzyloxy)carbonyl]-L-prolyl]-L-leucyl]amino]methyl]hydroxyphosphinyl]-methyl]-4-methylvaleryl]-L-leucyl]-L-alanine;

[[1,4-Dihydro-2,4-dioxo-3(2H)-quinazolinyl]-methyl][[(R or S)-4-methyl-2-[[(R or S)-2-oxo-3-azacyclotridecyl]carbamoyl]pentyl]phosphinic acid;

$N^{2-}$[(R)-Hydroxycarbamoylmethyl]-4-methylvaleryl]-$N^1$,3-dimethyl-L-valinamide;

$N^{2-}$[2(R or S)-[[[(5-Bromo-2,3-dihydro-6-hydroxy)-1,3-dioxo-1H-benz[d,e]isoquinol-2-yl)methyl]-[(hydroxy)phosphinyl]methyl]-4-methylvaleryl]-$N^1$,3-dimethyl-L-valinamide;

$N^{2-}$[(R or S)-[[(R)-(Amino)[(5-bromo-2,3-dihydro-6-hydroxy-1,3-dioxo-1H-benz[d,e]isoquinol-2-yl)methyl](hydroxy)phosphinyl]methyl]-4-methylvaleryl]-$N^3$,1-dimethyl-L-valinamide hydrobromide;

$N^{2-}$[2(R or S)-[1(S)-(Hydroxycarbamoyl)ethyl-4-methylvaleryl]-$N^1$,3-dimethylvalinamide;

$N^{2-}$[2(R)-[1(R or S)-(Hydroxycarbamoyl)-2-phthalimidoethyl]-4-methylvaleryl]-$N^1$,3-dimethyl-L-valinamide;

$N^{2-}$[2(R)-[1(R or S)-(Hydroxycarbamoyl)-4-(methoxycarbonyl)butyl]-4-methylvaleryl]-$N^1$,3-dimethyl-L-valinamide;

$M^{2-}$[2(R)-[1(R or S)-(Hydroxycarbamoyl)-4-phenyl-butyl]-4-methylvaleryl]-$N^1$,3-dimethyl-L-valinamide;

$N^{2-}$[2(R)-[1(R or S)-(Hydroxycarbamoyl)-2-succinimidoethyl]-4-methylvaleryl]-$N^1$, 3-dimethyl-L-valinamide;

4-[2(R)-[1(R or S)-(Hydroxycarbamoyl)-2-phthalimidoethyl]-4-methylvaleryl]morpholine;

4-[2(R)-[1(R or S)-(Hydroxycarbamoyl)-2-phthalimidoethyl]-4-methylvaleryl]tetrahydro-1,4-thiazine;

1-[2(R)-[1(R or S)-(Hydroxycarbamoyl)-2-phthalimidoethyl]-4-methylvaleryl]-4-piperidinol;

1-[2(R)-[1(R or S)-(Hydroxycarbamoyl)-2-(1,2-dimethyl-3,5-dioxo-1,2,4-triazolidin-4-yl)ethyl]-4-methylvaleryl]piperidine;

4-[2(R)-[1(R or S)-(Hydroxycarbamoyl)-2-(3-methyl-2,5-dioxo-1-imidazolidinyl)ethyl]-4-methylvaleryl] tetrahydro-1,4-thiazine;

Hexahydro-2-[2(R)-[1(R or S)-(hydroxycarbamoyl)-2-phthalimidoethyl]-4-methylvaleryl]-N-methyl-3(S)-pyridazinecarboxamide;

1-[2(R)-(R or S)-(Hydroxycarbamoyl)-2-(3,4,4-trimethyl-2,5-dioxo-1-imidazolidinyl)ethyl]-4-methylvaleryl]-4-piperidinol;

[4-(N-Hydroxyamino)-2(R or S)-heptylsuccinyl]-L-leucyl-L-leucine ethyl amide;

[4-(N-Hydroxyamino)-2(R or S)-nonylsuccinyl]-L-leucyl-L-leucine ethylamide;

[4-(N-Hydroxyamino)-2(R or S)-heptyl-3(S)-methylsuccinyl]-L-leucyl-L-leucine ethylamide;

[4-(N-Hydroxyamino)-2(R)-heptyl-3(R or S)-(phthalimidomethyl)succinyl]-L-leucyl-L-leucine ethylamide;

[4-(N-Hydroxyamino)-2(RS)-nonylsuccinyl]-L-tert.butylglycine methylamide;

[4-(N-Hydroxyamino)-2(RS)-heptylsuccinyl]-L-phenylalanine methylamide;

[4-(N-Hydroxyamino)-2(R)-heptyl-3(R or S)-phthalimidomethyl)succinyl]-L-tert.butylglycine methylamide;

[4-(N-Hydroxyamino)-2(R)-heptyl-3(R or S)-(3-phenylpropyl)-succinyl]-L-leucyl-L-leucine ethylamide;

[4-(N-Hydroxyamino)-2(RS)-heptylsuccinyl]-L-leucine methylamide;

[4-(N-Hydroxyamino)-2(RS)-heptylsuccinyl]-L-leucine neopentylamide;

[4-(N-Hydroxyamino)-2(RS)-heptylsuccinyl]-L-alanyl-L-leucine ethylamide;

[4-(N-Hydroxyamino)-2(RS)-heptylsuccinyl]-L-(N$^e$-phthaloyl)-lysyl-L-leucine ethylamide;

[4-(N-Hydroxyamino)-2(RS)-undecylsuccinyl]-L-leucyl-L-leucine ethylamide;

[4-(N-Hydroxyamino)-2(RS)-heptylsuccinyl]-L-phenylalanyl-L-leucine ethylamide;

[4-(N-Hydroxyamino)-2(RS)-heptylsuccinyl]-L-nonalyl-L-leucine ethylamide;

[4-(N-Hydroxyamino)-2(RS)-heptylsuccinyl]-phenylalanine tert.butylamide;

[4-(N-Hydroxyamino)-2(RS)-heptylsuccinyl]-L-tertbutylglycine methylamide;

[4-(N-Hydroxyamino)-2(RS)-heptylsuccinyl]-L-neopentylglycine methylamide;

[4-(N-Hydroxyamino)-2(RS)-heptylsuccinyl]-L-homophenylalanyl-L-leucine ethylamide;

[4-(N-Hydroxyamino)-2(RS)-heptylsuccinyl]-L-cyclohexylalanine methyl amide;

[4-(N-Hydroxyamino)-2(RS)-isooctylsuccinyl]-L-phenylalanine methylamide;

[4-(N-Hydroxyamino)-2(R)-heptylsuccinyl]-L-neonpentylglycine methylamide;

[4-(N-Hydroxyamino)-2(R)-heptylsuccinyl]-(D or L)-β,β-dimethylphenylalanine methylamide;

[4-(N-Hydroxyamino)-2(R)-heptylsuccinyl]-(D or L)-threo-β-methylphenylalanine methylamide;

[4-(N-Hydroxyamino)-2(R)-heptylsuccinyl]-DL-erthro-β-methylphenylalanine methylamide;

[4-(N-Hydroxyamino)-2(R)-heptyl-3(R or S)-[(3-methyl-2,5-dioxo-1-imidazolidinyl)methyl]succinyl]-L-leucyl-L-leucine ethylamide;

N2-[3-Cyclobutyl-2(R or S)-[(hydroxycarbamoyl)-methyl]-propionyl]-N1,3-dimethyl-L-valinamide;

N2-[3-Cyclopropyl-2(R or S)-[(hydroxycarbamoyl)-methyl]-propionyl]-N1,3-dimethyl-L-valinamide;

N2-[3-Cyclopentyl-2(R or S)-[(hydroxycarbamoyl)-methyl]-propionyl]-N1,3-dimethyl-L-valinamide;

N2-[3-Cyclopropyl-2(R)-[1(R or S)-[(hydroxy-carbamoyl)-2-(3,4,4-trimethyl-2,5-dioxo-1-imidazolidinyl)ethyl] propionyl]-N1,3-dimethyl-L-valinamide;

N2-[3-Cyclopropyl-2(R)-[1(R or S)-[(hydroxy-carbamoyl)-4-phenylbutyl)]propionyl]-N1,3-dimethyl-L-valinamide;

N2-[3-Cyclobutyl-2(R)-[1(R or S)-(hydroxy-carbamoyl)-4-phenylbutyl]propionyl]-N1,3-dimethyl-L-valinamide;

N2-[3-Cyclopentyl-2(R)-[1(R or S)-(hydroxycarbamoyl)-4-phenylbutyl]propionyl]-N1,3-dimethyl-L-valinamide;

1-[3-Cyclopropyl-2(R)-[1(R or S)-(hydroxy-carbamoyl)-2-(3,4,4-trimethyl-2,5-dioxo-1-imidazolidinyl)ethyl] propionyl]piperidine;

1-[3-Cyclopropyl-2(R)-[1(R or S)-(hydroxy-carbamoyl)-2-(3,4,4-trimethyl-2,5-dioxo-1-imidazolidinyl)ethyl] propionyl]-4-piperidinol;

1-[3-Cyclobutyl-2(R)-[1(R or S)-(hydroxy-carbamoyl)-2-(3,4,4-trimethyl-2,5-dioxo-1-imidazolidinyl)ethyl] propionyl]piperidine;

1-[3-Cyclobutyl-2(R)-[1(R or S)-(hydroxy-carbamoyl)-2-(3,4,4-trimethyl-2,5-dioxo-1-imidazolidinyl)ethyl] propionyl]-4-piperidinol;

1-[3-Cyclopentyl-2(R)-[1(R or S)-(hydroxy-carbamoyl)-2-(3,4,4-trimethyl-2,5-dioxo-1-imidazolidinyl)ethyl] propionyl]-4-piperidinol;

1-[3-Cyclopentyl-2(R)-[1(R or S)-(hydroxy-carbamoyl)-2-(3,4,4-trimethyl-2,5-dioxo-1-imidazolidinyl)ethyl] propionyl]piperidine;

3-[3-Cyclobutyl-2(R)-[1(R or S)-(hydroxycarbamoyl)-2-(3,4,4-trimethyl-2,5-dioxo-1-imidazolidinyl)ethyl] propionyl]-3-azabicyclo[3.2.2]nonane;

3-[3-Cyclopropyl-2(R)-[1(R or S)-(hydroxy-carbamoyl)-2-(3,4,4-trimethyl-2,5-dioxo-1-imidazolidinyl)ethyl] propionyl]-3-azabicyclo[3.2.2]nonane;

3-[3-Cyclopentyl-2(R)-[1(R or S)-(hydroxy-carbamoyl)-2-(3,4,4-trimethyl-2,5-dioxo-1-imidazolidinyl)ethyl] propionyl]-3-azabicyclo[3.2.2]nonane;

1-[3-Cyclohexyl-2(R)-[1(R or S)-(hydroxycarbamoyl)-2-(3,4,4-trimethyl-2,5-dioxo-1-imidazolidinyl)ethyl] propionyl]piperidine;

4-[3-Cyclopentyl-2(R)-[1 (R or S)-(hydroxycarbamoyl)-2-(3,4,4-trimethyl-2,5-dioxo-1-imidazolidinyl)ethyl] propionyl]tetrahydro-1,4-thiazine;

4-[3-Cyclopentyl-2(R)-[1(R or S)-(hydroxycarbamoyl)-2-(3,4,4-trimethyl-2,5-dioxo-1-imidazolidinyl)ethyl] propionyl]tetrahydro-1,4-thiazine S,S-dioxide;

4-[3-Cyclobutyl-2(R)-[1(R or S)-(hydroxycarbamoyl)-2-(3,4,4-trimethyl-2,5-dioxo-1-imidazolidinyl)ethyl] propionyl]tetrahydro-1,4-thiazine;

3-[3-Cyclopentyl-2(R)-[1(R or S)-(hydroxycarbamoyl)-2-(3,4,4-trimethyl-2,5-dioxo-1-imidazolidinyl)ethyl] propionyl]-5,5-dimethyl-N-propyl-[4(R)-thiazolidinecarboxamide;

4-[3-Cyclopentyl-2(R)-[1(R or S)-(hydroxycarbamoyl)-2-(3,4,4-trimethyl-2,5-dioxo-1-imidazolidinyl)ethyl] propionyl]morpholine;

3-[3-Cyclopentyl-2(R)-[1(R or S)-(hydroxycarbamoyl)-2-(3,4,4-trimethyl-2,5-dioxo-1-imidazolidinyl)ethyl] propionyl]-N,5,5-trimethyl-4(R)-thiazolidinecarboxamide;

4-[3-Cyclobutyl-2(R)-[1(R or S)-(hydroxycarbamoyl)-2-(3,4,4-trimethyl-2,5-dioxo-1-imidazolidinyl)ethyl] propionyl]-4-phenylpiperazine;

4-[3-Cyclobutyl-2(R)-[1(R or S)-(hydroxy-carbamoyl)-2-(3,4,4-trimethyl-2,5-dioxo-1-imidazolidinyl)ethyl] propionyl]morpholine;

1-[3-Cyclobutyl-2(R)-[1(R or S)-(hydroxy·carbamoyl)-2-(3,4,4-trimethyl-2,5-dioxo-1-imidazolidinyl)ethyl]propionyl]pyrrolidine;

8-[3-Cyclobutyl-2(R)-[1(R or S)-(hydroxycarbamoyl)-2-(3,4,4-trimethyl-2,5-dioxo-1-imidazolidinyl)ethyl]propionyl]-1,4-dioxa-8-azaspiro[4,5]decane;

1-[3-Cyclobutyl-2(R)-[1(R or S)-(hydroxycarbamoyl)-2-(3,4,4-trimethyl-2,5-dioxo-1-imidazolidinyl)ethyl]propionyl]-4-methoxypiperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]octahydroazocine;

1-[3-Cyclobutyl-2(R)-[1(R or S)-(hydroxycarbamoyl)-2-(5,5-dimethyl-2,4-dioxo-3-oxazolidinyl)ethyl]propionyl]piperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]hexahydroazepine;

1-[3-Cyclobutyl-2(R)-[2-(hexahydro-1,3-dioxo-pyrazolo[1,2-a][1,2,4]triazol-2-yl)-1(R or S)-(hydroxycarbamoyl)ethyl]propionyl]piperidine;

1-[3-Cyclobutyl-2(R)-[1(R or S)-(hydroxycarbamoyl)-2-phthalimidoethyl]propionyl]piperidine;

2-[2(R)-[1(R or S)-(Hydroxycarbamoyl)-4-phenylbutyl]nonanoyl]-hexahydro-N-methyl-3(S)-pyridazinecarboxamide;

N-Cyclohexyl-hexahydro-2-[2(R)-[1(RS)-(hydroxycarbamoyl)-4-phenylbutyl]nonanoyl]-3(S)-pyridazinecarboxamide;

Hexahydro-2-[2(R)-[1(RS)-(hydroxycarbamoyl)-4-phenylbutyl]nonanoyl]-N-(2,2,6,6-tetramethyl-4-piperidinyl)-3(S)-pyridazinecarboxamide;

1-[2(R)-[1(R or S)-Hydroxycarbamoyl)-4-phenylbutyl]nonanoyl]piperidine;

N2-[2(R)-[1(RS)-(Hydroxycarbamoyl)-2-(3,4,4-trimethyl-2,5-dioxo-1-imidazolidinyl)ethyl]nonanoyl]-N1-methyl-L-prolinamide;

1-[2(R)-[1(R or S)-(Hydroxycarbamoyl)-2-(3,4,4-trimethyl-2,5-dioxo-1-imidazolidinyl)ethyl]nonanoyl]piperidine;

Hexahydro-2-[2(R)-1(R or S)-(hydroxycarbamoyl)-2-(3,4,4-trimethyl-2,5-dioxo-1-imidazolidinyl)ethyl]nonanoyl]-N-methyl-3(S)-pyridazinecarboxamide;

Hexahydro-2-[2(R or S)-[1(S)-(hydroxycarbamoyl)-3-phenylpropyl]undecanoyl]-N-methyl-3(S)-pyridazinecarboxamide;

Hexahydro-2-[2(R or S)-[1(S)-(hydroxycarbamoyl)-3-phenylpropyl]undecanoyl]-N-methoxy-N-methyl-3(S)-pyridazinecarboxamide;

Hexahydro-2-[2(R or S)-[(1(S)-(hydroxycarbamoyl)-3-phenylpropyl]-undecanoyl]-N-(1,2,2,6,6-pentamethyl-4-piperidinyl)-3(S)-pyridazinecarboxamide;

Hexahydro-2-[2(R or S)-[1(S)-(hydroxycarbamoyl)ethyl]undecanoyl]-N-methyl-3(S)-pyridazinecarboxamide;

Hexahydro-2-[2(R or S)-[1(S)-(hydroxycarbamoyl)-3-phenylpropyl]nonanoyl]-N-methyl-3(S)-pyridazinecarboxamide;

Hexahydro-2-[2(R or S)-[1(S)-(hydroxycarbamoyl)ethyl]nonanoyl]-N-methyl-3(S)-pyridazinecarboxamide;

1-[2(R or S)-[1(S)-(Hydroxycarbamoyl)ethyl]undecanoyl]piperidine;

1-[2-(R or S)-[1(S)-(hydroxycarbamoyl)-3-phenylpropyl]undecanoyl]piperidine;

Hexahydro-2-[2(R or S)-[1(S)-(hydroxycarbamoyl)-3-phenylpropyl]-undecanoyl]-N-(2,2,6,6-tetramethy-4-piperidinyl)-3(S)-pyridazinecarboxamide;

Hexahydro-2-[2(R or S)-[1(S)-(hydroxycarbamoyl)ethyl]undecanoyl]-N-(2,2,6,6-tetramethyl-4-piperidinyl)-3(S)-pyridazinecarboxamide;

1-[2(R or S)-[1(S)-(hydroxycarbamoyl)-4-phenylbutyl]undecanoyl]-piperidine;

4-[2(R or S)-[1(S)-(hydroxycarbamoyl)-4-phenylbutyl]undecanoyl]-morpholine;

1-(Benzyloxycarbonyl)-hexahydro-2-[2(R)-[(R or S)-(hydroxycarbamoyl)-4-phenylbutyl]nonanoyl]-N-(α(S)-methylbenzyl)-3(S)-pyridazinecarboxamide;

N-[(2R)-2-[2'-(Hydroxyamino)-2'-(oxo)ethyl]-5-(carboxy)pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2"-(Hydroxyamino)-2"-(oxo)ethyl]-6'-(hydroxy)hexanoyl]amino-3,3-dimethylbutanoic acid N-methylamide;

(2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'-oxobutylamino)hexanoyl]-L-phenylalanine N-methylamide;

2(S)-N-2-[(2'R)-2'-[2"-(Hydroxyamino)-2"-(oxo)ethyl]-6'-(oxo)-6'-(propylamino)hexanoyl]amino-3,3-dimethylbutanoic acid N-methylamide;

N-[(2R)-2-[(1'S)-1'-(Methyl)-2'-(hydroxyamino)-2'-(oxo)ethyl]-6-(phenylmethoxy)hexanoyl]-L-phenylalanine N-methylamide;

N-[(2R)-2-[(1'S)-1'-(Methyl)-2'-(hydroxyamino)-2'-(oxo)ethyl]-6-(oxo)-6-(propylamino)hexanoyl]-L-phenylalanine N-methylamide;

(2S)-N-2[(2'R)-[(1"R)-1"-(1,3-Dihydro-1,3-dioxo-2H-isoindol-2-yl)methyl-2"-(hydroxyamino)-2"-(oxo)ethyl]-6'-(phenylmethoxy)hexanoyl]amino-3,3-dimethylbutanoic acid N-methylamide;

N-[(2R)-2-[2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-2-phenylethylamide;

(2S)-N-2-[(2'R)-2'-[(1"S)-1"-(Methyl)-2"-(hyroxyamino)-2"-(oxo)ethyl]-6'-(oxo)-6'-(propylamino)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-(4'-sulfamoyl)phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)-phenylethylamide;

N-[2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

(2S)-N-2'-[(2'R)-2'-[2"-(Hydroxyamino)-2"-(oxo)ethyl]-6'-[(4-methoxy)phenoxyl]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(1-oxo)butylamino]hexanoyl]amino-3- cyclohexylpropionic acid N-2-(4'-sulfamoyl) phenylethylamide;

(2S)-N-2-[(2'R)-2'-[(1'S)-1"-(Methyl)-2"-(hydroxyamino)—2"-(oxo)ethyl]-6-(phenylmethoxy) hexanoyl]amino-3,3-dimethylbutanoic acid N-methyl amide;

(2S)-N-2-[(2'R)-2'-[(1"S)-1"-(2-Methylpropyl)-2"-(hydroxyamino)-2"-(oxo)ethyl]-6-(phenylmethoxy) hexanoyl]-amino-3,3-dimethylbutanoic acid N-methylamide;

N-[(2R)-2-[2'-(Hydroxyamino)-2'-(oxo)ethyl]-6-(phenoxy)-hexanoyl]-L-phenylalanine N-methylamide;

N-[(2R)-2-[2'-(Hydroxyamino)-2'-(oxo)ethyl]-7-(phenoxy)-heptanoyl]-L-phenylalanine N-methylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)-phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylalanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide;

(2S)-N-2'-[(2'R)-2'-(carboxymethyl)-6'-(3-methylphenoxy) hexanoyl]-amino-3,3-dimethylbutanoic acid N-methylamide;

N-[(2R)-2-[2'-(Hydroxyamino)-2'-(oxo)ethyl]-5-(carboxy) pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2"-(Hydroxyamino)-2"-(oxo)ethyl]-6'-(hydroxy)hexanoyl]amino-3,3-dimethylbutanoic acid N-methylamide;

(2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'-oxobutylamino)hexanoyl]-L-phenylalanine N-methylamide;

2(S)-N-2-[(2'R)-2'-[2"-(Hydroxyamino)-2"-(oxo)ethyl]-6'-(oxo)-6'-(propylamino)hexanoyl]amino-3,3-dimethylbutanoic acid N-methylamide;

N-[(2R)-2-[(1'S)-1'-(Methyl)-2'-(hydroxyamino)-2'-(oxo) ethyl]-6-(phenylmethoxy)hexanoyl]-L-phenylalanine N-methylamide;

N-[(2R)-2-[(1'S)-1'-(Methyl)-2'-(hydroxyamino)-2'-(oxo) ethyl]-6-(oxo)-6-(propylamino)hexanoyl]-L-phenylalanine N-methylamide;

(2S)-N-2[(2'R)-[(1"R)-1"-(1,3-dihydro-1,3-dioxo-2H-isoindol-2-yl)methyl-2"-(hydroxyamino)-2"-(oxo)ethyl]-6'-(phenylmethoxy)hexanoyl]amino-3,3-dimethylbutanoic acid N-methylamide;

N-[(2R)-2-[2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl] amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl] amino-3,3-dimethylbutanoic acid N-2-(4'-sulfamoyl) phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

N-[(2R)-2-[2'-(Hydroxyamino)-2'-(oxo)ethyl]-6'-(phenylmethoxy)hexanoyl]-L-(3,5-dimethyl) phenylalanine N-2-(4'-sulfamoyl)phenylethylamide;

(2S)-N-2'-[(2'R)-2'-[2"-(Hydroxyamino)-2"-(oxo)ethyl]-6'-[(4-methoxy)phenoxy]hexanoyl]amino-3,3-dimethylbutanoic acid N-2-(4'-sulfamoyl) phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl) phenylethylamide;

(2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl) phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-methylamide;

(2S)-N-2-[(2'R)-2'-[(1"S)-1"-(2-Methylpropyl)-2"-(hydroxyamino)-2"-(oxo)ethyl]-6-(phenylmethoxy) hexanoyl]amino-3,3-dimethylbutanoic acid N-methylamide;

N-[(2R)-2-[2-(Hydroxyamino)-2'-(oxo)ethyl]-6-(phenoxy) hexanoyl]-L-phenylalanine N-methylamide;

N-[(2R)-2-[2'-(Hydroxyamino)-2'-(oxo)ethyl]-7-(phenoxy) heptanoyl]-L-phenylalanine N-methylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylelanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide;

(2S)-N-2'-[(2'R)-2'-(Carboxymethyl)-6'-(3-methylphenoxy)hexanoyl]-amino-3,3-dimethylbutanoic acid N-methylamide;

(3R,10S)-5-Methyl-3-(9-oxo-1,8-diazatricyclo[10.6.1.0]nonadeca-12(19),13(18),14,16-tetraen-10-ylcarbamoyl)hexanoic acid;

(3R,10S)-N-Hydroxy-5-methyl-3-(9-oxo-1,8-diazatricyclo[10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo[11.6.1.0]eicosa-13(20),14(19),15,17-tetraen-11-ylcarbamoyl)hexanamide;

(3R,9S)-5-Methyl-3-(8-oxo-1,7-diazatricyclo[9.6.1.0]octadeca-11(18),12(17),13,15-tetraen-9-ylcarbamoyl)hexanoic acid;

(3R,9S)-N-Hydroxy-5-methyl-3-(8-oxo-1,7-diazatricyclo[9.6.1.0]octadeca-11(18),12(17),13,15-tetraen-9-ylcarbamoyl)hexanamide;

(10S)-[4-Methyl-2-(9-oxo-1,8-diazatricyclo[10.6.1.0)nonadeca-12(19),13(18),14,16-tetraen-10-ylcarbamoyl)pentyl]-(quinolin-2-ylthiomethyl)phosphinic acid;

(3R, 10S)-N-Hydroxy-5-methyl-2-methoxycarbonyl-3-(9-oxo-1,8-diazatricyclo[10.6.1.0]nonadeca-12(19),13(18),14,16-tetraen-10-ylcarbamoyl)hexanamide;

N-(4-Methyl-2-carboxymethylpentanoyl)-L-leucine-N'-(4-methoxycarbonylphenyl)carboxamide;

N-(4-Methyl-2-(N"-hydroxycarbamoyl)methylpentanoyl)-L-leucine-N'-(4-methoxycarbonylphenyl)carboxamide;

N-(4-Methyl-2-(N"-hydroxycarbamoyl)methylpentanoyl)-L-leucine-N'-(4-carboxyphenyl)carboxamide;

N-(4-Methyl-2-(N"-hydroxycarbamoyl)methylpentanoyl)-L-tryptophan-N'-(4-carboxyphenyl)carboxamide;

N-(4-Methyl-2-(N"-hydroxycarbamoyl)methylpentanoyl)-L-cyclohexylglycine-N'-(4-methoxycarbonylphenyl)carboxamide;

N-(4-Methyl-2-(N"-hydroxycarbamoyl)methylpentanoyl)-L-t-leucine-N'-(4-methoxycarbonylphenyl)carboxamide;

(3R,10S)-6-Biphenyl-4-yl)-3-(9-oxo-1,8-diazatricyclo[10.6.1.0]onadeca-12(19),13(18),14,16-tetraen-10-ylcarbamoyl)hexanoic acid;

(3R,10S)-3-(9-Oxo-1,8-diazatricyclo[10.6.1.0]nonadeca-12(19),13(18),14,16-tetraen-10-ylcarbamoyl)-5-(thiophen-2-yl)pentanoic acid;

(3R,10S)-3-Cyclopentyl-3-(9-oxo-1,8-diazatricyclo[10.6.1.0]nonadeca-12(19),13(18),14,16-tetraen-10-ylcarbamoyl)propionic acid;

(3R,10S)-4-Cyclopentyl-3-(9-oxo-1,8-diazatricyclo[10.6.1.0]nonadeca-12(19),13(18),14,16-tetraen-10-ylcarbamoyl)butanoic acid;

(3R,10S)-4-Cyclopropyl-3-(9-oxo-1,8-diazatricyclo[10.6.1.0]nonadeca-12(19),13(18),14,16-tetraen-10-ylcarbamoyl)butanoic acid;

(3R,10S)-5-Methyl-3-(9-oxo-1,8-diazatricyclo[10.6.1.0]nonadeca-12(19),13(18),14,16-tetraen-10-ylcarbamoyl)hexanoic acid;

(3R,10S)-N-Hydroxy-5-methyl-3-(9-oxo-1,8-diazatricyclo[10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo[11.6.1.0]eicosa-13(20),14(19),15,17-tetraen-11-ylcarbamoyl)hexanamide;

(3R,9S)-N-5-Methyl-3-(8-oxo-1,7-diazatricyclo[9.6.1.0]octadeca-11(18),12(17),13,15-tetraen-9-ylcarbamoyl)hexanoic acid;

(3R,9S)-N-Hydroxy-5-methyl-3-(8-oxo-1,7-diazatricyclo[9.6.1.0]octadeca-11(18),12(17),13,15-tetraen-9-ylcarbamoyl)hexanamide;

(10S)-2-Mercaptomethyl-4-methyl-N-(9-oxo-1,8-diazatricyclo[10.6.1.0]nonadeca-12(19),13(18),14,16-tetraen-10-ylcarbamoyl)pentanamide;

(10S)-2-Acetylthiomethyl-4-methyl-N-(9-oxo-1,8-diazatricyclo[10.6.1.0]nonadeca-12(19),13(18),14,16-tetraen-10-ylcarbamoyl)pentanamide;

(3R,10S)-2-(Methanesulfonamidomethyl)-5-methyl-3-(9-oxo-1,8-diazatricyclo[10.6.1.0]nonadeca-12(19),13(18),14,16-tetraen-10-ylcarbamoyl)hexanoic acid;

(3R,10S)-2-(3-Ethylureidomethyl)-5-methyl-3-(9-oxo-1,8-diazatricyclo[10.6.1.0]nonadeca-12(19),13(18),14,16-tetraen-10-ylcarbamoyl)hexanoic acid;

(3R,9S)-N-Hydroxy-2-hydroxy-5-methyl-3-(8-oxo-1,7-diazatricyclo[9.6.1.0]octadeca-11(18),12(17),14,16-tetraen-9-ylcarbamoyl)hexanamide or its (2S,3R,9S) stereoisomer;

(3R,10S)-N-Hydroxy-5-methyl-2-methoxycarbonyl-3-(9-oxo-1,8-diazatricyclo[10.6.1.0]nonadeca-12(19),13(18),14,16-tetraen-10-ylcarbamoyl)hexanamide;

(3R,9S)-5-Methyl-3-(8-oxo-4-oxa-1,7-diazatricyclo[9.6.1.0]octadeca-11(18),12,14,16-tetraen-9-ylcarbamoyl)hexanoic acid;

(3R,9S)-3-Cyclobutylmethyl-N-(8-oxo-4-oxa-1,7-diazatricyclo[9.6.1.0]octadeca-11(18),12,14,16-tetraen-9-ylcarbamoyl)succinamic acid;

(3R,9S)-3-(8-oxo-4-oxa-1,7-diazatricyclo[9.6.1.0]octadeca-11(18),12,14,16-tetraen-9-ylcarbamoyl)-5-phenoxy-pentanoic acid;

(3R,9S)-5-(4-Chlorophenoxy)-3-(8-oxo-4-oxa-1,7-diazatricyclo[9.6.1.0]octadeca-11(8),12,14,16-tetraen-9-ylcarbamoyl)pentanoic acid;

(3R,9S)-5-(4-Chlorophenoxy)-3-(8-oxo-4-oxa-1,7-diazatricyclo[9.6.1.0]octadeca-11(18),12,14,16-tetraen-9-ylcarbamoyl)pentanoic acid ethyl ester;

(3R,9S)-3-(8-oxo-1,7-diazatricyclo[9.6.1.0]octadeca-11(18),12,14,16-tetraen-9-ylcarbamoyl)pentanoic acid ethyl ester;

(3R,9S)-6-(4-Hydroxy-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-6-pyridin-4-yl-hexanoic acid;

(3R,9S)-6-[4-(3-Hydroxy-propoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0)octadeca-11(18),12,14,16-tetraen-9-ylcarbamoyl)-5-(4-phenoxy-phenyl)pentanoic acid;

(3R,9S)-6-[4-(2-Hydroxy-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-6-[4-(2-pyrrolidin-1-yl-ethoxyphenyl]hexanoic acid;

(3R,9S)-6-(4-Methoxy-phenyl)-3-(8-oxo-4-oxa-1,7-diazatricyclo[9.6.1.0]-octadeca-11(18),12,14,16-tetraen-9-ylcarbamoyl)hexanoic acid;

(3R,9S)-6-[4-(2-Methoxy-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-5-phenyl-pentanoic acid;

(3R,9S)-3-(8-Oxo-4-oxa-1,7-diazatricyclo[9.6.1.0]octadeca-11(18),12,14,16-tetraen-9-ylcarbamoyl)-6-phenyl-hexanoic acid;

(3R,9S)-6-(3-Hydroxy-phenyl)-3-(8-oxo-4-oxa-1,7-diazatricyclo[9.6.1.0]-octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-6-[4-(3-piperidin-1-yl-propoxy)phenyl]hexanoic acid;

(3R,9S)-6-[4-(3-Dimethylamino-propoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-6-[4-(2-Dimethylamino-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-6-(4-Cyano-phenyl)-3-(8-oxo-4-oxa-1,7-diazatricyclo[9.6.1.0]-octadeca-11(18),12,14,16-tetraen-9-ylcarbamoyl)hexanoic acid;

(3R,9S)-6-Naphthalen-2-yl-3-(8-oxo-4-oxa-1,7-diazatricyclo[9.6.1.0]-octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-6-(4-pyrrol-1-yl)hexanoic acid;

(3R,9S)-6-(4-Hydroxy-3-methyl-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-6-(4-Benzyloxy-phenyl)-3-(8-oxo-4-oxa-1,7-diazatricyclo[9.6.1.0]octadeca-11 (18),12,14,16-tetraen-9-ylcarbamoyl)hexanoic acid;

(3R,9S)-6-[4-(4-Aminobutoxy-phenyl)]-3-(8-oxo-4-oxa-1,7-diazatricyclo[9.6.1.0]octadeca-11(18),12,14,16-tetraen-9-ylcarbamoyl)hexanoic acid;

(3R,9S)-5-(4-Methoxy-phenyl)-3-(8-oxo-4-oxa-1,7-diazatricyclo[9.6.1.0]-octadeca-11(18),12,14,16-tetraen-9-ylcarbamoyl)pentanoic acid;

(3R,9S)-6-(4-Amino-phenyl)-3-(8-oxo-4-oxa-1,7-diazatricyclo[9.6.1.0]-octadeca-11(18),12,14,16-tetraen-9-ylcarbamoyl)hexanoic acid;

(3R,9S)-3-(8-Oxo-4-oxa-1,7-diazatricyclo[9.6.1.0]octadeca-11(18),12,14,16-tetraen-9-ylcarbamoyl)-6-[4-(pyridin-4-ylmethoxy)phenyl]hexanoic acid;

(3R,9S)-6-(4-Acetylamino-phenyl)-3-(8-oxo-4-oxa-1,7-diazatricyclo[9.6.1.0]octadeca-11(18),12,14,16-tetraen-9-ylcarbamoyl)hexanoic acid;

$N^\alpha$-[[3-(N-Hydroxycarbamoyl)-4-methylthio-2-propoxymethyl]butylyl]-N,O-dimethyltyrosine amide;

$N^\alpha$-[[3-(N-Hydroxycarbamoyl)-4-isopropylthio-2-propoxymethyl]butylyl]-N,O-dimethyltyrosine amide;

$N^\alpha$-[[3-(N-Hydroxycarbamoyl)-2-propylthio]butylyl]-N,O-dimethyltyrosine amide;

N-[N-(1-Phosphono-3-phenylpropyl)-(S)-leucyl]-(S)-phenylalanine-N-methylamide;

N-[N-(1-Phosphono-3-(4-bromo-1,8-naphthalene-dicarboximido)propyl)-(S)-leucyl]-(S)-phenylalanine methylamide;

N-[N-(1-Phosphono-3-(benzyloxycarbonylamino)propyl)-(S)-leucyl]-(S)-phenylalanine methylamide;

N-[N-(1-Phosphono-3-(2-hydroxyphenyl)propyl)-(S)-leucyl]-(S)-phenylalanine methylamide;

N-[N-(1-Phosphono-3-(methylmercapto)propyl)-(S)-leucyl]-(S)-phenylalanine-N-methylamide;

N-[N-(1-Phosphono-3-(methylsulphinyl)propyl)-(S)-leucyl]-(S)-phenylalanine-N-methylamide;

N-[N-(1-Phosphono-3-(methylsulphonyl)propyl)-(S)-leucyl]-(S)-phenylalanine-N-methylamide;

N-[N-(1-Phosphono-3-(1,8-naphthalenedicarboximido)propyl)-(S)-leucyl]-(S)-tryptophan-N-methylamide;

N-[N-(1-Phosphono-3-(1,8-naphthalenedicarboximido)propyl)-(S)-leucyl]-(S)-lysine-N-methylamide;

N-[N-(1-Phosphono-3-(1,8-naphthalenedicarboximido)propyl)-(S)-leucyl]-(–)-aminoazacyclotridecan-2-one;

N-[N-(1-Phosphono-3-(1,8-naphthaienedicarboximido)propyl)-(S)-leucyl]-(S)-lysine-N-(aminoethyl)amide;

N-[N-(1-Phosphono-3-(1,8-naphthalenedicarboximido)propyl)-(S)-leucyl]-(S)-lysine-N-(ethylpyrrolidine)amide;

N-[N-(1-Phosphono-3-(1,8-naphthalenedicarboximido)propyl)-(S)-leucyl]-(S)-lysine-N-(ethyl-N-methylpiperazine)amide;

N-[N-(1-Phosphono-3-[8-(7,9-dioxo-8-azaspiro[4,5]decyl)]propyl)-(S)-leucyl]-(S)-phenylalanine-N-methylamide; and N-[N-(1-Phosphono-3-[8-(7,9-dioxo-8-azaspiro[4,5]decyl)]propyl)-(S)-leucyl]-(S)-lysine-N-methylamide.

As noted above, numerous inhibitors of matrix metalloproteinases are known. A large number of inhibitors are characterized as hydroxamic acid-based and/or carboxylic acid-based compounds. Typical of such compounds are those described in the following references, all of which are incorporated herein by reference, since all of the disclosed compounds can be used in the method of this invention.

U.S. Pat. No. 4,599,361(Searle)
EP-A-2321081 (ICI)
EP-A-0236872(Roche)
EP-A-0274453 (Bellon)
WO 90/05716(British Biotechnology)
WO 90/05719(British Biotechnology)
WO 91/02716(British Biotechnology)
WO 92/09563(Glycomed)
U.S. Pat. No. 5,183,900(Glycomed)
U.S. Pat. No. 5,270,326 (Glycomed)
WO 92/17460 (Smith-Kline Beecham)
EP-A-0489577 (Celltech)
EP-A-0489579 (Celltech)
EP-A-0497192 (Roche)
U.S. Pat. No. 5,256,657 (Sterling Winthrop)
WO 92/13831 (British Biotechnology)
WO 92/22523 (Research Corporation Technologies)
WO 93/09090 (Yamanouchi)
WO 93/09097 (Sankyo)
WO 93/20047 (British Biotechnology)
WO 93/24449 (Celltech)
WO 93/24475 (Celltech)
EP-A-0574758 (Roche)
WO 94/02447 (British Biotechnology)
WO 94/02446 (British Biotechnology)
WO 97/27174 (Shionogi)

An especially preferred group of compounds to be employed in the present method are those described in WO 95/35275 and WO 95/35276, both of which are incorporated herein by reference. Typical compounds from within these groups to be employed include:

N-Hydroxy-2-[[(2-(4-methoxy-phenoxy)-ethyl-(toluene-4-sulfonyl)-amino]-acetamide;

N-Hydroxy-2-[(4-phenoxy-ethyl)-toluene-4-sulfonyl) amino]-acetamide;

N-Hydroxy-2-[(4-methoxy-benzenesulfonyl)-nonyl-amino]-acetamide;

2-[-Decyl-(toluene-4-sulfonyl)-amino]-N-hydroxy-acetamide;

2-Benzyl-(octane-1-sulfonyl)-amino]-N-hydroxy-acetamide;

N-Hydroxy-2-[(2-methoxy-benzyl)-(octane-1-sulfonyl)-amino]-acetamide;

2-[(2-Ethoxy-benzyl)-(octane-1-sulfonyl)-amino]-N-hydroxy-acetamide;

N-Hydroxy-2-[(naphthalen-2-yl-methyl)-(octane-1-sulfonyl)-amino]-acetamide;

2-[(4-Chloro-benzyl)-(octane-1-sulfonyl)-amino]-N-hydroxy-acetamide, and salts, solvates, or hydrates thereof.

Another class of matrix metalloproteinase inhibitors are aryl sulfonamides of the formula

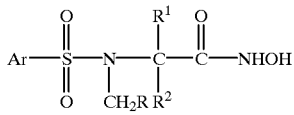

where Ar is carbocyclic or heterocyclic aryl, and R, $R^1$, and $R^2$ include hydrogen, alkyl, aryl, heteroaryl, amino, substituted and disubstituted amino. These compounds are disclosed in European Patent Number 0606046, incorporated herein by reference. Specific compounds to be employed in the present method include:

N-Hydroxy-2-[[4-methoxybenzenesulfonyl](isobutyl) amino]acetamide;

N-Hydroxy-2-[[4-methoxybenzenesulfonyl] (cyclohexylmethyl)amino]acetamide;

N-Hydroxy-2-[[4-methoxybenzenesulfonyl](cyclohexyl) amino]acetamide;

N-Hydroxy-2-[[4-methoxybenzenesulfonyl](phenethyl) amino]acetamide;

N-Hydroxy-2-[[4-methoxybenzenesulfonyl](3-methylbutyl) amino]acetamide;

N-Hydroxy-2-[[4-methoxybenzenesulfonyl](sec-butyl) amino]acetamide;

N-Hydroxy-2-[[4-methoxybenzenesulfonyl](tert-butyl) amino]acetamide

N-Hydroxy-2-[[4-methoxybenzenesulfonyl](4-fluorobenzyl)amino]acetamide

N-Hydroxy-2-[[4-methoxybenzenesulfonyl](4-chlorobenzyl)amino]acetamide

N-Hydroxy-2-[[4-methoxybenzenesulfonyl](isopropyl)-amino]acetamide

N-Hydroxy-2-[[4-methoxybenzenesulfonyl](4-methylbenzyl)amino]acetamide

4-N-Hydroxy-carbamoyl]-4-[[4-methoxybenzene-sulfonyl (benzyl)-amino]-1-[dimethylaminoacetyl]-piperidine hydrochloride 4-N-Hydroxy-carbamoyl]-4-[[4-methoxybenzene-sulfonyl (benzyl)-amino]-1-[3-picolyl]-piperidine dihydrochloride 4-N-Hydroxy-carbamoyl]-4-[[4-methoxybenzene-sulfonyl (benzyl)-amino]-1-[carbomethoxymethyl]-piperidine hydrochloride 4-N-Hydroxy-carbamoyl]-4-[[4-methoxybenzene-sulfonyl (benzyl)-amino]-1-piperidine trifluoroacetate;

4-N-Hydroxy-carbamoyl]-4-[[4-methoxybenzene-sulfonyl (benzyl)-amino]-1-[t-butoxycarbonyl]-piperidine;

4-N-Hydroxycarbamoyl]-4-[[4-methoxybenzene-sulfonyl (benzyl)-amino]-1-[methylsulfonyl]-piperidine;

N-Hydroxycarbamoyl]-4-[[4-methoxybenzene-sulfonyl (benzyl)-amino]-1-[4-picoly]-piperidine hydrochloride;

N-Hydroxycarbamoyl]-4-[[4-methoxybenzene-sulfonyl (benzyl)amino]-1-[morpholinocarbonyl]-piperidine hydrochloride; and N-(t-Butyloxy)-2-[[4-methoxybenzenesulfonyl (benzyl) amino]-2-[2-(4-morpholino)ethyl]acetamide.

N-Hydroxy-2-[[4-methoxybenzenesulfonyl](isobutyl)-amino-2-(2-(4-morpholino)ethyl]acetamide;

N-Hydroxy-2-[[4-methoxybenzenesulfonyl](2-picoly)-amino-2-(2-(4-morpholino)ethyl]acetamide dihydrochloride;

N-Hydroxy-2-[[4-methoxybenzenesulfonyl](3-picolyl) amino]-2-[2-(4-morpholino)ethyl]acetamide dihydrochloride;

N-Hydroxy-2-[[4-methoxybenzenesulfonyl](2-methyl-thiazol-4-ylmethyl)amino]-2-[2-(4-morpholino) ethyl] acetamide dihydrochloride;

N-Hydroxy-2-[[4-methoxybenzenesulfonyl]benzyl)amino]-2-[2-(4-thiomorpholino]ethyl]acetamide;

N-Hydroxy-2-[[4-methoxybenzenesulfonyl](benzyl) amino]-2-[2-(4-methylthiazol-4-ylmethyl]acetamide;

N-Hydroxy-2-[[4-methoxybenzenesulfonyl (benzyl) amino]-2-[(6-chloropiperonyl]acetamide;

N-Hydroxy-2-[[4-methoxybenzenesulfonyl(benzyl)amino]-2-[(1-pyrazolyl)methyl]acetamide;

N-Hydroxy-2-[[4-methoxybenzenesulfonyl (3-picolyl) amino]-2-[3-picolyl]acetamide;

N-Hydroxy-2-[[4-methoxybenzenesulfonyl(benzyl)-amino]-2-[(1-methyl-4-imidazolyl)methyl]acetamide hydrochloride;

N-Hydroxy-2-[[4-methoxybenzenesulfonyl(isobutyl) amino]-2-[(1-methyl-4-imidazolyl)methyl]acetamide hydrochloride;

N-Hydroxy-2-[[4-methoxybenzenesulfonyl](3-picolyl) amino]-2-[(1-methyl-4-imidazolyl) methyl]acetamide hydrochloride;

N-Hydroxy-2-[[4-methoxybenzenesulfonyl(2-picolyl) amino]-2-[(1-methyl-4-imidazolyl)methyl]-acetamide hydrochloride; and N-Hydroxy-2-[[4-methoxybenzenesulfonyl](2-methylthiazol-4-ylmethyl)amino-2-[(1-methyl-4-imidazolyl)methyl]acetamide hydrochloride.

Another group of small peptide matrix metalloproteinase inhibitors are described in U.S. Pat. Nos. 5,270,326, 5,530, 161, 5,525,629, and 5,304,604 (incorporated herein by reference). The compounds are hydroxamic acids defined by the formula.

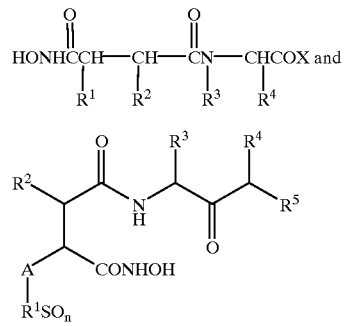

where $R^1$, $R^2$, $R^3$, and $R^4$ can be hydrogen or alkyl and X is $OR^5$ or $NHR^5$ where $R^5$ includes hydrogen, alkyl and aryl, A includes alkyl, and n is 0 to 2. Typical compounds to be employed in the instant method include the following:

N-[2-Isobutyl-3-(N'-hydroxycarbonylamido)-propanoyl]-D-tryptophan methylamide;

N-[2-Isobutyl-3-(N'-hydroxycarbonylamido)-propanoyl]-N-methyl-L-tryptophan methylamide;

N-[2-Isobutyl-3-(N-hydroxycarbonylamido)-propanoyl]-L-3-(2-naphthyl)-alanine methylamide;

N-[2-Isobutyl-3-(N'-hydroxycarbonylamido)-propanoyl]-L-tryptophan 2-hydroxyethylamide;

N-[2-Isobutyl-3-(N'-hydroxycarbonylamido)-propanoyl]-L-tryptophan amylamide;

N-[2-Isobutyl-3-(N'-hydroxycarbonylamido)-propanoyl]-L-tryptophan piperidinamide;

N-[2-Isobutyl-3-(N'-hydroxycarbonylamido)-propanoyl-L-tryptophan dodecylamide;

N-[2-Isobutyl-3-(N'-hydroxycarbonylamido)-propanoyl]-L-tryptophan(S)-methylbenzylamide;

N-[L-2-Isobutyl-3-(N'-hydroxycarbonylamido)-propanoyl]-L-tryptophan(6-phenylmethoxycarbonyl-amino-hexyl-1) amide;

2S-Hydroxy-3R-[1S-(3-methoxy-2,2-dimethyl-propylcarbamoyl)-2,2-dimethyl-propylcarbamoyl]-5-methyl-hexanohydroxamic acid;

2S-Hydroxy-3R-[1S-(methylcarbamoyl)-2,2-dimethyl-propylcarbamoyl]-6-(4-chloro)phenyl-hexanohydroxamic acid;

2S-Hydroxy-3R-[1S-(methylcarbamoyl)-2,2-dimethyl-propyl-carbamoyl]octanohydroxamic acid;

2S-Hydroxy-3R-[1S-(pyridin-2-ylmethylcarbamoyl)-2,2-dimethyl-propyl-carbamoyl]-5-methyl-hexanohydroxamic acid;

2S-Hydroxy-3R-[1S-(pyridin-3-ylmethylcarbamoyl)-2,2-dimethyl-propyl-carbamoyl]-5-methyl-hexanohydroxamic acid;

2S-Hydroxy-3R-[1S-(pyridin-4-ylmethylcarbamoyl)-2,2-dimethyl-propyl-carbamoyl]-5-methyl-hexanohydroxamic acid;

2S-Hydroxy-3R-[1S-(methylcarbamoyl)-2,2-dimethyl-propylcarbamoyl]-4-methoxy-butanohydroxamic acid;

2S-Hydroxy-3R-[1S-(methylcarbamoyl)-2,2-dimethyl-propylcarbamoyl]-4-benzyloxy-butanohydroxamic acid;

2S-Hydroxy-3R-[1S-(methylcarbamoyl)-2,2-dimethyl-propylcarbamoyl]-4-benzylthio-butanohydroxamic acid;

2S-Hydroxy-3R-[1S-(methylcarbamoyl)-2,2-dimethyl-buten-3-yl carbamoyl]-5-methyl-hexanohydroxamic acid;

2S-Hydroxy-3R-[1S -(tert-butylcarbamoyl)-2,2-dimethyl-propyl-carbamoyl]-5-methyl-hexanohydroxamic acid;

2S-Hydroxy-3R-[1S-(N,N-dimethyl-carbamoyl)-2,2-dimethyl-propyl-carbamoyl]-5-methyl-hexanohydroxamic acid;

2S-Hydroxy-3R-[1S-(3-hydroxy-2,2-dimethyl-propylcarbamoyl)-2,2-dimethyl-propylcarbanoyl]-5-methyl-hexanohydroxamic acid;

2S-Hydroxy-3R-[1S-(methylcarbamoyl)-2,2-dimethyl-propylcarbamoyl]-6-phenyl-hexanohydroxamic acid;

2S-Hydroxy-3R-[1S-(methylcarbamoyl)-2,2-dimethyl-butylcarbamoyl]-5-methyl-hexanohydroxamic acid;

[4-(N-Hydroxyamino)-2R-isobutylsuccinyl]-L-phenylalanine-N-(2-hydroxyethyl)-amide;

[4-(N-Hydroxyamino)-2R-isobutylsuccinyl]-L-phenylalaninyl-proline;

[4-(N-Hydroxyamino)-2R-isobutylsuccinyl]-L-phenylalanine-N-(2-hydroxyethyl)-N-methylamide;

[4-(N-Hydroxyamino)-2R-isobutylsuccinyl]-L-phenylalaninyl-D-prolinol;

[4-(N-Hydroxyamino)-2R-isobutylsuccinyl]-L-phenylalaninyl-L-prolinol;

[4-(N-Hydroxyamino)-2R-isobutylsuccinyl]-L-phenylalanine-N-(5-N-methyl-pentylcarboxamide) amide;

[4-(N-Hydroxyamino)-2R-isobutylsuccinyl]-L-phenylalanine-N-(2-ethylthioethyl)amide;

[4-(N-Hydroxyamino)-2R-isobutylsuccinyl]-L-phenylalanine-N-(2-methoxyethyl)amide;

[4-(N-Hydroxyamino)-2R-isobutylsuccinyl]-L-phenylalanine-N-(2-N-acetylethyl)amide;

[4-(N-Hydroxyamino)-2R-isobutylsuccinyl]-L-phenylalanine-N-(3-(2-pyrrolidone)propyl)amide;

[4-(N-Hydroxyamino)-2R-isobutylsuccinyl]-L-phenylalanine-N-(3-(2-pyrrolidone)propyl)amide sodium salt;

[4-(N-Hydroxyamino)-2R-isobutylsuccinyl]-L-phenylalanine-N-(2-acetoxyethyl)amide;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-methyl-N-(2)-hydroxyethyl)amide;

[4-(N-Hydroxyamino)-2R-isobutyl-3S-methylsuccinyl]-L-phenylalanine-N-(2-hydroxyethyl)amide;

[4-(N-Hydroxyamino)-2R-isobutyl-3S-methylsuccinyl]-L-phenylalaninyl-D-prolinol;

[4-(N-Hydroxyamino)-2R-isobutyl-3S-methylsuccinyl]-L-phenylalanine-N-(3-(2-pyrrolidone)propyl)amide sodium salt;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-(3-(2-pyrrolidone)propyl)amide or a salt thereof;

$N^{2-}$[4-(N-Hydroxyamino)-3S-(4-hydroxyphenylthiomethyl)-2R-isobutylsuccinyl]-$N^{6-}$tert-butyloxycarbonyl-L-lysine-$N^{1-}$methylamide;

$N^{2-}$[4-(N-Hydroxyamino)-3S-(4-hydroxyphenylthiomethyl)-2R-isobutylsuccinyl]-$N^{6-}$tert-butyloxycarbonyl-$N^{6-}$(4-hydroxyphenylthiomethyl)-L-lysine-$N^{1}$-methylamide;

$N^{2-}$[4-(N-Hydroxyamino)-3S-(2-thienylthiomethyl)-2R-isobutylsuccinyl]-$N^{6-}$tert-butyloxycarbonyl-L-lysine-$N^{1-}$methylamide;

$N^{2-}$[4-(N-Hydroxyamino)-3S-(4-hydroxyphenylthiomethyl)-2R-isobutylsuccinyl]-O-tert-butyl-L-threonine-$N^{1-}$methylamide;

$N^{2-}$[4-(N-Hydroxyamino)-3S-(4-hydroxyphenylthiomethyl)-2R-isobutylsuccinyl]-L-glutamine-$N^{1}$,$N^{5-}$dimethylamide;

$N^{2-}$[4-(N-Hydroxyamino)-3S-(4-hydroxyphenylsulphonylmethyl)-2R-isobutylsuccinyl]-$N^{6-}$acetyl-L-lysine-$N^{1-}$methylamide;

3R-(3-Methoxycarbonyl-1S-methylcarbamoyl-propylcarbamoyl)-5-methyl-2S-2-propenyl-hexanohydroxamic acid;

3R-(1S-Methylcarbamoyl-2-thien-2-yl-ethylcarbamoyl)-5-methyl-2S-2-propenyl-hexanohydroxamic acid;

3R-(3-Methyl-1S-methylcarbamoyl-butylcarbamoyl)-5-methyl-2S-2-propenyl-hexanohydroxamic acid;

2S-[1S-Methylcarbamoyl-2-oxadiazol-5-yl-ethylcarbamoyl)-5-methyl-2S-2-propenyl-hexanohydroxamic acid;

[4-(N-Hydroxyamino)-2R-isobutylsuccinyl]-L-(4-oxymethylcarboxylic acid)phenylalanine-N-methylamide;

[4-(N-Hydroxyamino)-2R-isobutylsuccinyl]-L-(4-oxymethylcarboxy-N-methylamide)phenylalanine-N-methylamide;

[4-(N-Hydroxyamino)-2R-isobutylsuccinyl]-L-(4-oxymethylcarboxy-beta-alanine)phenylalanine-N-methylamide;

[4-(N-Hydroxyamino)-2R-isobutylsuccinyl]-L-(4-oxymethylcarboxyglycine)phenylalanine-N-methylamide;

[4-(N-Hydroxyamino)-2R-isobutylsuccinyl]-L-(4-oxymethylcarboxy-N-benzylamide)phenylalanine-N-methylamide;

[4-(N-Hydroxyamino)-2R-isobutylsuccinyl]-L-(4-cyano)phenylalanine-N-methylamide;

[4-(N-Hydroxyamino)-2R-isobutylsuccinyl]-L-(4-acetamido)phenylalanine-N-methylamide;

[4-(N-Hydroxyamino)-2R-isobutylsuccinyl]-L-(4-oxymethylcarboxamide)-henylalanine-N-methylamide;

[4-(N-Hydroxyamino)-2R-isobutyl-3S-(2-thienylthiomethylsuccinyl]-L-(4-N-acetylamino)-henylalanine-N-methylamide;

[4-(N-Hydroxyamino)-2R-isobutyl-3S-(2-thienylthiomethylsuccinyl]-L-(4-N-methylsuccinylamide)phenylalanine-N-methylamide;

[4-(N-Hydroxyamino)-2R-isobutyl-3S-(4-aminophenylthiomethyl)-succinyl]-L-(4-N-(methylsuccinylamide)phenylalanine-N-methylamide;

[4-(N-Hydroxyamino)-2R-isobutyl-3S-(4-aminophenylthiomethylsuccinyl]-L-(4-N-(4-(4-oxobutanoic acid)aminophenylalanine-N-methylamide;

[4-(N-Hydroxyamino)-2R-isobutyl-3S-(4-hydroxyphenylthiomethyl)-succinyl]-L-(4-N-methylsuccinylamido)phenylalanine-N-methylamide;

[4-(N-Hydroxyamino)-2R-isobutyl-3S-(4-hydroxyphenylthiomethyl)-succinyl]-L-(4-N-(4-(4-oxobutanoic acid)aminophenylalanine-N-methylamide;

[4-(N-Hydroxyamino)-2R-isobutyl-3S-(2-thienylthiomethyl)-succinyl]-L-(4-oxymethylcarboxymethyl)phenylalanine-N-methylamide;

[4-(N-Hydroxyamino)-2R-isobutyl-3S-(2-thienylthiomethyl)-succinyl]-L-(4-N-(oxymethylcarboxylic acid)phenylalanine-N-methylamide;

[4-(N-Hydroxyamino)-2R-isobutyl-3S-(2-thienylthiomethyl)-succinyl]-L-4-oxymethylcarboxyglycyl methyl ester)-phenylalanine-N-methylamide;

[4-(N-Hydroxyamino)-2R-isobutyl-3S-(2-thienylthiomethyl)-succinyl]-L-4-oxymethylcarboxyglycine)phenylalanine-N-methylamide;

[4-(N-Hydroxyamino)-2R-isobutyl-3S-methyl-succinyl]-L-4-(oxymethylcarboxyglycyl methyl ester)-phenylalanine-N-methylamide;

[4-(N-Hydroxyamino)-2R-isobutyl-3S-methyl)-succinyl]-L-4-(oxymethylcarboxyglycine)-phenylalanine-N-methylamide;

[4-(N-Hydroxyamino)-2R-isobutylsuccinyl]-L-4-oxymethylnitrile)-phenylalanine-N-methylamide;

[4-(N-Hydroxyamino)-2R-isobutylsuccinyl]-L-3-(1-(2-methyloxycarbonyl)-ethyl)-4-methoxyphenylalanine-N-methylamide;

[4-(N-Hydroxyamino)-2R-isobutylsuccinyl]-L-3-(hydroxymethyl)-4-methoxyphenylalanine-N-methylamide;

[4-(N-Hydroxyamino)-2R-isobutylsuccinyl]-L-3-methyl-4-methoxyphenylalanine-N-methylamide;

2-[Benzyl-(octane-1-sulfonyl)-amino]-N-hydroxy-acetamide;

N-Hydroxy-2-[(2-methoxy-benzyl)-(octane-1-sulfonyl)-amino]-acetamide;

2-[(2-Ethoxy-benzyl)-(octane-1-sulfonyl)-amino]-N-hydroxy-acetamide;

N-Hydroxy-2-[(naphthalen-2-yl-methyl)-(octane-1-sulfonyl)-amino]-acetamide;

2-[(4-Chloro-benzyl)-(octane-1-sulfonyl)-amino]-N-hydroxy-acetamide;

$N^{2}$-[3S-Hydroxy-4-(N-hydroxyamino)-2R-isobutylsuccinyl]-L-leucine-$N^{1}$-methylamide;

$N^{2}$-[3S-Hydroxy-4-(N-hydroxyamino)-2R-isobutylsuccinyl)]-5-methyl-L-glutamic acid-$N^{1}$-methylamide;

$N^{2}$-[3S-Hydroxy-4-(N-hydroxyamino)-2R-isobutylsuccinyl)]-L-phenylalanine-$N^{1}$-methylamide;

[4-(N-Hydroxyamino)-2R-isobutyl-3S-(thienylthiomethyl)succinyl]-L-phenylalanine-N-methylamide;

[4-(N-Hydroxyamino)-2R-isobutyl-3S-phenylthiomethyl)succinyl]-L-phenylalanine-N-methylamide;

2S-(4-Methoxyphenylsulfanylmethyl)-3R-(2-phenyl-1S-methylcarbamoyl-ethylcarbamoyl)-5-methyl-hexanohydroxamic acid;

2S-(3-Chlorophenylsulfanylmethyl)-3R-(2-phenyl-1S-methylcarbamoyl-ethylcarbamoyl)-5-methyl-hexanohydroxamic acid;

2S-(Phenylsulfanylmethyl)-3R-(2-phenyl-1S-(pyrid-3-ylmethylcarbamoyl)-ethylcarbamoyl)-5-methyl-hexanohydroxamic acid;

2S-(3-Methylphenylsulfanylmethyl)-3R-(2-phenyl-1S-methylcarbamoyl-ethylcarbamoyl)-5-methyl-hexanohydroxamic acid;

2S-(Thien-2-ylsulfanylmethyl)-3R-(2-(4-carboxymethoxyphenyl)-1S-methylcarbamoyl-ethylcarbamoyl)-5-methyl-hexanohydroxamic acid;

N-Benzyloxycarbonyl-α-phosphonoglycyl-L-alanine furfurylamide;

[4-(N-Hydroxyamino)-2R-isobutyl-3S-(phenylthiomethyl)succinyl]-L-phenylalanine-N-methylamide;

[4-(N-Hydroxyamino)-2R-isobutyl-3S-(4-methoxyphenylthiomethyl)-succinyl]-L-phenylalanine-N-methylamide;

[4-(N-Hydroxyamino)-2R-isobutyl-3S-(4-hydroxyphenylthiomethyl)-succinyl]-L-phenylalanine-N-methylamide;

[4-(N-Hydroxyamino)-2R-isobutyl-3S-(2,4-dimethylphenylthiomethyl)-succinyl]-L-phenylalanine-N-methylamide;

[4-(N-Hydroxyamino)-2R-isobutyl-3S-(3-bromophenylthiomethyl)-succinyl]-L-phenylalanine-N-methylamide;

[4-(N-Hydroxyamino)-2R-isobutyl-3S-(3-chlorophenylthiomethyl)-succinyl]-L-phenylalanine-N-methylamide;

[4-(N-Hydroxyamino)-2R-isobutyl-3S-(3-methylphenylthiomethyl)-succinyl]-L-phenylalanine-N-methylamide;

[4-(N-Hydroxyamino)-2R-isobutyl-3S-(4-(N-acetyl)-amino-phenylthiomethyl)succinyl]-L-phenylalanine-N-methylamide;

[4-(N-Hydroxyamino)-2R-isobutyl-3S-phenylsulphinylmethylsuccinyl]-L-phenylalanine-N-methylamide;

3R-(3-Methoxycarbonyl-1S-methylcarbamoyl-propylcarbamoyl)-5-methyl-2S-phenylsulfanylmethyl-hexanohydroxamic acid;

3R-(3-Methoxycarbonyl-1S-methylcarbamoyl-propylcarbamoyl)-5-methyl-2S-(thien-2-ylsulfanylmethyl)-hexanohydroxamic acid;

2S-(4-Methoxy-phenylsulfanylmethyl)-3R-(3-methoxycarbonyl-1S-methylcarbamoyl-propylcarbamoyl)-5-methyl-hexanohydroxamic acid;

2S-(4-Amino-phenylsulfanylmethyl)-3R-(3-methoxycarbonyl-1S-methylcarbamoyl-propylcarbamoyl)-5-methyl-hexanohydroxamic acid;

2S-(Ethylsulfanylmethyl)-3R-(3-methoxycarbonyl-1S-methylcarbamoyl-propylcarbamoyl)-5-methyl-hexanohydroxamic acid;

2S-(Acetylsulfanylmethyl)-3R-(3-methoxycarbonyl-1S-methylcarbamoyl-propylcarbamoyl)-5-methyl-hexanohydroxamic acid;

2S-(Benzylsulfanylmethyl)-3R-(3-methoxycarbonyl-1S-methylcarbamoyl-propylcarbamoyl)-5-methyl-hexanohydroxamic acid;

2S-(tert-Butylsulfanylmethyl)-3R-(3-methoxycarbonyl-1S-methylcarbamoyl-propylcarbamoyl)-5-methyl-hexanohydroxamic acid;

2S-Thiomethyl-3R-(3-methoxycarbonyl-1S-methylcarbamoyl-propylcarbamoyl)-5-methyl-hexanohydroxamic acid;

2S-(4-Hydroxy-phenylsulfanylmethyl)-3R-(2-tert-butoxycarbonyl-1S-methylcarbamoyl-ethylcarbamoyl)-5-methyl-hexanohydroxamic acid;

2S-(4-Hydroxy-phenylsulphinylmethyl)-3R-(3-methoxycarbonyl-1S-methylcarbamoyl-propylcarbamoyl)-5-methyl-hexanohydroxamic acid;

2S-(4-Hydroxy-phenylsulphonylmethyl)-3R-(3-methoxycarbonyl-1S-methylcarbamoyl-propylcarbamoyl)-5-methyl-hexanohydroxamic acid;

[4-(N-Hydroxyamino)-2R-isobutylsuccinyl]-L-phenylalanine-N-[1-(2-aminoethyl)-pyrrolidine]amide;

[4-(N-Hydroxyamino)-2R-isobutylsuccinyl]-L-phenylalanine-N-[1-(3-aminopropyl)-2(RS)-methylpiperidine]amide;

[4-(N-Hydroxyamino)-2R-isobutylsuccinyl]-L-phenylalanine-N-[2-(2-aminoethyl)-1-methylpyrrole]amide;

[4-(N-Hydroxyamino)-2R-isobutylsuccinyl]-L-phenylalanine-N-(3-aminomethylpyridine)amide;

[4-(N-Hydroxyamino)-2R-isobutylsuccinyl]-L-phenylalanine-N-(2-aminomethylpyridine)amide;

[4-(N-Hydroxyamino)-2(RS)-isobutylsuccinyl]-L-phenylalanine-N-(4-aminomethylpyridine)amide;

[4-(N-Hydroxyamino)-2(RS)-isobutylsuccinyl]-L-phenylalanine-N-(1-(3-aminopropyl)-imidazole)amide;

[4-(N-Hydroxyamino)-2(RS)-isobutylsuccinyl]-L-phenylalanine-N-(2-aminomethylbenzimdazole)amide;

[4-(N-Hydroxyamino)-2R-isobutyl-3S-methylsuccinyl]-L-phenylalanine-N-[4-(2-aminoethyl)-morpholino]amide;

[4-(N-Hydroxyamino)-2R-isobutylsuccinyl]-L-phenylalanine-N-[4-(2-aminoethyl)-morpholine]amide;

[4-(N-Hydroxyamino)-2(R,S)-isobutylsuccinyl]-L-phenylalanine-N-[2-(2-aminoethyl)-pyridine]amide;

[4-(N-Hydroxyamino)-2(R,S)-isobutylsuccinyl]-L-phenylalanine-N-[4-(2-aminopropyl)-morpholine]amide;

[4-(N-Hydroxyamino)-2R-isobutylsuccinyl]-L-phenylalanine-N-(3-aminomethylpyridine)amide hydrochloride; and

[4-(N-Hydroxyamino)-2R-isobutylsuccinyl]-L-phenylalanine-N-[4-(2-aminoethyl)-morpholine]amide hydrochloride.

In a preferred embodiment, tricyclic butyric acid derivatives which are inhibitors of matrix metalloprotienases are employed in combination with an ACE inhibitor according to this invention. A preferred group of tricyclic butyric acid derivatives are defined by the formula:

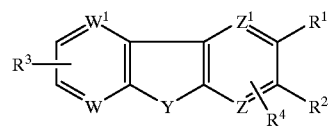

wherein one of $R^1$ or $R^2$ is 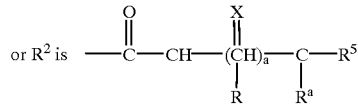

wherein X is O,

N—$OR^6$ wherein $R^6$ is hydrogen,
—$(CH_2)_n$-aryl wherein n is zero or an integer of 1 to 5, alkyl, or
—$(CH_2)_n$-cycloalkyl wherein n is as defined above, or

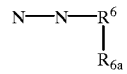

wherein $R^6$ and $R^{6a}$ are each
the same or different and each is as defined above for $R^6$;

R and $R^a$ are each the same or different and each is hydrogen,
—$(CH_2)_n$-aryl wherein n is as defined above,
—$(CH_2)_n$-heteroaryl wherein n is as defined above,
—$(CH_2)_p$-$R^7$-$(CH_2)_q$-aryl wherein $R^7$ is O or S and p or q is each zero or an integer of 1 to 5 and the sum of p+q equals an integer of 5,
—$(CH_2)_p$-$R^7$-$(CH_2)_q$-heteroaryl
wherein p, q, and $R^7$ are as defined above, alkyl,
—$(CH_2)_n$-cycloalkyl wherein n is as defined above, or
—$(CH_2)_r$—$NH_2$ wherein r is an integer of 1 to 9;

a is zero or an integer of 1 to 3;
$R^5$ is OH,
$OR^6$ wherein $R^6$ is as defined above,

wherein $R^6$ and $R^{6a}$ are each
the same or different and are as defined above for $R^6$, or NH—$OR^6$ wherein $R^6$ is as defined above;

$R^3$ and $R^4$ are each the same or different and each is hydrogen,
alkyl,
$NO_2$,
halogen,
$OR^6$ wherein $R^6$ is as defined above,
CN,
$CO_2R^6$ wherein $R^6$ is as defined above,
$SO_3R^6$ wherein $R^6$ is as defined above,

CHO,

wherein R is as defined above,

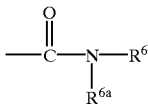

wherein $R^6$ and $R^{6a}$ are each the same or different and are as defined above for $R^6$, or 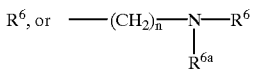

wherein $R^6$ and $R^{6a}$ are each the same or different and are as defined above for $R^6$;

W, $W^1$, Z, and $Z^1$ are each the same or different and each is $CR^3$ wherein $R^3$ is as defined above, or N providing only one of W or $W^1$ is N and/or only one of Z or $Z^1$ is N; and Y is

wherein R is as defined above,
—O—,
—S—$(O)_m$— wherein m is zero or an integer of 1 or 2,
—$CH_2$—,

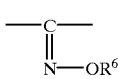

wherein $R^6$ is as defined above,

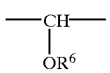

wherein $R^6$ is as defined above,

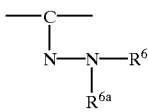

wherein $R^6$ and $R^{6a}$ are the same or different and are as defined above for $R^6$,

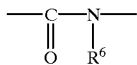

1 wherein $R^6$ is as defined above,

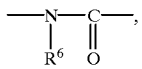

wherein $R^6$ is as defined above,

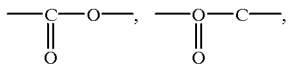

—$CH_2$—O—,
—$CH_2$—,
—$CH_2$—$S(O)_m$— wherein m is as defined above,
—$S(O)_m$—$CH_2$— wherein m is as defined above,

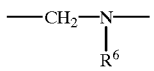

wherein $R^6$ is as defined above,

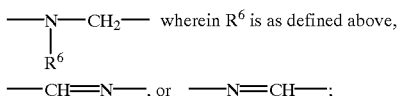

—CH=N—, or —N=CH—;

wherein $R^6$ is as defined above,
with the proviso that when X is O, and $R^5$ is not NH—$OR^6$, at least one of R or $R^a$ is not hydrogen; and corresponding isomers thereof; or a pharmaceutically acceptable salt thereof.

Typical compounds from this class include:
4-Dibenzofuran-2-yl-4-hydroxyimino-butyric acid;
2-(2-Dibenzofuran-2-yl-2-hydroxyimino-ethyl)-4-methyl-pentanoic acid;
2-(2-Dibenzofuran-2-yl-2-hydroxyimino-ethyl)-5-phenyl-pentanoic acid;
4-Dibenzofuran-2-yl-4-hydroxyimino-2-phenethyl-butyric acid;
5-(4-Chloro-phenyl)-2-(2-dibenzofuran-2-yl-2-hydroxyimino-ethyl)-pentanoic acid;
2-(2-Dibenzofuran-2-yl -2-hydroxyimino-ethyl)-5-(4-fluoro-phenyl)-pentanoic acid;
2-(2-Dibenzofuran-2-yl-2-hydroxyimino-ethyl)-5-(4-methoxy-phenyl)- pentanoic acid;
2-(2-Dibenzofuran-2-yl-2-hydroxyimino-ethyl)-5-p-tolyl-pentanoic acid;
3-(Dibenzofuran-2-yl-hydroxyimino-methyl)-5-methyl-hexanoic acid;
3-(Dibenzofuran-2-yl-hydroxyimino-methyl)-6-phenyl-hexanoic acid;
3-(Dibenzofuran-2-yl-hydroxyimino-methyl)-5-phenyl-pentanoic acid;
6-(4-Chloro-phenyl)-3-(dibenzofuran-2-yl-hydroxyimino-methyl)-hexanoic acid;
3-(Dibenzofuran-2-yl-hydroxyimino-methyl )-6-(4-fluoro-phenyl)-hexanoic acid;
3-(Dibenzofuran-2-yl-hydroxyimino-methyl)-6-(4-methoxyphenyl)-hexanoic acid; and 3-(Dibenzofuran-2-yl-hydroxyimino-methyl)-6-p-tolyl-hexanoic acid; and corresponding isomers thereof; or a pharmaceutically acceptable salt thereof.

Tricyclic butyric acids having an a-amino substituent are defined by the formula:

$$R^1 - \text{[tricyclic ring system with W, W', Y, Z, Z', R^2]} - C(X) - CH_2CH(NR_4R_5)COR_3$$

wherein:

X is O, $NOR_9$, S, OH, SH, $$N-N\begin{matrix}R_7\\R_{7a}\end{matrix};$$

and $R_{7a}$ independently are
  hydrogen,
  $C_1-C_{20}$ alkyl or substituted $C_1-C_{20}$ alkyl,
  $(CH_2)_{0-6}$-aryl,
  $(CH_2)_{0-6}$-heteroaryl, or
  $(CH_2)_{0-6}$-cycloalkyl;

$R_1$ and $R_2$ independently are
  hydrogen,
  $C_1-C_{20}$ alkyl or substituted $C_1-C_{20}$ alkyl,
  halo,
  $NO_2$,
  CN,
  CHO,
  $COR_6$,
  $COOR_6$,
  $SO_3R_6$,
  $OR_6$,
  $CONR_4R_5$,
  $(CH_2)_{0-6}$-aryl,
  $(CH_2)_{0-6}$-heteroaryl, or
  $(CH_2)_{0-6}$-cycloalkyl;

$R_6$ is hydrogen,
  $C_1-C_{20}$ alkyl or substituted $C_1-C_{20}$ alkyl;

aryl is phenyl or substituted phenyl;

$R_3$ is hydroxy,
  $O-C_1-C_{20}$ alkyl or substituted $O-C_1-C_{20}$ alkyl,
  $O-(CH_2)_{1-3}$ aryl, or
  $NHOR_6$;

$R_4$ and $R_5$ independently are hydrogen,
  $C_1-C_{20}$ alkyl or substituted $C_1-C_{20}$ alkyl,
  $(CH_2)_{0-6}$-aryl,
  $(CH_2)_{0-6}$-heteroaryl; or one of $R_4$ and $R_5$ is hydrogen and the other is:
  $COR_8$,
  $CSR_8$,
  $CONR_8R_9$,
  $CSNR_8R_9$,
  $COOR_8$,
  $COSR_8$,
  $COCHR_8$, $NR_1R_2$, $CON(R_1)-CONR_8R_9$, $CON(R_1)-COOR_8$,
  $CON(R_1)-COSR_8$, or $CON(R_1)-SO_2NR_8R_9$; $CON(R_1)-SO_3R_8$;

Y is $-N(R_1)-$, $-O-$, $-S(O)_{0,1\text{ or }2}-$, $-CH_2-$, $$-\underset{O}{\overset{\|}{C}}-, \quad -\underset{NOR_8}{\overset{\|}{C}}-, \quad -\underset{OR_8}{\overset{|}{CH}}-, \quad -\underset{N-N-R_8R_9}{\overset{\|}{C}}-,$$

$$-\underset{O}{\overset{\|}{C}}-N(R_8)-, \quad 2-C(R_8)-O, \quad -CH_2-O-,$$

$-O-CH_2-$, $-CH_2S(O)_{0,1\text{ or }2}-$,
$-S(O)_{0,1\text{ or }2}-CH_2-$, $-CH_2-N(R_8)-$,
$-N(R_8)-CH_2-$, $-CH=N$, or $-N=CH-$;

$R_8$ and $R_9$ independently are
  hydrogen
  $C_1-C_{20}$ alkyl or substituted $C_1-C_{20}$ alkyl,
  $(CH_2)_{0-6}$-aryl,
  $(CH_2)_{0-6}$-heteroaryl, or
  $(CH_2)_{0-6}$-cycloalkyl;

W, W$^1$, Z, and Z$^1$ independently are CR$^1$ or N; and the pharmaceutically acceptable salts, isomers, stereoisomers, and solvates thereof Specific examples of compounds to be employed in the present method include:

(S)-4-Dibenzofuran-2-yl-4-oxo-2-(2,2,2-trifluoroacetylamino)-butyric acid;
(R)-4-Dibenzofuran-2-yl-4-oxo-2-(2,2,2-trifluoroacetylamino)-butyric acid;
(S)-2-Amino-4-dibenzofuran-2-yl-4-oxo-butyric acid
(S)-2-Acetylamino-4-dibenzofuran-2-yl-4-oxo-butyric;
(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]-4-dibenzofuran-2-yl-4-oxo-butyric acid;
(S)-4-Dibenzofuran-2-yl-4-oxo-2-(dodecanoylamino)-butyric acid;
(S)-4-Dibenzofuran-2-yl-4-oxo-2-(dodecanoyl-amino)-butyric acid;
(S)-4-Dibenzofuran-2-yl-4-oxo-2-(2,2,2-trifluoroacetylamino)-butyric acid;
(R)-4-Dibenzofuran-2-yl-4-oxo-2-(2,2,2-trifluoroacetylamino)-butyric acid;
(S)-2-Amino-4-dibenzofuran-2-yl-4-oxo-butyric acid;
(S)-2-Acetylamino-4-dibenzofuran-2-yl-4-oxo-butyric acid;

(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid;
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]-4-dibenzofuran-2-yl-4-oxo-butyric acid;
(S)-4-Dibenzofuran-2-yl-4-oxo-2-(octanoylamino)-butyric acid; and
(S)-4-Dibenzofuran-2-yl-4-oxo-2-(dodecanoylamino)-butyric acid.

Tricyclic sulfonamide matrix metalloproteinase inhibitors include compounds of the formula

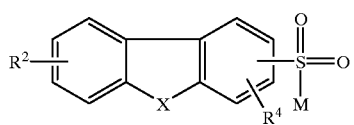

wherein M is a natural (L) alpha amino acid derivative having the structure

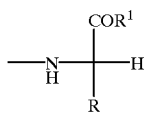

X is O, S, S(O)$_n$, CH$_2$, CO, or NH;
R is a side chain of a natural alpha amino acid;
R$^1$ is C$_1$–C$_5$ alkoxy, hydroxy, or —NHOR$^5$;
R$^2$ and R$^4$ are independently hydrogen, —C$_1$–C$_5$ alkyl, —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;
each R$^5$ and R$^6$ are independently hydrogen or C$_1$–C$_5$ alkyl; and
n is 0 to 2, and the pharmaceutically acceptable salts, ester, amides, and prodrugs thereof.

Specific compounds from this class to be employed include:
(L)-2-(Dibenzofuran-2-sulfonylamino)-4-methyl-pentanoic acid;
(L)-2-(Dibenzofuran-2-sulfonylamino)-3-methyl-pentanoic acid
(L)-2-(Dibenzofuran-2-sulfonylamino)-3-phenyl-propionic acid;
(L)-2-(Dibenzofuran-2-sulfonylamino)-propionic acid;
(L)-2-(Dibenzofuran-2-sulfonylamino)-3-methyl-butyric acid;
(Dibenzofuran-2-sulfonylamino)-acetic acid;
(L)-2-(Dibenzofuran-2-sulfonylamino)-succinic acid;
(L)-2-(Dibenzofuran-2-sulfonylamino)-3-tritylsulfanyl-propionic acid;
(L)-2-(Dibenzofuran-2-sulfonylamino)-3-mercapto-propionic acid;
(L)-2-(Dibenzofuran-2-sulfonylamino)-3-methyl-pentanoic acid hydroxyamide;
(L)-2-(Dibenzofuran-2-sulfonylamino)-4-methyl-pentanoic acid;
(L)-2-(Dibenzofuran-2-sulfonylamino)-3-methyl-pentanoic acid;
(L)-2-(Dibenzofuran-2-sulfonylamino)-3-phenyl-propionic acid;
(L)-2-(Dibenzofuran-2-sulfonylamino)-propionic acid;
(L)-2-(Dibenzofuran-2-sulfonylamino)-3-methyl-butyric acid;
(Dibenzofuran-2-sulfonylamino)-acetic acid;
(L)-2-(Dibenzofuran-2-sulfonylamino)-succinic acid;
(L)-2-(Dibenzofuran-2-sulfonylamino)-3-tritylsulfanyl-propionic acid;
(L)-2-(Dibenzofuran-2-sulfonylamino)-3-mercapto-propionic acid; and
(L)-2-(Dibenzofuran-2-sulfonylamino)-3-methyl-pentanoic acid hydroxyamide.

Additional tricyclic sulfonamides are defined by the formula:

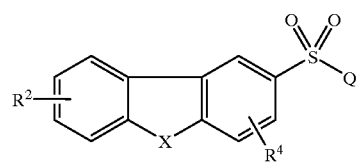

wherein Q is an un-natural amino acid;
X is O, S, S(O)$_n$, CH$_2$, CO, or NH;
R$^2$ and R$^4$ are independently hydrogen, C$_1$–C$_5$ alkyl, —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;
each R$^5$ and R$^6$ are independently hydrogen or C$_1$–C$_5$ alkyl; and
n is 0 to 2, and the pharmaceutically acceptable salts, esters, amides, and prodrugs thereof.

Specific examples of such compounds include:
(S)-2-(Dibenzofuran-2-sulfonylamino)-4-phenyl-butyric acid;
2 (S)-3-[(Dibenzofuran-2-sulfonylamino)-methyl]-5-methyl-hexanoic acid;
(S)-2-(Dibenzofuran-2-sulfonylamino)-4-phenyl-butyric acid; and
2 (S)-3-[(Dibenzofuran-2-sulfonylamino)-methyl]-5-methyl-hexanoic acid.

Another general class of matrix metalloproteinase inhibitors, which are useful in combination with ACE inhibitors are biphenyl butyric acid derivatives, including compounds of the formula:

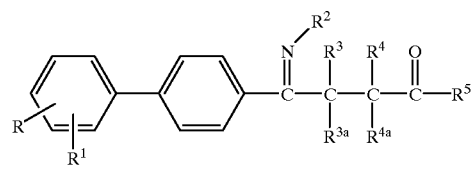

wherein R and R$^1$ are the same or different and are
hydrogen,
alkyl,
halogen,
nitro,
cyano,
trifluoromethyl,
—OR$^6$ wherein R$^6$ is hydrogen, alkyl,
aryl,
arylalkyl,
heteroaryl, or
cycloalkyl,

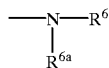

wherein $R^6$ and $R^{6a}$ are the same or different and are as defined above for $R^6$,

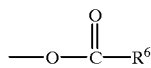

wherein $R^6$ is as defined above,

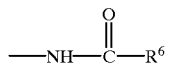

wherein $R^6$ is as defined above,

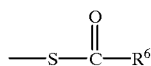

wherein $R^6$ is as defined above,
—$SR^6$ wherein $R^6$ is as defined above,

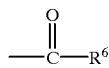

wherein $R^6$ is as defined above,
—$CH_2$—$OR^6$ wherein $R^6$ is as defined above,

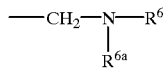

wherein $R^6$ and $R^{6a}$ are the same or different and are as defined above for $R^6$,

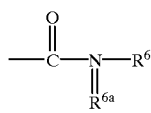

wherein $R^6$ and $R^{6a}$ are the same or different and are as defined above for $R^6$,

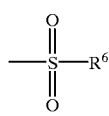

wherein $R^6$ is as defined above,
cycloalkyl, or
heteroaryl, with the proviso that R and $R^1$ are not both hydrogen;

$R^2$ is —$OR^6$ wherein $R^6$ is as defined above, or

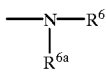

wherein $R^6$ and $R^{6a}$ are the same or different and are as defined above for $R^6$;

$R^3$, $R^{3a}$, $R^4$, and $R^{4a}$ are the same or different and are
hydrogen,
fluorine,
alkyl,
—$(CH_2)_n$-aryl wherein n is an integer from 1 to 6,
—$(CH_2)_n$-heteroaryl wherein n is as defined above,
—$(CH_2)_n$-cycloalkyl wherein n is as defined above,
—$(CH_2)_p$—X—$(CH_2)_q$-aryl wherein X is O, S, SO, SO—, or NH, and p and q are each zero or an integer of 1 to 6, and the sum of p+q is not greater than six,
—$(CH_2)_p$—X—$(CH_2)_q$-heteroaryl wherein X, p, and q are as defined above, or
—$(CH_2)_n$-$R^7$ wherein $R^7$ is
N-phthalimido,
N-2,3-naphthyimido,
—$OR^6$ wherein $R^6$ is as defined above,

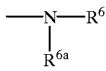

wherein $R^6$ and $R^{6a}$ are the same or different and are as defined above for $R^6$,
—$SR^6$ where $R^6$ is as defined above,

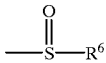

wherein $R^6$ is as defined above,

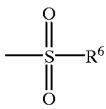

wherein $R^6$ is as defined above,

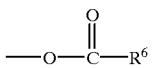

wherein $R^6$ is as defined above,

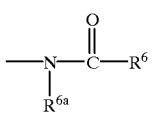

wherein $R^6$ and $R^{6a}$ are the same or different and are as defined above for $R^6$,

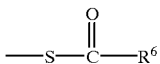

wherein $R^6$ is as defined above,

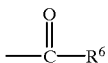

wherein $R^6$ is as defined above,

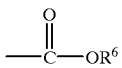

wherein $R^6$ is as defined above, or

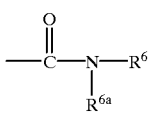

wherein $R^6$ and $R^{6a}$ are the same
or different and are as defined above for $R^6$, and n is as defined above;
$R^5$ is OH or SH; with the proviso that $R^3$, $R^{3a}$, $R^4$, and $R^{4a}$ are hydrogen or at least one of $R^3$, $R^{3a}$, $R^4$, or $R^{4a}$ is fluorine; and corresponding isomers thereof; or a pharmaceutically acceptable salt thereof.

Typical compounds from this class that are routinely utilized together with an ACE-inhibitor to treat and prevent heart failure and ventricular dilation include:
4-(4'-Chloro-biphenyl-4-yl)-4-hydroxyimino-butyric acid;
4-(4'-Bromo-biphenyl-4-yl)-4-hydroxyimino-butyric acid;
4-(4'-Chloro-biphenyl-4-yl)-4-(dimethylhydrazono)-butyric acid;
4-(4'-Fluoro-biphenyl-4-yl)-4-hydroxyimino-butyric acid;
(±)-4-(4'-Chloro-biphenyl-4-yl)-4-hydroxy-butyric acid;
4-(4'-Bromo-2'-fluoro-biphenyl-4-yl)-4-hydroxyimino-butyric acid;
(±)-4-(4'-Chloro-biphenyl-4-yl)-3-fluoro-4-oxo-butyric acid;
4-(2',4'-Dichloro-biphenyl-4-yl)-4-hydroxyimino-butyric acid;
4-(2',4'-Difluoro-biphenyl-4-yl)-4-hydroxyimino-butyric acid;
(±)-4-(4'-Chloro-biphenyl-4-yl)-4-hydroxyimino-2-fluoro-2-(3-phenylpropyl)-butyric acid;
(±)-4-(4'-Chloro-biphenyl-4-yl)-4-hydroxyimino-2-fluoro-2-(2-phenylethyl)-butyric acid;
(±)-4-(4'-Chloro-biphenyl-4-yl)-4-hydroxyimino-2-fluoro-2-(3-phthalimidopropyl)-butyric acid;
(±)-4-(4'-Chloro-biphenyl-4-yl)-4-hydroxyimino-2-fluoro-2-(phenylthiomethyl)-butyric acid;
4-(4'-Chloro-2'-fluoro-biphenyl-4-yl)-4-hydroxyimino-butyric acid;
4-Hydroxyimino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxyimino-butyric acid;
(±)-4-(4'-Chloro-biphenyl-4-yl)-4-hydroxyimino-2-fluoro-2-(1H-indol-3-yl)methyl-butyric acid;
(±)-4-(4'-Chloro-biphenyl-4-yl)-4-hydroxyimino-2-fluoro-2-methyl-butyric acid;
(±)-2-[2-(4'-Chloro-biphenyl-4-yl)-2-hydroxyiminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxyimino-butyric acid;
(±)-2-[2-(4'-Chloro-biphenyl-4-yl)-2-hydroxyiminoethyl]-6-(1,3-dioxo-1,3-dihydro-isoindol-2-yl)-2-fluoro-hexanoic acid;
(±)-4-(4'-Chloro-biphenyl-4-yl)-4-hydroxyimino-2-fluoro-2-[2-(phenyl-ethylcarbamoyl)-ethyl]-butyric acid;
4-(4'-Chloro-biphenyl-4-yl)-3,3-difluoro-4-hydroxyimino-butyric acid;
(±)-4-(4'-Chloro-biphenyl-4-yl)-3,3-dimethyl-2-fluoro-4-hydroxyimino-butyric acid;
(±)-4-(4'-Chloro-biphenyl-4-yl)-2,2-dimethyl-3-fluoro-4-hydroxyimino-butyric acid;
4-(4'-Chloro-biphenyl-4-yl)-2,2-difluoro-4-hydroxyimino-butyric acid; and
4-(4'-Chloro-biphenyl-4-yl)-2,2,3,3-tetrafluoro-4-hydroxyimino-butyric acid.

A compound selected from the group consisting of:
4-(4'-Chloro-biphenyl-4-yl)-4-hydroxyimino-butyric acid;
4-(4'-Bromo-biphenyl-4-yl)-4-hydroxyimino-butyric acid;
4-(4'-Chloro-biphenyl-4-yl)-4-(dimethylhydrazono)-butyric acid;
4-(4'-Fluoro-biphenyl-4-yl)-4-hydroxyimino-butyric acid;
(±)-4-(4'-Chloro-biphenyl-4-yl)-4-hydroxy-butyric acid;
4-(4'-Bromo-2'-fluoro-biphenyl-4-yl)-4-hydroxyimino-butyric acid;
(±)-4-(4'-Chloro-biphenyl-4-yl)-3-fluoro-4-oxo-butyric acid;
4-(2',4'-Dichloro-biphenyl-4-yl)-4-hydroxyimino-butyric acid;
4-(2',4'-Difluoro-biphenyl-4-yl)-4-hydroxyimino-butyric acid;
(±)-4-(4'-Chloro-biphenyl-4-yl)-4-hydroxyimino-2-fluoro-2-(3-phenylpropyl)-butyric acid;
(±)-4-(4'-Chloro-biphenyl-4-yl)-4-hydroxyimino-2-fluoro-2-(2-phenylethyl)-butyric acid;
(±)-4-(4'-Chloro-biphenyl-4-yl)-4-hydroxyimino-2-fluoro-2-(3-phthalimidopropyl)-butyric acid;
(±)-4-(4'-Chloro-biphenyl-4-yl)-4-hydroxyimino-2-fluoro-2-(phenylthiomethyl)-butyric acid;
4-(4'-Chloro-2'-fluoro-biphenyl-4-yl)-4-hydroxyimino-butyric acid;
4-Hydroxyimino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxyimino-butyric acid;
(±)-4-(4'-Chloro-biphenyl-4-yl)-4-hydroxyimino-2-fluoro-2-(1H-indol-3-yl)methyl-butyric acid;
(±)-4-(4'-Chloro-biphenyl-4-yl)-4-hydroxyimino-2-fluoro-2-methyl-butyric acid;
(±)-2-[2-(4'-Chloro-biphenyl-4-yl)-2-hydroxyiminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxyimino-butyric acid;
(±)-2-[2-(4'-Chloro-biphenyl-4-yl)-2-hydroxyiminoethyl]-6-(1,3-dioxo-1,3-dihydro-isoindol-2-yl)-2-fluoro-hexanoic acid;
(±)-4-(4'-Chloro-biphenyl-4-yl)-4-hydroxyimino-2-fluoro-2-[2-(phenyl-ethylcarbamoyl)-ethyl]-butyric acid;

4-(4'-Chloro-biphenyl-4-yl)-3,3-difluoro-4-hydroxyimino-butyric acid;

(±)-4-(4'-Chloro-biphenyl-4-yl)-3,3-dimethyl-2-fluoro-4-hydroxyimino-butyric acid;

(±)-4-(4'-Chloro-biphenyl-4-yl)-2,2-dimethyl-3-fluoro-4-hydroxyimino-butyric acid;

4-(4'-Chloro-biphenyl-4-y:)-2,2-difluoro-4-hydroxyimino-butyric acid; and 4-(4'-Chloro-biphenyl-4-yl)-2,2,3,3-tetrafluoro-4-hydroxyimino-butyric acid.

Biphenyl sulfonamides are also particularly good in the present method. Such compounds include those of the formula:

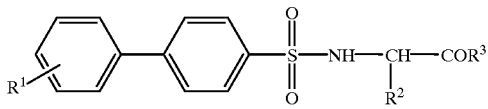

wherein:

$R^1$ is $C_1$–$C_6$ alkyl, halo, nitro, $NR^4R^5$, cyano, $OR^4$, and $COOR^4$;

$R^2$ is $C_1$–$C_6$ alkyl, optionally substituted by phenyl, substituted phenyl, $NR^4R^5$, $OR^6$, carboxy, carboxamido,

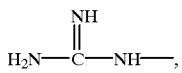

thio, methylthio, indole, imidazole, phthalimido, phenyl, and substituted phenyl;

$R^3$ is OH, $OC_1$–$C_6$ alkyl, or NHOH; $R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl.

Specific compounds which can be employed include a compound of the above formula wherein $R^1$ is at the 4' position.

Another class of matrix metalloproteinase inhibitors useful in the present method are the heterocyclic substituted phenyl butyric acid derivatives, for example those defined by the formula:

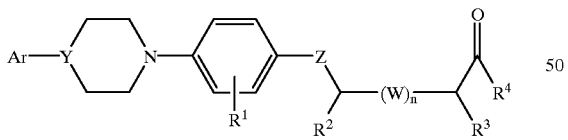

Ar is selected from phenyl,
  phenyl substituted with
    alkyl,
    $NO_2$,
    halogen,
    $OR^5$ wherein $R^5$ is hydrogen or alkyl,
    CN,
    $CO_2R^5$ wherein $R^5$ is as defined above,
    $SO_3R^5$ wherein $R^5$ is as defined above,
    CHO,
    $COR^5$ wherein $R^5$ is as defined above,
    $CONHR^5$ wherein $R^5$ is as defined above, or
    $NHCOR^5$ wherein $R^5$ is as defined above,
  2-naphthyl, or
  heteroaryl;

$R^1$ is selected from hydrogen,
  methyl,
  ethyl,
  $NO_2$,
  halogen,
  $OR^5$ wherein $R^5$ is as defined above,
  CN,
  $CO_2R^5$ wherein $R^5$ is as defined above,
  $SO_3R^5$ wherein $R^5$ is as defined above,
  CHO, or
  $COR^5$ wherein $R^5$ is as defined above;

$R^2$ and $R^3$ are the same or different and independently selected from hydrogen,
  alkyl,
  —$(CH_2)_v$-aryl wherein v is an integer from 1 to 5,
  —$(CH_2)_v$-heteroaryl wherein v is as defined above,
  —$(CH_2)_v$-cycloalkyl wherein v is as defined above,
  —$(CH_2)_p$—X—$(CH_2)_q$-aryl wherein X is o or S and p and q is each zero or an integer of 1 to 5, and the sum of p+q is not greater than an integer of 5,
  —$(CH_2)_p$—X—$(CH_2)_q$-heteroaryl wherein X, p, and q are as defined above,
  —$(CH_2)_tNR^6R^{6a}$, wherein t is zero or an integer of from 1 to 9 and $R^6$ and $R^{6a}$ are each the same or different and are as defined above for $R^5$,
  —$(CH_2)_vSR^5$, wherein v and $R^5$ are as defined above,
  —$(CH_2)_vCO_2R^5$, wherein v and $R^5$ are as defined above, or
  —$(CH_2)_vCONR^6R^{6a}$, wherein $R^6$ and $R^{6a}$ are the same or
different and are as defined above for $R^5$ and v is as defined above;

$R^3$ is additionally —$(CH_2)_rR^7$ wherein r is an integer from 1 to 5 and $R^7$ is 1,3-dihydro-1,3-dioxo-2H-isoindol-2-yl, or 1,3,-dihydro-1,3-dioxo-benzo[f]isoindol-2-yl;

Y is CH or N;

wherein $R^{10}$ is as defined above for $R^2$ and $R^3$, and is independently the same or different from $R^2$ and $R^3$ provided that
  when Z is

then $R^4$ must be OH,
  C=O,
  C=$NOR^5$ wherein $R^5$ is as defined above, or
    C=N—$NR^6R^{6a}$ wherein $R^6$ and $R^{6a}$ are the same or different and are as defined above for $R^5$;

W is —$CHR^5$ wherein $R^5$ is as defined above;

n is zero or an integer of 1;

$R^4$ is OH,
  $NR^6R^{6a}$ wherein $R^6$ and $R^{6a}$ are the same or different and are as defined above for $R^5$, when $R^4$ is $NR^6R^{6a}$ then Z must be C=O or NHOR$^9$ wherein R$^9$ is hydrogen, alkyl, or benzyl; and corresponding isomers thereof; or a pharmaceutically acceptable salt thereof.

Especially preferred MMP inhibitors have the formula

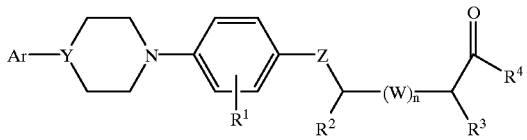

Ar is selected from phenyl,
phenyl substituted with
  alkyl,
  NO$_2$,
  halogen,
  OR$^5$ wherein R$^5$ is hydrogen or alkyl,
  CN,
  CO$_2$R$^5$ wherein R$^5$ is as defined above,
  SO$_3$R$^5$ wherein R$^5$ is as defined above,
  CHO,
  COR$^5$ wherein R$^5$ is as defined above,
  CONHR$^5$ wherein R$^5$ is as defined above, or
  NHCOR$^5$ wherein R$^5$ is as defined above,
2-naphthyl, or
heteroaryl;
R$^1$ is selected from hydrogen,
  methyl,
  ethyl,
  NO$_2$,
  halogen,
  OR$^5$ wherein R$^5$ is as defined above,
  CN,
  CO$_2$R$^5$ wherein R$^5$ is as defined above,
  SO$_3$R$^5$ wherein R$^5$ is as defined above,
  CHO, or
  COR$^5$ wherein R$^5$ is as defined above;
R$^2$ and R$^3$ are the same or different and independently selected from hydrogen,
  alkyl,
  —(CH$_2$)$_v$-aryl wherein v is an integer from 1 to 5,
  —(CH$_2$)$_v$-heteroaryl wherein v is as defined above,
  —(CH$_2$)$_v$-cycloalkyl wherein v is as defined above,
  —(CH$_2$)$_p$—X—(CH$_2$)$_q$-aryl wherein X is O or S and p and q is each zero or an integer of 1 to 5, and the sum of p+q is not greater than an integer of 5,
  —(CH$_2$)$_p$—X—(CH$_2$)$_q$-heteroaryl wherein X, p, and q are as defined above,
  —(CH$_2$)$_t$NR$^6$R$^{6a}$, wherein t is zero or an integer of from 1 to 9 and R$^6$ and R$^{6a}$ are each the same or different and are as defined above for R$^5$,
  —(CH$_2$)$_v$SR$^5$, wherein v and R$^5$ are as defined above,
  —(CH$_2$)$_v$CO$_2$R$^5$, wherein v and R$^5$ are as defined above, or
  —(CH$_2$)$_v$CONR$^6$R$^{6a}$, wherein R$^6$ and R$^{6a}$ are the same or different and are as defined above for R$^5$ and v is as defined above;
R$^3$ is additionally —(CH$_2$)$_r$R$^7$ wherein r is an integer from 1 to 5 and R$^7$ is 1,3-dihydro-1,3-dioxo-2H-isoindol-2-yl, or 1,3,-dihydro-1,3-dioxo-benzo[f]isoindol-2-yl;
Y is CH or N;

Z is

wherein R$^{10}$ is as defined above for R$^2$ and R$^3$, and is independently the same or different from R$^2$ and R$^3$ provided that
when Z is

then R$^4$ must be OH,
  C=O,
  C=NOR$^5$ wherein R$^5$ is as defined above, or
  C=N—NR$^6$R$^{6a}$ wherein R$^6$ and R$^{6a}$ are the same or different and are as defined above for R$^5$;
W is —CHR$^5$ wherein R$^5$ is as defined above;
n is zero or an integer of 1;
R$^4$ is OH,
  NR$^6$R$^{6a}$ wherein R$^6$ and R$^{6a}$ are the same or different and are as defined above for R$^5$, when R$^4$ is NR$^6$R$^{6a}$ then Z must be C=O or
  NHOR$^9$ wherein R$^9$ is hydrogen, alkyl, or benzyl; and corresponding isomers thereof; or a pharmaceutically acceptable salt thereof.

Preferred compounds to be employed include:
4-Oxo-4-[4-(4-phenyl-piperidin-1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxyimino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid;
(±)3-Methyl-5-oxo-5-[4-(4-phenyl-piperidin-1-yl)-phenyl]-pentanoic acid;
4-Oxo-4-[4-(4-phenyl-piperidin-1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxyimino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid; and
(±)3-Methyl-5-oxo-5-[4-(4-phenyl-piperidin-1-yl)-phenyl]-pentanoic acid.

A compound which is 4-oxo-4-[4-(4-phenyl-piperidin-1-yl)-phenyl]-butyric acid.

Similar compounds which are sulfonamide derivatives have the formula:

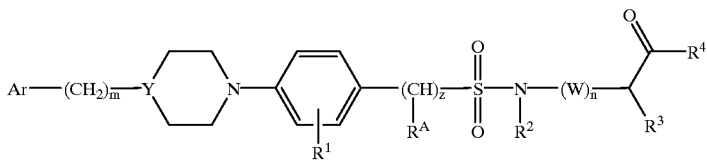

wherein:
Ar is selected from phenyl;
phenyl substituted with alkyl, —NO—, halogen, —OR$^5$, —CN, —CO—R$^5$, —SO$_3$R$^5$, —CHO, —COR$^5$, —CONHR$^5$, —NHR$^5$, or —NHCOR$^5$;
heteroaryl; or
2-naphthyl;
R$^1$ is hydrogen, methyl, —NO$_2$, —Cl, —NH$_2$, —NHCO$_2$CH$_3$, —OH, or —CO$_2$H;
R$^2$ and R$^3$ are the same or different and are independently selected from hydrogen, alkyl, —(CH$_2$)$_v$-aryl, —(CH$_2$)$_v$-heteroaryl, —(CH$_2$)$_v$-cycloalkyl, —(CH$_2$)$_p$—X—(CH$_2$)$_q$-aryl, —(CH$_2$)$_p$—X—(CH$_2$)$_q$-heteroaryl, —(CH$_2$)$_t$NR$^6$R$^{6a}$, —(CH$_2$)$_v$R$^7$, —(CH$_2$)$_v$CO$_2$R$^5$, —(CH$_2$)$_v$CONR$^6$R$^{6a}$, or —(CH$_2$)$_v$SR$^5$;
m is zero or 1;
Y is CH or N; provided that when m=1, Y does not N;
z is zero or 1;
z is zero or 1;
W is —CHR$^8$;
n is zero or 1;
R$^4$ is —OH, —NR$^6$R$^{6a}$, or —NHOR$^9$;
R$^5$ is hydrogen or alkyl;
v is 1 to 5;
X is O or S;
p and q are independently 1 to 5, provided that p+q is not greater than 5;
t is 1 to 9;
R$^6$ and R$^6$a are each the same or different and are hydrogen or alkyl;
R$^7$ is 1,3-dihydro-1,3-dioxo-2H-isoindol-2-yl, or 1,3-dihydro-1,3-dioxo-benzo[f]isoindol-2-yl;
R$^8$ is hydrogen or alkyl; and
R$^9$ is hydrogen, alkyl, or benzyl; or
a pharmaceutically acceptable salt thereof.

Specific sulfonamide derivatives to be employed in the present method include:
[4-(4-Phenyl-piperidin-1-yl)-benzenesulfonylamino]-acetic acid;
N-Hydroxy-2-[4-(4-phenyl-piperidin-1-yl)-benzenesulfonylamino]-acetamide;
3-[4-(4-Phenyl-piperidin-1-yl)-benzenesulfonylamino]-propionic acid;
(R)-4-Methyl-2-[4-(4-phenyl-piperidin-1-yl)-benzenesulfonylamino]-pentanoic acid;
(S)-4-Methyl-2-[4-(4-phenyl-piperidin-1-yl)-benzenesulfonylamino]-pentanoic acid;
(S)-3-Phenyl-2-[4-(4-phenyl-piperidin-1-yl)-benzenesulfonylamino]-propionic acid;
(R)-3-Phenyl-2-[4-(4-phenyl-piperidin-1-yl)-benzenesulfonylamino]-propionic acid;
(S)-3-(1H-Indol-3-yl)-2-[4-(4-phenyl-piperidin-1-yl)-benzenesulfonylamino]-propionic acid;
(±)-5-Phenyl-2-[4-(4-phenyl-piperidin-1-yl)-benzenesulfonylamino]-pentanoic acid;
[4-(4-Phenyl-piperazin-1-yl)-benzene-sulfonylamino]-acetic acid;
{Isobutyl-[4-(4-phenyl-piperidin-1-yl)-benzenesulfonyl]amino}-acetic acid;
(S)-4-Phenyl-2-[4-(4-phenyl-piperidin-1-yl)-benzene-sulfonylamino]-butyric acid;
(R)-2-[4-(4-Phenyl-piperidin-1-yl)-benzene-sulfonylamino]-3-tritylsulfanyl-propionic acid, sodium salt;
(R)-3-(1H-Indol-3-yl)-2-[4-(4-phenyl-piperidin-1-yl)-benzenesulfonylamino]-propionic acid, disodium salt, monohydrate;
(S)-2-{4-[-4-(4-Hydroxy-phenyl)-piperazin-1-yl]-benzenesulfonylamino}-3-phenyl-propionic acid;
(S)-2-{4-[-4-(4-Chloro-phenyl)-piperazin-1-yl]-benzenesulfonylamino}-3-phenyl-propionic acid, hydrochloride;
(R)-3-Mercapto-2-[4-(4-phenyl-piperidin-1-yl)-benzenesulfonylamino]-propionic acid, trifluoracetic acid salt;
(S)-2-[4-(4-Benzyl-piperidin-1-yl)-benzenesulfonylamino]-3-phenyl-propionic acid;
(S)-3-(4-Benzyloxy-phenyl)-2-[4-(4-phenyl-piperidin-1-yl)-benzenesulfonylamino]-propionic acid;
(S)-3-(4-Hydroxy-phenyl)-2-[4-(4-phenyl-piperidin-1-yl)-benzenesulfonylamino]-propionic acid;
(S)-3-Phenyl-2-[4-(4-phenyl-piperazin-1-yl)-benzenesulfonylamino]-propionic acid;
(S)-2-{4-[-4-(3-Methoxy-phenyl)-piperazin-1-yl]-benzenesulfonylamino}-3-phenyl-propionic acid;
(S)-2-{4-[-4-(3-Hydroxy-phenyl)-piperazin-1-yl]-benzenesulfonylamino}-3-phenyl-propionic acid hydrobromide;
(S)-2-{4-[-4-(4-Methoxy-phenyl)-piperazin-1-yl]-benzenesulfonylamino}-3-phenyl-propionic acid;
(R)-4-Methyl-2-[4-(4-phenyl-piperidin-1-yl)-benzenesulfonylamino]-pentanoic acid;
(S)-4-Methyl-2-[4-(4-phenyl-piperidin-1-yl)-benzenesulfonylamino]-pentanoic acid;
(S)-3-Phenyl-2-[4-(4-phenyl-piperidin-1-yl)-benzenesulfonylamino]-propionic acid;
(R)-3-Phenyl-2-[4-(4-phenyl-piperidin-1-yl)-benzenesulfonylamino]-propionic acid;
(S)-3-(1H-Indol-3-yl)-2-[4-(4-phenyl-piperidin-1-yl)-benzenesulfonylamino]-propionic acid;
[4-(4-Phenyl-piperidin-1-yl)-benzenesulfonylamino]-acetic acid;
N-Hydroxy-2-[4-(4-phenyl-piperidin-1-yl)-benzenesulfonylamino]-acetamide;
3-[4-(4-Phenyl-piperidin-1-yl)-benzenesulfonylamino]-propionic acid;
(R)-4-Methyl-2-[4-(4-phenyl-piperidin-1-yl)-benzenesulfonylamino]-pentanoic acid;
(S)-4-Methyl-2-[4-(4-phenyl-piperidin-1-yl)-benzenesulfonylamino]-pentanoic acid;
(S)-3-Phenyl-2-[4-(4-phenyl-piperidin-1-yl)-benzenesulfonylamino]-propionic acid;

(R)-3-Phenyl-2-[4-(4-phenyl-piperidin-1-yl)-benzenesulfonylamino]-propionic acid;
(S)-3-(1H-Indol-3-yl)-2-[4-(4-phenyl-piperidin-1-yl)-benzenesulfonylamino]-propionic acid;
(±)-5-Phenyl-2-[4-(4-phenyl-piperidin-1-yl)-benzenesulfonylamino]-pentanoic acid;
[4-(4-Phenyl-piperazin-1-yl)-benzene-sulfonylamino]-acetic acid;
{Isobutyl-[4-(4-phenyl-piperidin-1-yl)-benzenesulfonyl]amino}-acetic acid;
(S)-4-Phenyl-2-[4-(4-phenyl-piperidin-1-yl)-benzenesulfonylamino]-butyric acid;
(R)-2-[4-(4-Phenyl-piperidin-1-yl)-benzenesulfonylamino]-3-tritylsulfanyl-propionic acid, sodium salt;
(R)-3-(1H-Indol-3-yl)-2-[4-(4-phenyl-piperidin-1-yl)-benzenesulfonylamino]-propionic acid, disodium salt, monohydrate;
(S)-2-{4-[-4-(4-Hydroxy-phenyl)-piperazin-1-yl]-benzenesulfonylamino}-3-phenyl-propionic acid;
(S)-2-{4-[-4-(4-Chloro-phenyl)-piperazin-1-yl]-benzenesulfonylamino}-3-phenyl-propionic acid, hydrochloride;
(R)-3-Mercapto-2-[4-(4-phenyl-piperidin-1-yl)-benzenesulfonylamino]-propionic acid, trifluoracetic acid salt;
(S)-2-[4-(4-Benzyl-piperidin-1-yl)-benzenesulfonylamino]-3-phenyl-propionic acid;
(S)-3-(4-Benzyloxy-phenyl)-2-[4-(4-phenyl-piperidin-1-yl)-benzenesulfonylamino]-propionic acid;
(S)-3-(4-Hydroxy-phenyl)-2-[4-(4-phenyl-piperidin-1-yl)-benzenesulfonylamino]-propionic acid;
(S)-3-Phenyl-2-[4-(4-phenyl-piperazin-1-yl)-benzenesulfonylamino]-propionic acid;
(S)-2-{4-[-4-(3-Methoxy-phenyl)-piperazin-1-yl]-benzenesulfonylamino}-3-phenyl-propionic acid;
(S)-2-{4-[-4-(3-Hydroxy-phenyl)-piperazin-1-yl]-benzenesulfonylamino}-3-phenyl-propionic acid hydrobromide;
(S)-2-{4-[-4-(4-Methoxy-phenyl)-piperazin-1-yl]-benzenesulfonylamino}-3-phenyl-propionic acid;
(R)-4-Methyl-2-[4-(4-phenyl-piperidin-1-yl)-benzenesulfonylamino]-pentanoic acid;
(S)-4-Methyl-2-[4-(4-phenyl-piperidin-1-yl)-benzenesulfonylamino]-pentanoic acid;
(S)-3-Phenyl-2-[4-(4-phenyl-piperidin-1-yl)-benzenesulfonylamino]-propionic acid;
(R)-3-Phenyl-2-[4-(4-phenyl-piperidin-1-yl)-benzenesulfonylamino]-propionic acid; and
(S)-3-(1H-Indol-3-yl)-2-[4-(4-phenyl-piperidin-1-yl)-benzenesulfonylamino]-propionic acid.

Additional specific compounds which can be used include:
2-(Dibenzofuran-2-sulfonylamino)-3-(4-fluoro-phenyl)-propionic acid;
2-(Dibenzofuran-2-sulfonylamino)-3-phenyl-propionic acid;
3-(4-tert-Butoxy-phenyl)-2-(dibenzofuran-2-sulfonylamino)-propionic acid;
(Dibenzofuran-2-sulfonylamino)-phenyl-acetic acid;
3-tert-Butoxy-2-(dibenzofuran-2-sulfonylamino)-propionic acid;
2-(Dibenzofuran-2-sulfonylamino)-3-(1H-imidazol-4-yl)-propionic acid;
2-(Dibenzofuran-2-sulfonylamino)-3-hydroxy-propionic acid;
3-Benzyloxy-2-(dibenzofuran-2-sulfonylamino)-propionic acid;
6-Benzyloxycarbonylamino-2-(dibenzofuran-2-sulfonylamino)-hexanoic acid;
5-Benzyloxycarbonylamino-2-(dibenzofuran-2-sulfonylamino)-pentanoic acid;
(Dibenzofuran-2-sulfonylamino)-(4-methoxy-phenyl)-acetic acid;
3-Chloro-2-(dibenzofuran-2-sulfonylamino)-propionic acid;
3-(4-Benzyloxy-phenyl)-2-(dibenzofuran-2-sulfonylamino)-propionic acid;
2-(Dibenzofuran-2-sulfonylamino)-5-p-tolyl-sulfanylamino-pentanoic acid;
2-(Dibenzofuran-2-sulfonylamino)-4-mercapto-butyric acid;
3-(4-Bromo-phenyl)-2-(dibenzofuran-2-sulfonyl-amino)-propionic acid;
2-(Dibenzofuran-2-sulfonylamino)-butyric acid;
1-(Dibenzofuran-2-sulfonylamino)-cyclopropane-carboxylic acid;
3-(4-Chloro-phenyl)-2-(dibenzofuran-2-sulfonyl-amino)-propionic acid;
2-(Dibenzofuran-2-sulfonylamino)-3-(1H-indol-3-yl)-propionic acid;
2-(4'-Bromo-biphenyl-4-sulfonylamino)-6-(4-fluoro-benzenesulfonylamin o)-hexanoic-acid;
2-(4'-Bromo-biphenyl-4-sulfonylamino)-6-(4-methoxy-benzenesulfonylam ino)-hexanoic acid;
6-(4-Bromo-benzenesulfonylamino)-2-(4'-bromo-biphenyl-4-sulfonylamino)-hexanoic-acid;
6-(2-Acetylamino-thiazole-5-sulfonylamino)-2-(4'-bromo-biphenyl-4-sulfo nylamino)-hexanoic-acid;
6-(4-Acetylamino-benzenesulfonylamino)-2-(4'-bromo-biphenyl-4-sulfony lamino)-hexanoic-acid;
6-Benzenesulfonylamino-2-(4'-bromo-biphenyl-4-sulfonylamino)-hexanoi c acid;
2-(4'-Bromo-biphenyl-4-sulfonylamino)-6-(pentane-1-sulfonylamino)-hexanoic acid;
2-(4'-Bromo-biphenyl-4-sulfonylamino)-6-(naphthalene-2-sulfonylamino)-hexanoic-acid;
2-(4'-Bromo-biphenyl-4-sulfonylamino)-6-(naphthalene-1-sulfonylamino)-hexanoic-acid;
2-(4'-Bromo-biphenyl-4-sulfonylamino)-6-(2-phenyl-ethenesulfonylamino)-hexanoic-acid;
2-(4'-Bromo-biphenyl-4-sulfonylamino)-6-phenyl-acetylamino-hexanoic acid;
2-(4'-Bromo-biphenyl-4-sulfonylamino)-6-[2-(4-chloro-phenoxy)-acetyla mino]-hexanoic acid;
2-(4'-Bromo-biphenyl-4-sulfonylamino)-6-[2-(4-chloro-phenoxy)-2-methy l-propionylamino]-hexanoic acid;
2-(4'-Bromo-biphenyl-4-sulfonylamino)-6-[2-(pyridin-4-ylsulfanyl)-acetylamino]-hexanoic acid;
2-(4'-Bromo-biphenyl-4-sulfonylamino)-6-[2-(2,4-dichloro-phenoxy)-acet ylamino]-hexanoic acid;
2-(4'-Bromo-biphenyl-4-sulfonylamino)-6-(2-thiophen-2-yl-acetylamino)-hexanoic acid;
2-(4'-Bromo-biphenyl-4-sulfonylamino)-6-(3-phenyl-acryloylamino)-hexa noic acid;
2-(4'-Bromo-biphenyl-4-sulfonylamino)-6-(7-phenyl-heptanoylamino)-hexanoic acid;
2-(4'-Bromo-biphenyl-4-sulfonylamino)-6-[2-(2-trifluoromethyl-phenyl)-a cetylamino]-hexanoic acid;
2-(4'-Bromo-biphenyl-4-sulfonylamino)-6-(2-phenoxy-butyrylamino)-hexanoic acid;
2-(4'-Bromo-biphenyl-4-sulfonylamino)-6-(2-phenyl-sulfanyl-acetylamino)-hexanoic acid;
2-(4'-Bromo-biphenyl-4-sulfonylamino)-6-(2-phenoxy-acetylamino)-hexan oic acid;
2-(4'-Bromo-biphenyl-4-sulfonylamino)-6-[2-(3,4-dimethoxy-phenyl)-acetylamino]-hexanoic acid;

2-(4'-Bromo-biphenyl-4-sulfonylamino)-6-[2-(4-tert-butyl-phenoxy)-acetylamino]-hexanoic acid;
2-(4'-Bromo-biphenyl-4-sulfonylamino)-6-[3-(3,4-dimethoxy-phenyl)-propionylamino]-hexanoic acid;
2-(4'-Bromo-biphenyl-4-sulfonylamino)-6-(2-cyclopent-1-enyl-acetylamino)-hexanoic acid;
2-(4'-Bromo-biphenyl-4-sulfonylamino)-6-[2-(4-methoxy-phenoxy)-acetylamino]-hexanoic acid;
2-(4'-Bromo-biphenyl-4-sulfonylamino)-6-[2-(naphthalen-1-yloxy)-acetylamino]-hexanoic acid;
2-(4'-Bromo-biphenyl-4-sulfonylamino)-6-[2-(4-nitro-phenoxy)-acetylamino]-hexanoic acid;
2-(4'-Bromo-biphenyl-4-sulfonylamino)-6-[4-(4-chloro-3-methyl-phenoxy)-butyrylamino]-hexanoic acid;
2-(4'-Bromo-biphenyl-4-sulfonylamino)-6-[3-(4-methoxy-phenyl)-propionylamino]-hexanoic acid;
2-(4'-Bromo-biphenyl-4-sulfonylamino)-6-(2-pyridin-3-yl-acetylamino)-hexanoic acid;
6-(2-Benzo[1,3]dioxol-5-yl-acetylamino)-2-(4'-bromo-biphenyl-4-sulfonylamino)-hexanoic acid;
2-(4'-Bromo-biphenyl-4-sulfonylamino)-6-(2-pyridin-2-yl-acetylamino)-hexanoic acid;
2-(4'-Bromo-biphenyl-4-sulfonylamino)-6-[2-(4-tert-butyl-phenoxy)-acetylamino]-hexanoic acid;
2-(4'-Bromo-biphenyl-4-sulfonylamino)-6-[3-(3,4-dimethoxy-phenyl)-propionylamino]-hexanoic acid;
2-(4'-Bromo-biphenyl-4-sulfonylamino)-6-(2-cyclopent-1-enyl-acetylamino)-hexanoic acid;
2-(4'-Bromo-biphenyl-4-sulfonylamino)-6-[2-(4-methoxy-phenoxy)-acetyl amino]-hexanoic acid;
2-(4'-Bromo-biphenyl-4-sulfonylamino)-6-[2-(naphthalen-1-yloxy)-acetyla-mino]-hexanoic acid;
2-(4'-Bromo-biphenyl-4-sulfonylamino)-6-[2-(4-nitro-phenoxy)-acetylamino]-hexanoic acid;
2-(4'-Bromo-biphenyl-4-sulfonylamino)-6-[4-(4-chloro-3-methyl-phenoxy)-butyrylamino]-hexanoic acid;
2-(4'-Bromo-biphenyl-4-sulfonylamino)-6-[3-(4-methoxy-phenyl)-propionylamino]-hexanoic acid;
2-(4'-Bromo-biphenyl-4-sulfonylamino)-6-(2-pyridin-3-yl-acetylamino)-hexanoic acid;
6-(2-Benzo[1,3]dioxol-5-yl-acetylamino)-2-(4'-bromo-biphenyl-4-sulfonyl amino)-hexanoic acid;
2-(4'-Bromo-biphenyl-4-sulfonylamino)-6-(2-pyridin-2-yl-acetylamino)-hexanoic acid;
2-(4'-Bromo-biphenyl-4-sulfonylamino)-6-[4-(4-nitro-phenyl)-butyrylamino]-hexanoic acid;
2-(4'-Bromo-biphenyl-4-sulfonylamino)-6-[2-(4-tert-butyl-phenoxy)-acetyl amino]-hexanoic acid;
2-(4'-Bromo-biphenyl-4-sulfonylamino)-6-[3-(3,4-dimethoxy-phenyl)-propionylamino]-hexanoic acid;
2-(4'-Bromo-biphenyl-4-sulfonylamino)-6-(2-cyclopent-1-enyl-acetylamino)-hexanoic acid;
2-(4'-Bromo-biphenyl-4-sulfonylamino)-6-[2-(4-methoxy-phenoxy)-acetyl amino]-hexanoic acid;
2-(4'-Bromo-biphenyl-4-sulfonylamino)-6-(4-phenyl-butyrylamino)-hexanoic acid;
2-(4'-Bromo-biphenyl-4-sulfonylamino)-6-[4-(4-chloro-3-methyl-phenoxy)-butyrylamino]-hexanoic acid;
2-(4'-Bromo-biphenyl-4-sulfonylamino)-6-[3-(4-chloro-phenyl)-propionyl amino]-hexanoic acid;
2-(4'-Bromo-biphenyl-4-sulfonylamino)-6-[3-(4-methoxy-phenyl)-propionylamino]-hexanoic acid;
2-(4'-Bromo-biphenyl-4-sulfonylamino)-6-(2-pyridin-3-yl-acetylamino)-hexanoic acid;
6-(2-Benzo[1,3]dioxol-5-yl-acetylamino)-2-(4'-bromo-biphenyl-4-sulfonyl amino)-hexanoic acid;
2-(4'-Bromo-biphenyl-4-sulfonylamino)-6-(2-naphthalen-1-yl-acetylamino)-hexanoic acid;

2-(4'-Bromo-biphenyl-4-sulfonylamino)-6-[3-(4-chloro-phenoxy)-propionylamino]-hexanoic acid;
2-(4'-Bromo-biphenyl-4-sulfonylamino)-6-(6-phenyl-hexanoylamino)-hexanoic acid;
2-(4'-Bromo-biphenyl-4-sulfonylamino)-6-(4-thiophen-2-yl-butyrylamino)-hexanoic acid;
2-(4'-Bromo-biphenyl-4-sulfonylamino)-6-(2,4,6-triisopropyl-benzoylamino)-hexanoic acid;
2-(4'-Bromo-biphenyl-4-sulfonylamino)-6-isobutoxycarbonylamino-hexanoic acid;
2-(4'-Bromo-biphenyl-4-sulfonylamino)-6-(9H-fluoren-9-ylmethoxycarbonylamino)-hexanoic acid;
6-(Adamantan-1-yloxycarbonylamino)-2-(4'-bromo-biphenyl-4-sulfonylamino)-hexanoic acid; and
6-Allyloxycarbonylamino-2-(4'-bromo-biphenyl-4-sulfonylamino)-hexanoic acid.

Numerous succinamide MMP inhibitors are known and can be utilized in the method of this invention. Typical succinamides include:
2S,N$^{1}$-Dihydroxy-3R-isobutyl-N$^{4}$-{1S-[2-(2-methoxy-ethoxymethoxy)ethylcarbamoyl]-2,2-dimethyl-propyl}-succinamide;
2S-Allyl-N$^{1}$-hydroxy-3R-isobutyl-N$^{4}$-{1S-[2-(2-methoxy-ethoxymethoxy)ethylcarbamoyl]-2-phenyl-ethyl}-succinamide;
2S-Allyl-N$^{1}$-hydroxy-3R-isobutyl-N$^{4}$-{1S-[2-(2-methoxy-ethoxymethoxy)ethylcarbamoyl]-2,2-dimethyl-propyl}-succinamide;
2S-Allyl-N$^{1}$-hydroxy-3R-isobutyl-N$^{4}$-(1S-{2-[2-(2-methoxy-ethoxy)-ethoxy]-ethylcarbamoyl]-2,2-dimethyl-propyl}-succinamide;
2S-Allyl-N$^{4}$-{1S-[2,2-di-(methoxymethyl)-propylcarbamoyl]-2,2-dimethyl-propyl}-N$^{1}$-hydroxy-3R-isobutyl-succinamide;
2S-Allyl-N$^{4}$-{1S-[2,2-di-(methoxymethyl)-butylcarbamoyl]-2,2-dimethyl-propyl}-N$^{1}$-hydroxy-3R-isobutyl-succinamide;
N$^{4}$-Hydroxy-2R-isobutyl-N$^{1}$-{1S-[2-(2-methoxy-ethoxy)-ethylcarbamoyl]-2,2-dimethyl-propyl}-3S-(thiophen-2-yl-sulfanylmethyl)-succinamide;
N$^{4}$-Hydroxy-2R-isobutyl-N$^{1}$-(1S-{2-[2-(2-methoxy-ethoxy)-ethoxy]-ethylcarbamoyl}-2,2-dimethyl-propyl)-3S-(thiophen-2-yl-sulfanylmethyl)-succinamide;
N$^{1}$-{1S-[2,2-Di-(methoxymethyl)-propylcarbamoyl]-2,2-dimethyl-propyl}-N$^{4}$-hydroxy-3R-isobutyl-3S-(thiophen-2-yl-sulfanylmethyl)-succinamide;
N$^{4}$-Hydroxy-2R-isobutyl-N$^{1}$-{1S-[2-(2-methoxy-ethoxy)-ethylcarbamoyl]-2,2-dimethyl-propyl}-3S-propyl-succinamide;
N$^{4}$-(1S-Cyclobutylcarbamoyl-2,2-dimethyl-propyl)-2S,N$^{1}$-dihydroxy-3R-isobutyl-succinamide;
N$^{4}$-(1S-Cyclopropylcarbamoyl-2,2-dimethyl-propyl)-2S,N$^{1}$-dihydroxy-3R-isobutyl-succinamide;
N$^{4}$-(1S-Cyclopentylcarbamoyl-2,2-dimethyl-propyl)-2S,N$^{1}$-dihydroxy-3R-isobutyl-succinamide;
N$^{4}$-(1S-Cyclohexylcarbamoyl-2,2-dimethyl-propyl)-2S,N$^{1}$-dihydroxy-3R-isobutyl-succinamide;
N$^{4}$-(1S-Cycloheptylcarbamoyl-2,2-dimethyl-propyl)-2S,N$^{1}$-dihydroxy-3R-isobutyl-succinamide;
N$^{4}$-(1S-Cyclopropylcarbamoyl-2-mercapto-2-methyl-propyl)-2S,N$^{1}$-dihydroxy-3R-isobutyl-succinamide;
N$^{4}$-(1S-Cyclopropylcarbamoyl-2,2-dimethyl-propyl)-2S,N$^{1}$-dihydroxy--3R-(3-phenyl-propenyl)-succinamide;
N$^{4}$-(1S-Cyclopropylcarbamoyl-2,2-dimethyl-propyl)-2S,N$^{1}$-dihydroxy-3R-(3-phenyl-propyl)-succinamide;
N$^{4}$-[2,2-Dimethyl-1S-(2-phenyl-cyclopropylcarbamoyl)-propyl]-2S,N$^{1}$-dihydroxy-3R-isobutyl-succinamide;

2S-Allyl-$N^{4-}$(1-cyclopropylcarbamoyl-2,2-dimethyl-propyl)-$N^{1-}$hydroxy-3R-isobutyl-succinamide;

2S-Allyl-$N^{4-}$(1S-cyclopropylcarbamoyl-2-mercapto-2-methyl-propyl)-$N^{1-}$hydroxy-3R-isobutyl-succinamide;

$N^{4-}$(1S-Cyclopropylcarbamoyl-2,2-dimethyl-propyl)-$N^{1-}$hydroxy-3R-isobutyl-2S-(thiophen-2-ylsulfanylmethyl)-succinamide;

$N^{4-}$(1S-Cyclopropylcarbamoyl-2,2-dimethyl-propyl)-$N^{1-}$hydroxy-2S-(4-hydroxy-phenylsulfanylmethyl)-3R-isobutyl-succinamide; and $N^{4-}$(1S-Cyclopropylcarbamoyl-2,2-dimethyl-propyl)-2S-(1,3-dioxo-1,3-dihydro-isoindol-2-ylmethyl)-$N^{1-}$hydroxy-3R-isobutyl-succinamide.

Another especially preferred group of MMP inhibitors to be utilized in the method of this invention are the sulfonated amino acid derivatives described in WO 97/27174, incorporated herein by reference. Those compounds have the general structure

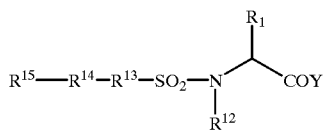

where $R^{11}$ is substituted or unsubstituted lower alkyl, substituted or unsubstituted aryl, substituted or unsubstituted aralkyl, substituted or unsubstituted heteroaryl, or substituted or unsubstituted heteroaryl alkyl;

$R^{12}$ is hydrogen, or a group as defined for $R^{11}$;

$R^{13}$ is a single bond, substituted or unsubstituted arylene, or substituted or unsubstituted heteroarylene;

$R^{14}$ is a single bond, —$(CH_2)_{1 \text{ or } 2}$—, —CH=CH—, —C°C—, —CO—, —CONH—, —N=N—, NH, N-alkyl, —NHCONH—, —NHCO—, —O—, —S—, —$SO_2NH$—, —$SO_2NH$—N=CH—, or tetrazoldiyl;

$R^{15}$ is substituted or unsubstituted aryl, substituted or unsubstituted heteroaryl, or substituted or unsubstituted non-aromatic heterocyclic group; and Y is NHOH or OH.

Especially preferred compounds to be employed in the method of this invention have the above formula wherein $R^{13}$ is phenylene or substituted phenylene. Typical of such compounds that can be employed have the formula

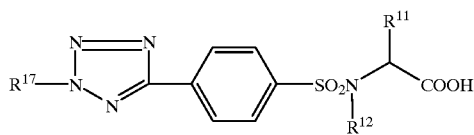

where $R^{11}$ and $R^{12}$ are as defined above, and $R^{17}$ is substituted or unsubstituted aryl or substituted or unsubstituted heteroaryl.

Especially preferred are compounds of the formula

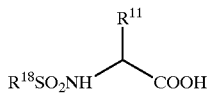

wherein $R^{11}$ and $R^{18}$ are as follows:

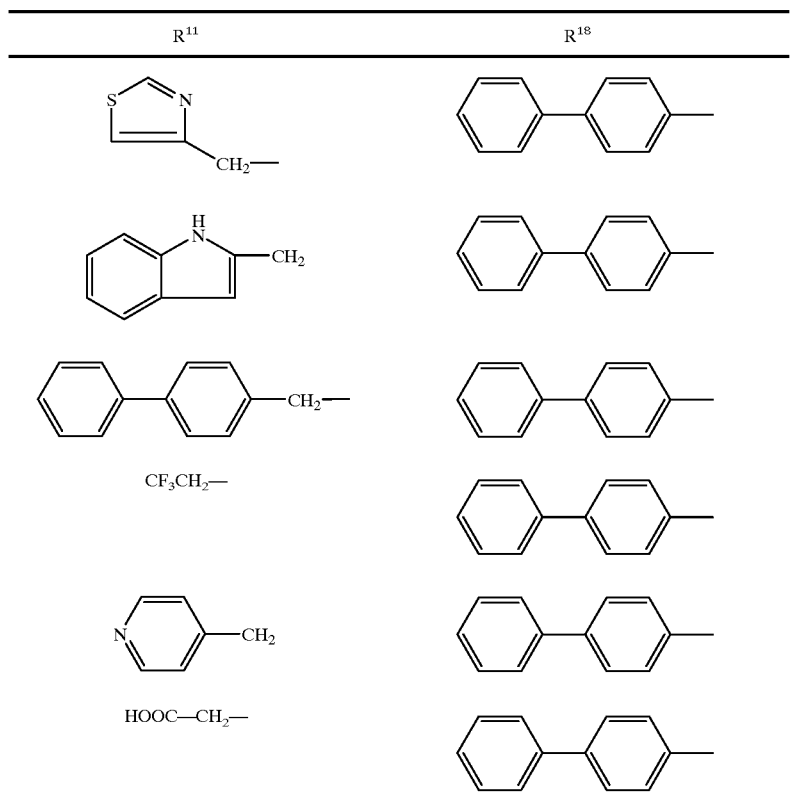

-continued
| R$^{11}$ | R$^{18}$ |
|---|---|
| 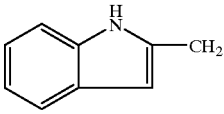 | 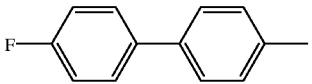 |
| (CH$_3$)$_2$CH— | 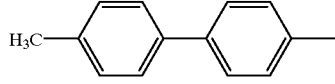 |
| (CH$_3$)$_2$CH— | 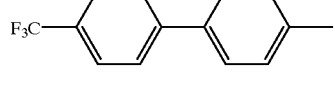 |
| 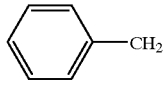 | 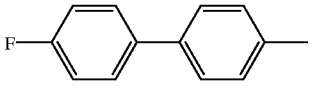 |
| (CH$_3$)$_2$CH— | 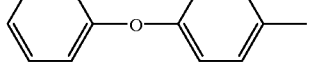 |
| 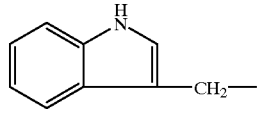 | 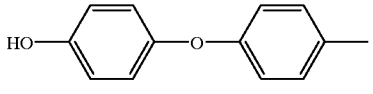 |
| 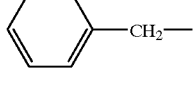 | 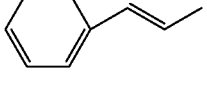 |
| 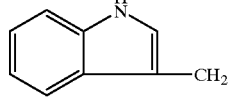 | 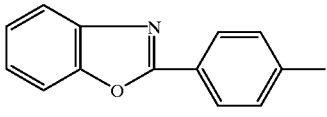 |
| 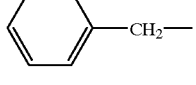 | 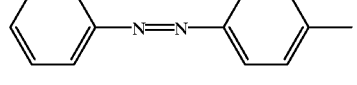 |
| (CH$_3$)$_2$CH— | 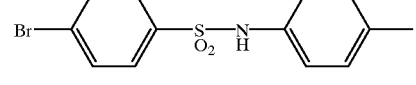 |
| (CH$_3$)$_2$CH— | 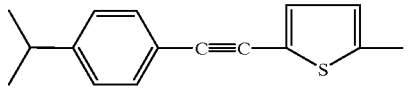 |
| 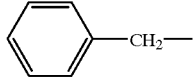 | 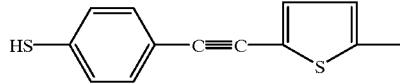 |
| (CH$_3$)$_2$CH— | 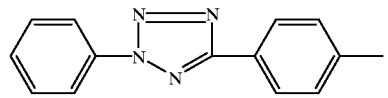 |

Especially preferred are the MMP inhibitors currently in clinical development, for example batimastat (2).

MMP compounds in clinical development include batimastat (2) for the treatment of malignant pleural effusion, and marimastat (1) for the treatment of pancreatic cancer. Galardin (3) is for the treatment of corneal ulcers, and a specific MMP-1 inhibitor is RO 31-9790 (4).

Compounds in Clinical Development (1)
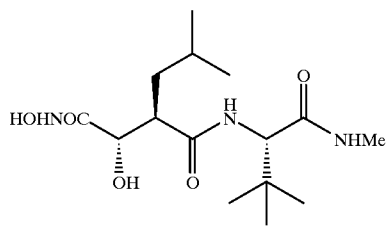

(2)
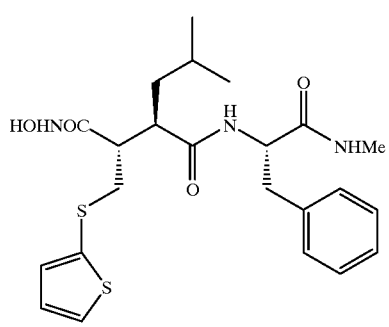

(3)
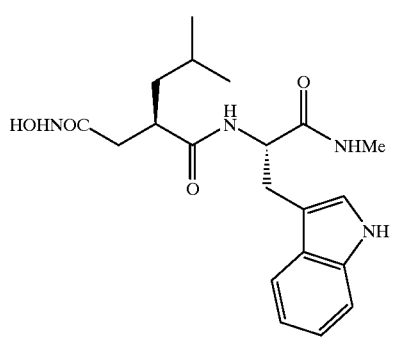

(4)
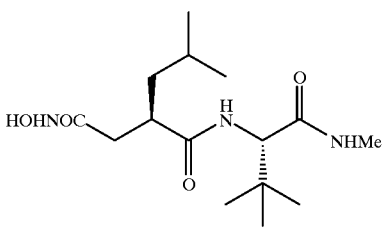

Compounds which can inhibit the actions of matrix metalloproteinase enzymes can be identified utilizing routine in vitro and in vivo assays. Several compounds from within the foregoing classes have been evaluated in such standard assays and determined to be potent matrix metalloproteinase inhibitors. The assays measure the amount by which a test compound reduces the hydrolysis of a thiopeptolide substrate caused by a matrix metalloproteinase enzyme. Such assays are described in detail by Ye, et al., in *Biochemistry*, Vol. 31, No 45, 1992, (11231–11235), which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Leu-Leu-Gly-O Et. A 100 μL assay mixture will contain 50 mM of 2-morpholinoethane sulfonic acid monohydrate (MES, pH 6.0) 10 mM $CaCl_2$, 100 μM thiopeptolide substrate, and 1 mM 5,5'-dithio-bis-(2-nitro-benzoic acid) DTNB). The thiopeptolide substrate concentration is varied from 10 to 800 μM to obtain Km and Kcat values. The change in absorbance at 405 nm is monitored on a Thermo Max microplate reader (molecular Devices, Menlo Park, Calif.) at room temperature (22° C.). The calculation of the amount of hydrolysis of the thiopeptolide substrate is based on $E_{412}=13600$ $m^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table I below presents inhibitory activity for compounds from various classes. In the table, MMP-1 refers to interstitial collagenase; MMP-2 refers to Gelatinase A; MMP-3 refers to stromelysin; MMP-7 refers to matrilysin; and MMP-9 refers to Gelatinase B. Test compounds were evaluated at various concentrations in order to determine their respective $IC_{50}$ values, the micromolar concentration of compound required to cause a 50% inhibition of the hydrolytic activity of the respective enzyme.

TABLE I ($IC_{50}$ μM)

|  | MMP1 | MMP2 | MMP3 | MMP7 | MMP9 |
|---|---|---|---|---|---|
| Batimastat is $N^4$-Hydroxy-$N^1$-[2-(methylamine)-2-oxo-1-(phenylmethyl)ethyl]-2-(2-methylpropyl) 3-[(2-thienylthio)methyl]-butanediamide | 0.005 | 0.004 | 0.02 |  |  |
| CDP-845 (Celltech) |  | 0.303 | 0.0015 | 0.01 |  |
| CGS 27023A (Ciba-Giegy) | 0.033 | 0.01 | 0.91 |  | 0.008 |
| Galardin is $N^4$-Hydroxy-$N^1$-[2-(methylamine)-2-oxo-1-(3-indolylmethyl)ethyl]-2-(2-methylpropyl)-butanediamide | 0.0004 | 0.0005 | 27 |  | 0.0002 |
| U24522 (Merck) |  | 0.05 | 0.02 |  |  |
| RO-31-9790 (Roche) | 0.0055 | 0.006 | 0.47 |  |  |
| 4-Oxo-4-[4-(4-phenyl-piperidin-1-yl)-phenyl]-butyric acid |  | 1.3 | 0.14 |  |  |
| N-Hydroxy-4-oxo-4-[4-(4-phenyl-piperidin-1-yl)-phenyl]-butyramide |  | 0.04 | 0.02 |  |  |
| 4-Oxo-4-[4-(4-phenyl-piperazin-1-yl)-phenyl]-butyric acid |  | 1.6 | 0.25 |  |  |
| [4-(4-Phenyl-piperidin-1-yl)-benzenesulfonylamino]-acetic acid |  | 0.21 | 0.02 |  |  |

TABLE I-continued (IC$_{50}$μM)

| | MMP1 | MMP2 | MMP3 | MMP7 | MMP9 |
|---|---|---|---|---|---|
| N-Hydroxy-2-[4-(4-phenyl-piperidin-1-yl)-benzene-sulfonylamino]-acetamide | | 0.81 | 0.019 | | |
| (S)-3-Phenyl-2-[4-(4-phenyl-piperidin-1-yl)-benzene-sulfonylamino]-propionic acid | | 0.22 | 0.014 | | |
| (S)-2-[4-(4-Benzyl-piperidin-1-yl)-benzenesulfonyl-amino]-3-phenyl-propionic acid | | 0.088 | 0.021 | | |
| (S)-2-{4-[-4-(4-Methoxy-phenyl)-piperazin-1-yl]-benzenesulfonylamino}-3-phenyl-propionic acid | | 0.033 | 0.014 | | |
| (S)-2-(4'-Bromo-biphenyl-4-sulfonylamino)-3-methyl-butyric acid | 3.24 | 0.025 | 0.012 | | |
| (S)-3-Methyl-2-(4'-nitro-biphenyl-4-sulfonylamino)-butyric acid; | | 0.013 | 0.10 | | |
| (S)-2-(4'-Amino-biphenyl-4-sulfonylamino)-3-methyl-butyric acid | | 0.044 | 0.067 | | |
| (S)-2-(4'-Bromo-biphenyl-4-sulfonylamino)-3-phenyl-propionic acid | | 0.026 | 0.026 | | |
| 4-(4'-Chloro-biphenyl-4-yl)-4-hydroxyimino-butyric acid | | 0.39 | 0.12 | | |
| 4-(4'-Bromo-biphenyl-4-yl)-4-hydroxyimino-butyric acid | | 0.058 | 0.11 | | |
| 4-(4'-Chloro-biphenyl-4-yl)-4-(dimethylhydrazono)-butyric acid | | 0.73 | 0.93 | | |
| (±)-4-(4'-Chloro-biphenyl-4-yl)-4-hydroxy-butyric acid | | 0.15 | 0.28 | | |
| (S)-2-(Dibenzofuran-2-sulfonylamino)-4-phenyl-butyric acid | | 0.265 | 0.46 | | |
| (L)-2-(Dibenzofuran-2-sulfonylamino)-4-methyl-pentanoic acid | | 0.32 | 1.18 | | |
| (L)-2-(Dibenzofuran-2-sulfonylamino)-3-phenyl-propionic acid | | 0.89 | 0.72 | | |
| (L)-2-(Dibenzofuran-2-sulfonylamino)-3-methyl-butyric acid | | 0.084 | 0.23 | | |
| (L)-2-(Dibenzofuran-2-sulfonylamino)-3-tritylsulfanyl-propionic acid | | 9.4 | 14.4 | | |
| (L)-2-(Dibenzofuran-2-sulfonylamino)-3-mercapto-propionic acid | | 4.45 | 0.69 | | |
| (S)-4-(Dibenzofuran-2-yl-4-oxo-2-(2,2,2-trifluoroacetylamino)-butyric acid | | 0.72 | 1.33 | | |
| (S)-2-Amino-4-dibenzofuran-2-yl-4-oxo-butyric acid | | 3.8 | 33.0 | | |
| (S)-2-Acetylamino-4-dibenzofuran-2-yl-4-oxo-butyric acid | | 0.16 | 1.55 | | |
| (S)-4-Dibenzofuran-2-yl-4-oxo-2-phenylacetylamino-butyric acid | | 0.084 | 0.33 | | |
| (S)-4-Dibenzofuran-2-yl-4-oxo-2-(3-phenyl-propionylamino)-butyric acid | | 0.096 | 0.28 | | |

The ACE inhibitors to be employed in the compositions of this invention are similarly well known in the art, and several are used routinely for treating hypertension. For example, captopril and its analogs are described in U.S. Pat. Nos. 5,238,924 and 4,258,027. Enalapril, enalaprilat, and closely related analogs are described in U.S. Pat. Nos. 4,374,829, 4,472,380, and 4,264,611. Moexipril, quinapril, quinaprilat, and related analogs are described in U.S. Pat. Nos. 4,743,450 and 4,344,949. Ramipril and its analogs are described in U.S. Pat. Nos. 4,587,258 and 5,061,722. All of the foregoing patents are incorporated herein by reference for their teaching of typical ACE inhibitors which can be utilized in combination with an MMP inhibitor according to this invention. Other ACE inhibitors which can be utilized include fosinopril, fasidotril, glycopril, idrapril, imidapril, mixanpril, perindopril, spirapril, spiraprilat, temocapril, trandolapril, zofenopril, zofenoprilat, utilapril, sampatrilat, SA 7060, DU 1777, BMS 186716. and C 112.

The compositions will contain an ACE inhibitor and an MMP inhibitor in a weight ratio of about 0.05:1 to about 1000:1, and typically about 1:1 to about 500:1, and ideally about 1:1 to about 5:1. A typical composition, for example, will have 20 mg of quinapril hydrochloride and about 10 mg of (S)-2-(4'-bromobiphenyl-4-sulfonylamino)-3-methyl-butyric acid. All that is required is that amounts of each component are used which are effective to inhibit or reverse fibrosis ventricular dilation, and heart failure.

The combination of an ACE-inhibitor with an MMP inhibitor has been shown to be synergistic in its ability to treat cardiovascular fibrotic pathologies such as heart failure.

EXAMPLE 1

This experiment was performed to determine the long-term benefits of matrix metalloprotease inhibitor (MMP-I) treatment, and whether coadministration of an MMP-I and angiotensin converting enzyme inhibitor (ACE-I) has a synergistic effect in the treatment of heart failure (HF). A previous experiment showed that administration of the MMP-I, PD 166793, for 4 months was effective in signifi-cantly reducing cardiac dilation and maintaining left ventricular (LV) systolic function in spontaneously hypertensive heart failure (SHHF) rats. A similar effect was also observed in SHHF rats treated with the ACE-I quinapril. PD 166793, which is 2-(4'-bromobiphenyl-4-sulfonylamino)-3-methyl-butyric acid, appeared to act by a mechanism different from that of quinapril in that it was neither a vasodilator, nor an anti-hypertrophic. Five groups of rats (n=14 per group) were tested: 17-month-old normotensive Fischer control Rats (F-1 7); vehicle treated 17-month-old SHHF Rats (SHHF-17); PD 166793-0000 (Lot Y) SHHF Rats (SHHF-793); Quinapril (PD 109452-0002, Lot Y) SHHF Rats (SHHF-Q); PD 166793 +Quinapril SHHF Rats (SHHF-793Q). Naive Fischer rats were acclimatized 2 weeks prior to testing. All SHHF rats were maintained in-house, administered drug for 8 months, and then cardiovascular tests were performed and tissue samples taken. The primary endpoint for the study was the prevention of cardiac dilation as determined by left ventricular pressure volume relations in the excised KCl arrested heart.

Drug Administration: All SHHF rats were fed powdered rat chow for 1 week prior to drug administration, and daily food consumption was measured by weighing the foodcups. Drug was added to powdered rat chow so that rats consumed their daily dose of PD 166793 (5 mg/kg/day), quinapril (10 mg/kg/day), or both drugs in combination. Food consumption was monitored twice weekly.

Terminal Cardiovascular Test: Rats were anesthetized with isoflurane for terminal testing. Isoflurane was administered using a mask until the rats are anesthetized and a tracheotomy performed. The rats were respired using a ventilator (A.D.S. 1000, Engler Engineering Corp., Hialeah, Fla.). Cardiac function was assessed in closed-chest rats by measuring LV dP/dt, LV end-diastolic pressure (EDP), heart rate, and aortic blood pressure using a Millar pressure transducer inserted through the right carotid. Physiological data was recorded at 500 Hz, and a logging rate of 5 seconds was used to average data. The amount of isoflurane used for anesthesia was decreased to 1.5% prior to taking cardiovascular measurements. Baseline measurements were made when the rats reached a stable plateau of anesthesia. Normotensive rats had their blood pressure increased by partial occlusion of the aorta so that cardiovascular function could be assessed at a pressure of 180 mmHg, the projected blood pressure of SHHF rats. Approximately 4 to 5 mL of blood were withdrawn in ice-cold syringes and then transferred to ice-cold EDTA tubes. Blood was centrifuged at 4500 RPM for 10 minutes so that plasma could be stored for drug measurements, and measuring collagen breakdown products. The heart was arrested with KCl and rapidly excised. A glass cannula was inserted through the aorta into the LV chamber, and secured into place by a ligature around the atrio-ventricular groove. Cardiac dilation was measured by generating left ventricular pressure volume (PV) curves. The PV curves was generated by evacuating the LV of saline and then filling the LV at a fixed rate using a programmable pump set at a 1 mL/min flow rate. The PV curves were recorded on a Po-Ne-Mah digital data acquisition system. A 2 to 3 mm cross-section of the heart was removed (at the level of the papillary muscles). The remainder of the heart was rapidly divided into RV and LV tissue that was frozen in liquid N2 for subsequent weighing and biochemical analysis. The cross-sections were fixed in buffered formalin for histology. This procedure will allow LV, and RV weights to be determined and hypertrophy to be assessed.

Results: The SHHF-793 and coadministration group had PD 166793 plasma levels of 50.1±7.1 and 76.2±8.2 µg/mL, respectively. FIG. 1 shows that significant mortality occurred in the vehicle treated SHHF rats, and that the group receiving the combination therapy had less mortality than either of the groups receiving monotherapy.

Table I below shows that mean left ventricular end-systolic and end-diastolic pressure (LVESP and LVEDP, respectively) was lower in all drug treatment groups compared to the vehicle control group. LV weight was reduced in the quinapril and coadministration groups compared to the vehicle control group. All drug treatment groups had reduced cardiac dilation compared to the vehicle control group.

TABLE I

|  | N | LVESP (mmHg) | LVEDP (mmHg) | LV Wt (g) | LVV-OP (µL) |
| --- | --- | --- | --- | --- | --- |
| CONT | 14 | 162 ± 5 | 7 ± 2 | 706 ± 15 | 198 ± 37 |
| VEH | 3 | 205 ± 25 | 37 ± 2 | 1529 ± 86 | 1209 ± 43 |
| 793 | 7 | 188 ± 8 | 18 ± 3 | 1472 ± 63 | 820 ± 58 |
| Q | 10 | 190 ± 7 | 17 ± 4 | 1052 ± 65 | 603 ± 99 |
| 793 + Q | 10 | 162 ± 11 | 12 ± 4 | 1154 ± 73 | 600 ± 68 |

The coadministration group had a synergistic effect on LVESP which indicates that lower doses of ACE-inhibitors may be used to lower blood pressure.

Conclusions: The results from the 8-month progression study in SHHF rats shows that coadministration of an MMP-inhibitor and an ACE-inhibitor have a synergistic effect by decreasing the rate of mortality as well as a synergistic effect on lowering blood pressure.

EXAMPLE 2

Another study was performed to determine whether MMP- and ACE-inhibition act synergistically in the paced pig model of heart failure. In this study pigs were rapidly paced (240 BPM) for 3 weeks to induce heart failure. Pigs were randomly assigned to 1- of 5-paced groups: (1) no drug treatment (N=8), (2) fosinopril (F, 2.5 mg/kg-BID PO, N=8), (3) PD 166793 (793, 2 mg/kg/day-PO, N=8), (4) fosinopril plus PD 166793 (793+F), and (5) sham controls. All drug treatments were started 3 days prior to the initiation of pacing and continued for the entire 21-day pacing protocol. Left ventricular (LV) and remodeling were assessed weekly in sedated pigs using two-dimensional and M-mode echocardiography with the pacer turned off. At Day 21 of the study, a final set of LV function and hemodynamic measurements were made while the animals were under anesthesia with the pacer turned off, and blood was taken to determine peak plasma drug levels at one hour post-dose. Plasma drug levels were 10.8±1.2 µg/mL for the PD 166793 monotherapy group, and 11.3±1.3 µg/mL for the PD 166793 plus fosinopril coadministration group. Table II below shows the effects of drug treatment on hemodynamic function.

TABLE II

|  | CONT | VEH | 793 | F | 793 + F |
| --- | --- | --- | --- | --- | --- |
| LV End-Systolic Pressure (mmHg) | 120 ± 3 | 103 ± 4 | 110 ± 3 | 100 ± 5 | 84 ± 4 |
| Systemic Vascular Resistance (dynes*s*cm$^{-5}$) | 1977 ± 100 | 2521 ± 194 | 2784 ± 338 | 1529 ± 174 | 1310 ± 143 |
| Pulmonary Vascular Resistance (dynes*s*cm$^{-5}$) | 159 ± 131 | 378 ± 66 | 417 ± 158 | 266 ± 68 | 178 ± 54 |
| Plasma Norepinephrine (pg/mL) | 262 ± 28 | 963 ± 133 | 736 ± 161 | 618 ± 51 | 311 ± 61 |

Pacing-induced heart failure resulted in an increase in systemic vascular and pulmonary resistance as well as plasma norepinephrine. These changes resemble the clinical syndrome of human heart failure. ACE-inhibition, but not MMP-inhibition, lowered these three factors when compared to the vehicle group. In addition, coadministration had a synergistic effect on resistance, plasma norepinephrine, and LV end-systolic pressure. The later effect on pressure parallels the observation in the SHHF rat coadministration study of Example 1.

Figure 2B:
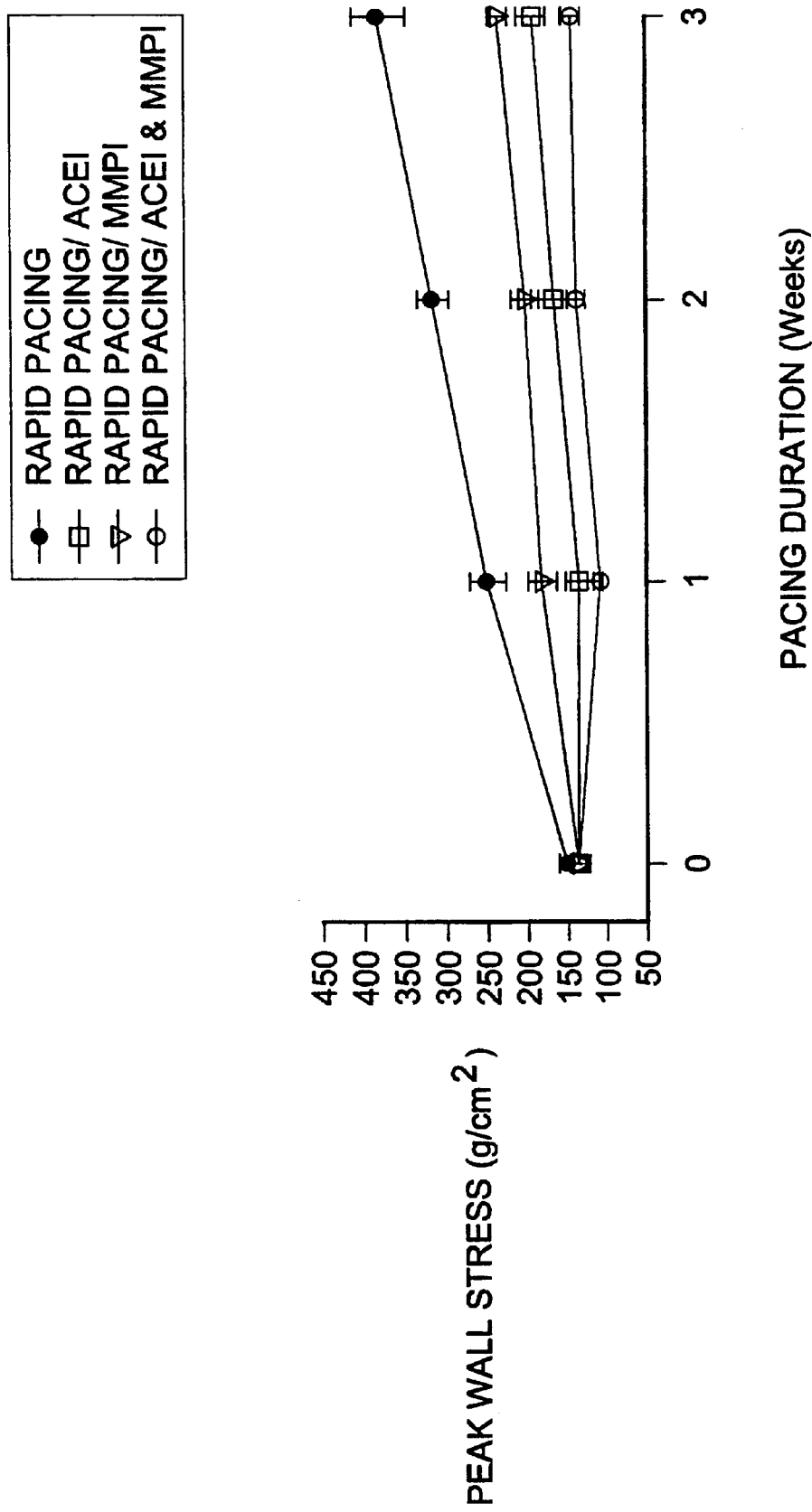
Figure 2C:
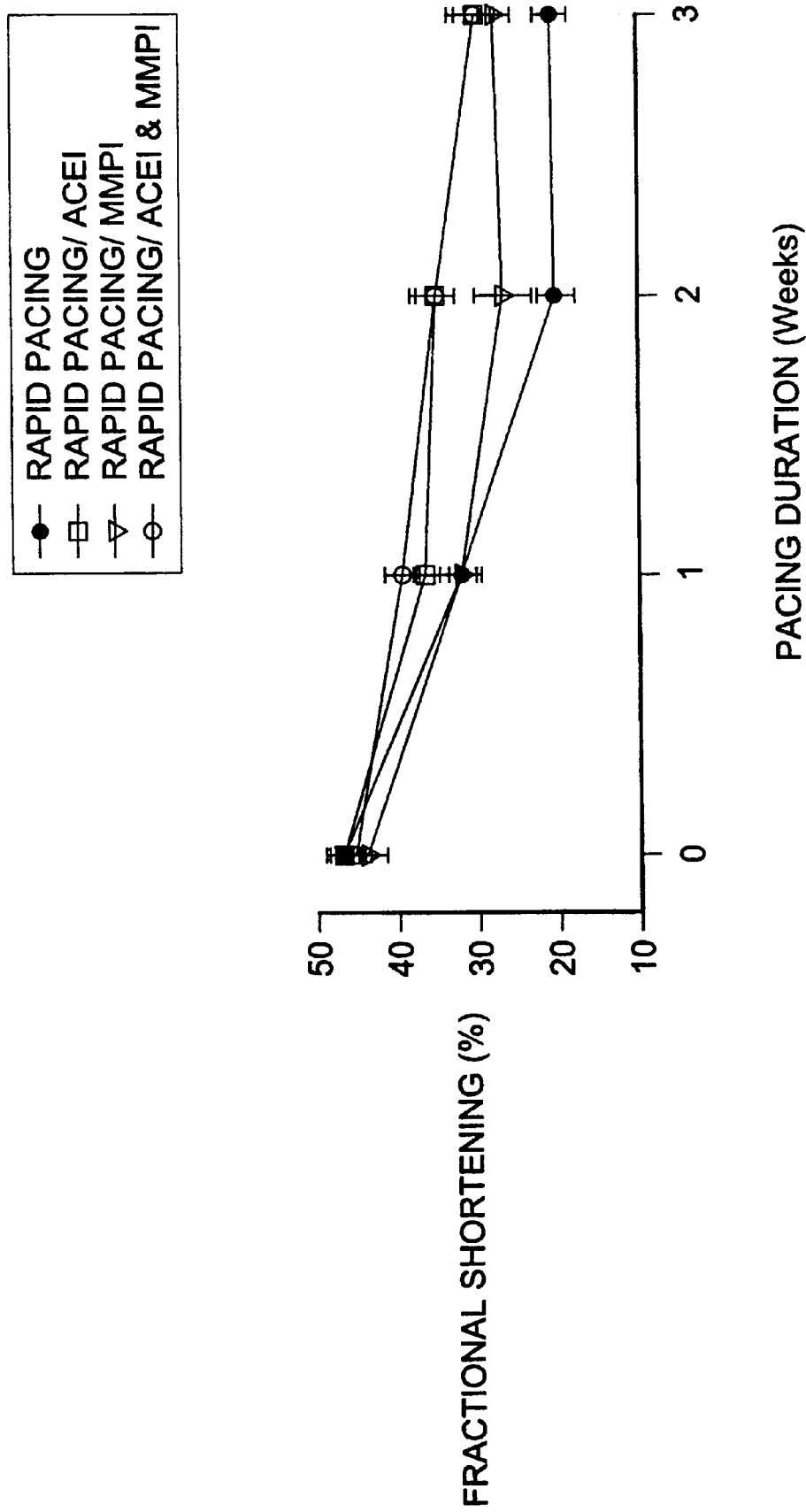
Figure 4:
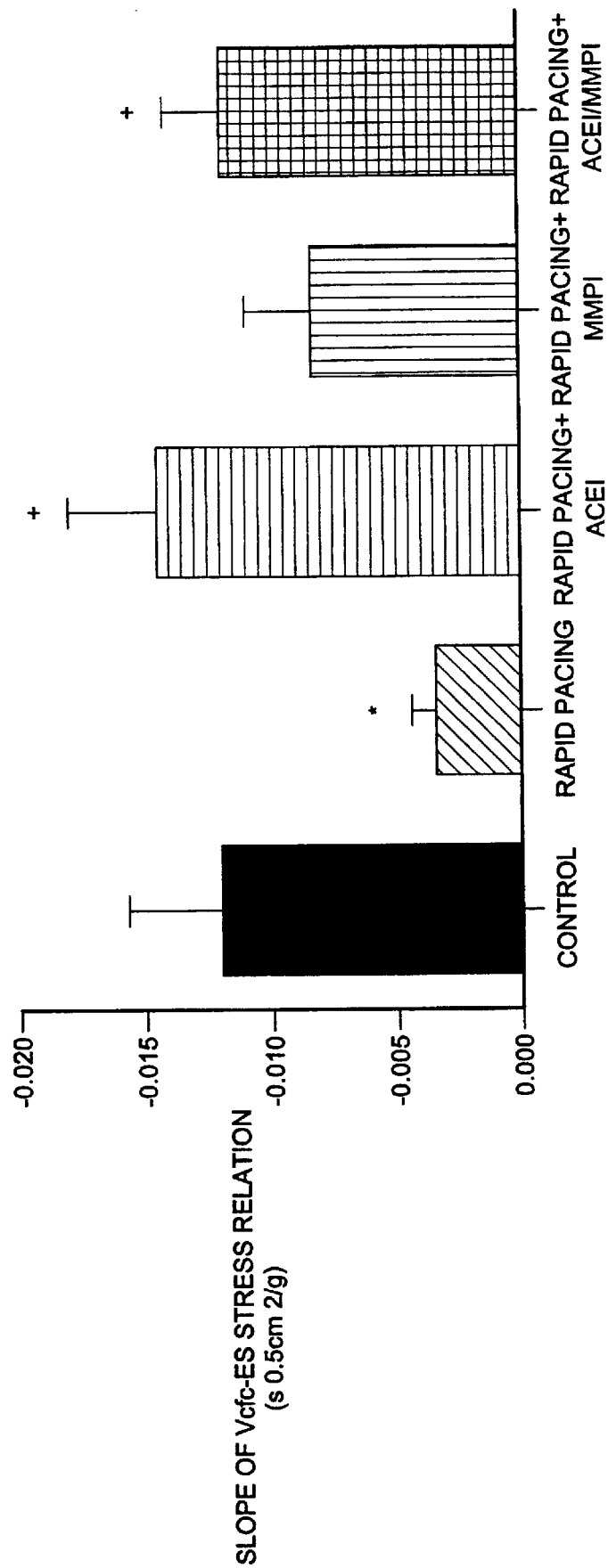
FIG. 4 shows the drug effect on LV function when measured by the slope of circumferential velocity over end-systolic stress relation (Vcfc-ES Stress). Both fosinopril and fosinopril plus 166793 significantly improved systolic function compared to the nontreated rapid-paced animals.

The effect of drug treatment on the echocardiographic measurements of LV dilation and function are shown in FIG. 2. All drug treatments reduced the increase in LV end-diastolic dimension (dilation) over the 3-week pacing period. Fosinopril ACE-inhibitor monotherapy and coadministration was more effective than the PD 166793 in reducing dilation. Peak LV wall stress increased progressively during the development of heart failure because of LV dilation and wall thinning. All drug treatments reduced wall stress; however, the PD 166793 and fosinopril coadministration group showed the greatest mean decrease in this parameter. LV fractional shortening was reduced progressively during the 3-week pacing period. All 3 drug treatments preserved LV fractional shortening at 3 weeks of rapid pacing. Percent fractional shortening reflects both LV geometric as well as systolic functional changes.

In another embodiment, this invention provides a method for treating cardiovascular fibrotic pathologies. As used herein, "fibrotic" and "fibrosis" means those disorders or disease states that are caused by the abnormal deposition of scar tissue and remodeling. "Remodeling" is a pathologic process that involves changes in myocardiocyte structure as well as changes in the amount and composition of the surrounding interstitial connective tissue. The interstitial collagen matrix is subject to increased dissolution and repair during remodeling that leads to ventricular enlargement and progressive heart failure. Fibrosis includes, but is not limited to, cardiovascular fibrosis such as that associated with left ventricular hypertrophy, myocardial infarctions, dilated cardiomyopathy, valvular heart disease, and myocarditis. Other disease states which are fibrotic in nature and can be treated according to this invention include cardiac valvular sclerosis and fibrosis of the cardiac valves, rheumatic heart disease, arteriosclerotic disorders, pulmonary fibrosis, adult respiratory distress syndrome, inflammatory disorders, ankylosing spondylitis, glomerulo sclerosis, adhesions of the peritoneum, strictures of the esophagus or bowel, urethral strictures, biliary strictures, pelvic inflammatory disease, scleroderma, cirrhosis, keloids, and hypertrophic scars.

The compositions to be employed in the present invention can be prepared and administered in a wide variety of oral and parenteral dosage forms for treating and preventing heart failure and ventricular dilation. The compounds can be administered by injection, that is, intravenously, intramuscularly, intracutaneously, subcutaneously, submucosally, intraductally, intraduodenally, or intraperitoneally. Also, the compounds can be administered by inhalation, for example, intranasally. Additionally, the compositions can be administered transdermally. It will be obvious to those skilled in the art that the following dosage forms may comprise as the active component, either a compound as a free base, acid, or a corresponding pharmaceutically acceptable salt of such compound. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of each active component in a unit-dose preparation may be varied or adjusted from 1 to 1000 mg, preferably 10 to 100 mg according to the particular application and the potency of the active component. The composition can, if desired, also contain other compatible therapeutic agents.

The following examples illustrate typical formulations that can be utilized in the invention.

| Tablet Formulation | |
|---|---|
| Ingredient | Amount (mg) |
| 2-(4'bromobiphenyl-4-sulfonylamino)-3-methyl-butyric acid | 25 |
| Quinapril hydrochloride | 20 |
| Lactose | 30 |
| Corn starch (for mix) | 10 |
| Corn starch (paste) | 10 |
| Magnesium stearate (1%) | 5 |
| Total | 100 |

The biphenylsulfonamide, ACE inhibitor, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of fibrosis and ventricular dilation associated with myocardial infarction.

| Preparation for Oral Solution | |
|---|---|
| Ingredient | Amount |
| (R)-2-(4'-Cyanobiphenyl-4-sulfonylamino)-3-phenyl-propionic acid sodium salt | 400 mg |
| Quinapril | 20 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the biphenylsulfonamide and ACE inhibitor are dissolved therein. The saccharin, sodium benzoate, flavor, and dye are added and dissolved. The volume is adjusted to 100 mL with distilled water. Each milliliter of syrup contains 4 mg of invention composition.

Parenteral Solution

In a solution of 700 mL of propylene glycol and 200 mL of water for injection is suspended 20 g of (S)-2-(4'-amino-biphenyl-4-sulfonylamino)-3-(3-ethoxyphenyl)-propionic acid and 5 g of enalaprilat. After suspension is complete, the pH is adjusted to 6.5 with 1 N sodium hydroxide, and the volume is made up to 1000 mL with water for injection. The formulation is sterilized, filled into 5.0 mL ampoules each containing 2.0 mL, and sealed under nitrogen.

What is claimed is:

1. A pharmaceutical composition comprising an effective amount of an angiotensin-converting enzyme inhibitor and an effective amount of a matrix metalloproteinase inhibitor.

2. A composition according to claim 1 employing an ACE inhibitor selected from captopril, enalapril, enalaprilat, lisinopril, ramipril, zofenopril, trandolapril, temocapril, ceranapril, alacepril, delapril, pentopril, quinapril, quinaprilat, moexipril, rentiapril, duinapril, spirapril, cilazapril, perindopril, and fosinopril.

3. A composition according to claim I employing an MMP inhibitor selected from

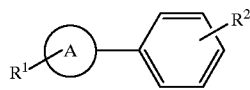

wherein:

A is phenyl or

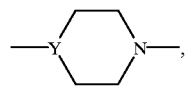

where Y is CH or N;

$R^1$ is a substituent such as alkyl, aryl, halo, amino, substituted and disubstituted amino, and alkoxy;

$R^2$ is carboxyalkyl ketone or oxime, or a carboxyalkyl sulfonamide such as

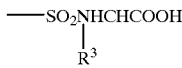

where $R^3$ is alkyl, substituted alkyl, amino, substituted and disubstituted amino, and aryl, preferred alkyl and alkoxy groups are $C_1$–$C_{10}$ alkyl and $C_1$–$C_{10}$ alkoxy, which can be straight chain or branched, and optionally substituted by halo, amino, nitro, carboxy, hydroxy, aryl, and heteroaryl.

4. A composition according to claim 3 in which the MMP inhibitor is

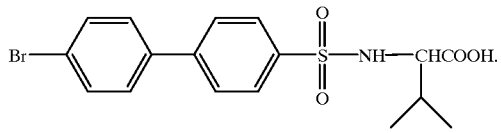

5. A composition according to claim 2 employing a matrix metalloproteinase inhibitor which is a substituted fused tricyclic compound of the formula

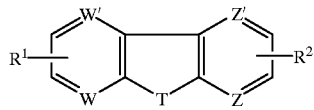

where $R^1$ and $R^2$ are as defined above, T is O, $CH_2$, SQ $(O)_{0,1\ or\ 2}$, C=O, $NR^3$, or

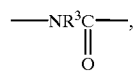

and W, $W^1$, Z, and $Z^1$ are each the same or different and each is $CR^3$, where $R^3$ is alkyl, halo, alkoxy, acyl, and aryl.

6. A composition according to claim 5, wherein the MMP inhibitor is a compound of the formulas

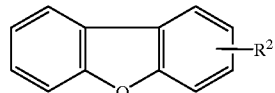

and

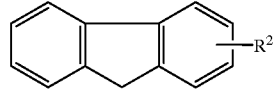

where $R^2$ is, for instance,

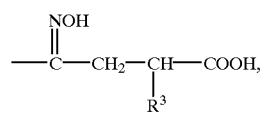

or

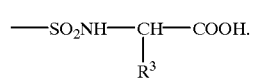

7. A composition according to claim 2 employing an ACE inhibitor selected from quinapril hydrochloride, ramipril, enalapril, or moexipril.

8. A composition according to claim 7 employing an MMP inhibitor selected from 4-(4'-chlorobiphenyl-4-yl)-4-hydroxyimino-butyric acid or 2-(4'-bromobiphenyl-4-sulfonylamino)-3-methyl-butyric acid.

9. A method for treating fibrosis, ventricular dilation, and/or heart failure in a mammal comprising administering an antifibrotic effective amount of a combination of at least one angiotensin-converting enzyme inhibitor and at least one matrix metalloproteinase inhibitor.

10. A method according to claim 9 wherein the fibrosis is associated with a disorder selected from cardiovascular fibrosis, dilated cardiomyopathy, valvular heart disease, cardiac valvular sclerosis, fibrosis of the cardiac valves, rheumatic heart disease, arteriosclerotic disorders, pulmonary fibrosis, adult respiratory distress syndrome, inflammatory disorders, ankylosing spondylitis, glomerulo sclerosis, adhesions of the peritoneum, strictures of the esophagus or bowel, ureteral or urethral strictures, biliary strictures, pelvic inflammatory disease, scleroderna, cirrhosis, keloids, and hypertrophic scars.

* * * * *